US012599549B2

(12) United States Patent　　(10) Patent No.: US 12,599,549 B2
Pickett et al.　　(45) Date of Patent: Apr. 14, 2026

(54) TREATMENT OF MODERATE TO VERY SEVERE GLABELLAR LINES AND LATERAL CANTHAL LINES

(71) Applicants: Ipsen Biopharm Limited, Wrexham (GB); GALDERMA HOLDING SA, Zug (CH)

(72) Inventors: Andrew Pickett, Uppsala (SE); Birgitta Almegård, Uppsala (SE); Charlotta Gauffin, Vänge (SE); Aleksandra Karin, Uppsala (SE); Anna Nilsson, Uppsala (SE); Axel Emilson, Uppsala (SE)

(73) Assignees: Ipsen Biopharm Limited, Wrexham (GB); Galderma Holding SA, Zug (CH)

( * ) Notice: Subject to any disclaimer, the term of this patent is extended or adjusted under 35 U.S.C. 154(b) by 294 days.

(21) Appl. No.: 16/894,684

(22) Filed: Jun. 5, 2020

(65) Prior Publication Data

US 2020/0383894 A1　　Dec. 10, 2020

Related U.S. Application Data

(60) Provisional application No. 62/858,766, filed on Jun. 7, 2019.

(51) Int. Cl.
*A61K 8/66*　　(2006.01)
*A61K 38/48*　　(2006.01)
*A61Q 19/08*　　(2006.01)

(52) U.S. Cl.
CPC ............ *A61K 8/66* (2013.01); *A61K 38/4893* (2013.01); *A61Q 19/08* (2013.01)

(58) Field of Classification Search
CPC ....... A61K 8/66; A61K 38/4893; A61Q 19/08
See application file for complete search history.

(56) References Cited

U.S. PATENT DOCUMENTS

2005/0238664 A1* 10/2005 Hunt ........................ A61K 9/19
　　　　　　　　　　　　　　514/18.2
2015/0165003 A1 6/2015 Jung et al.
2018/0071361 A1 3/2018 Abiad et al.

FOREIGN PATENT DOCUMENTS

| CN | 103705913 A | 4/2014 |
|---|---|---|
| EA | 030252 B1 | 7/2018 |
| WO | WO-2013/102144 A2 | 7/2013 |
| WO | WO-2015/089452 A1 | 6/2015 |
| WO | WO-2017/203038 A1 | 11/2017 |
| WO | WO-2018/038585 A1 | 3/2018 |

OTHER PUBLICATIONS

Zbacnik et al. 2017 (Role of Buffers in Protein Formulations; Journal of Pharmaceutical Sciences 106: 713-733) (Year: 2017).*
Small et al. Am Fam Physician. 2014;90(3):168-175.*
Ascher et al. JEADV 2010, 24, 1278-1284.*
Sodium Phosphate. Cold Spring Harbor Protocols. doi:10.1101/pdb.rec8303 Cold Spring Harb Protoc 2006.*
Kukerja et al. Research and Reports in Biochemistry. 2015;5:173-183.*
Bank et al. Plast Aesthet Res 2015;2:12-6.*
Rasouli et al. Clinical Biochemistry 49 (2016) 936-941.*
Matarasso et al. Aesthetic Surgery Journal, vol. 29 No. 65, pp. S72-S79, 2009.*
Galderma Annouces Phase 3 Trials for Liquid Neurotoxin. Oct. 19, 2020. Retrieved from https://www.medestheticsmag.com/new/news/21198355/galderma-announces-phase-3-trials-for-liquid-neurotoxin.*
Statement on a nonproprietary name adopted by the USAN Council Relabotulinumtoxina , Sep. 25, 2019.*
Galderma to Present Five Abstracts in Support of Novel Aesthetics Solutions and Pipeline at ASDS 2020 Annual Meeting. Galderma, Oct. 9, 2020.*
Ascher, MD, Benjamin, et al., "Liquid Formulation of AbobotulinumtoxinA Exhibits a Favorable Efficacy and Safety Profile in Moderate to Severe Glabellar Lines: A Randomized, Double-Blind, Placebo- and Active Comparator-Controlled Trial," Aesthetic Surgery Journal, Feb. 14, 2017, vol. 38(2) 183-191, XP055714338, US ISSN: 1090-820X, DOI: 10.1093/asj/sjw272.
Ascher, MD, Benjamin, et al., "Liquid Formulation of AbobotulinumtoxinA: A 6-Month, Phase 3, Double-Blind, Randomized, Placebo-Controlled Study of a Single Treatment, Ready-to-Use Toxin for Moderate-to-Severe Glabellar Lines," Aesthetic Surgery Journal, Mar. 20, 2019, vol. 40, No. 1, pp. 93-104, XP055714341, US ISSN: 1090-820X, DOI: 10.1093/asj/sjz003.
International Search Report issued in corresponding International Application No. PCT/IB2020/055340 dtd Aug. 18, 2020.

* cited by examiner

*Primary Examiner* — Oluwatosin A Ogunbiyi
(74) *Attorney, Agent, or Firm* — Sunit Talapatra; Foley & Lardner, LLP

(57)　　ABSTRACT

Disclosed herein are methods of treatment of moderate to severe and very severe glabellar lines and lateral canthal lines using liquid botulinum neurotoxin compositions. Also disclosed are liquid compositions of botulinum neurotoxin.

25 Claims, 24 Drawing Sheets

FIG. 1
MAS GL Scale at Rest
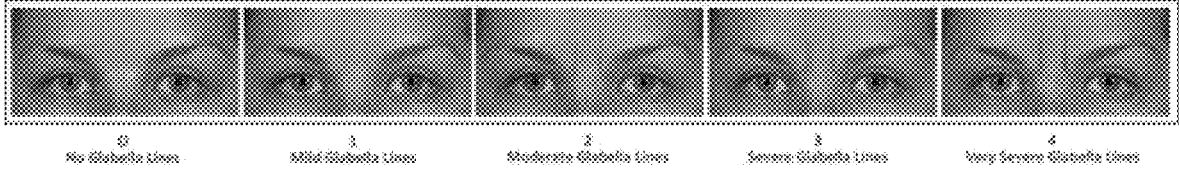
MAS GL Scale Dynamic
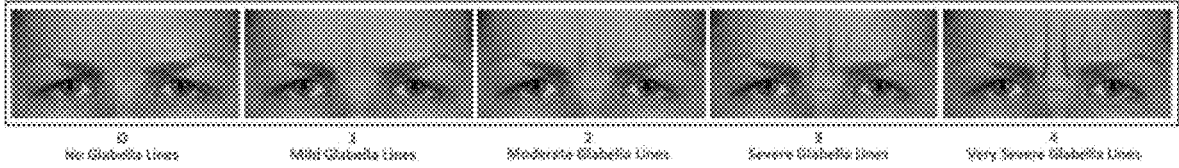

MAS Dynamic Day 14

| | 30 units | 45 units | 60 units | Placebo |
|---|---|---|---|---|
| ▦ Investigator | 87.3 | 82.5 | 91.3 | 5.9 |
| ▦ Subject | 74.5 | 72.8 | 86.4 | 7.8 |

*(Responder = 2 points reduction in GL severity, using MAS)*

Responder rate, 2-point improvement AND a score of 0 or 1, by BOTH Investigator and Subject

| QM1114-DP Composite responder rates | | | | |
|---|---|---|---|---|
| | 30 units | 45 units | 60 units | Placebo |
| Day 14 | 59% | 57% | 73% | 2% |
| Day 30 | 58% | 58% | 73% | 4% |

FIG. 5

Composite Endpoints
(N.B. GL scales are different)

| QMT114-DP PhII | | | |
|---|---|---|---|
| | 30 units | 45 units | 60 units | Placebo |
| Day 14 | 59% | 57% | 73% | 2% |
| Day 30 | 58% | 58% | 73% | 4% |

| Botox US Label Investigator Responder Rates – not composite | | |
|---|---|---|
| | Botox | Placebo |
| Day 30 | 80% | 3% |

| Dysport US Label | | |
|---|---|---|
| | Dysport | Placebo |
| Day 30 (GL-1) | 55% | 0% |
| Day 30 (GL-2) | 52% | 0% |
| Day 30 (GL-3) | 60% | 0% |

| Xeomin US Label | | |
|---|---|---|
| | Xeomin | Placebo |
| Day 30 (GL-1) | 60% | 0% |
| Day 30 (GL-2) | 48% | 0% |

*GL-1, 2 and 3 represent different PhII studies for Dysport and Xeomin, respectively*

*Within each full treatment group. Non-responders are assumed to have a duration of 0

FIG. 9A

Maximal Frown Lines

*Glabellar lines produced by maximal voluntary muscular activity contributing to the presence of the lines*

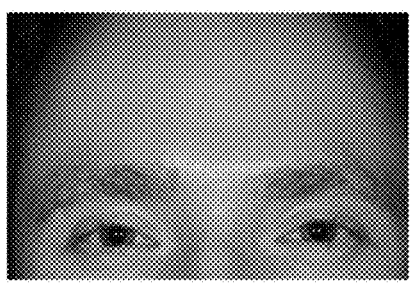

0-None

Relaxed Skin Tension Line -- no wrinkle.

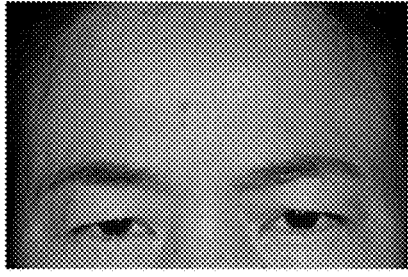

1-Mild

Glabellar depression(s) -- a mild depression(s) in the glabellar area (inter-brow space) surrounded by mild bulging of the glabellar muscles.

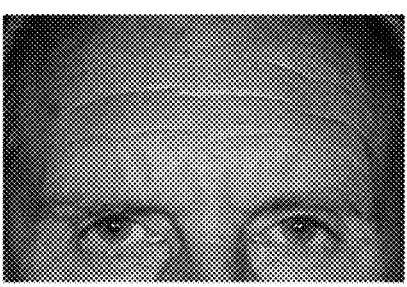

2-Moderate

Glabellar groove -- moderate depression(s) of the inter-brow space surrounded by moderate to significant muscle contraction and bulging.

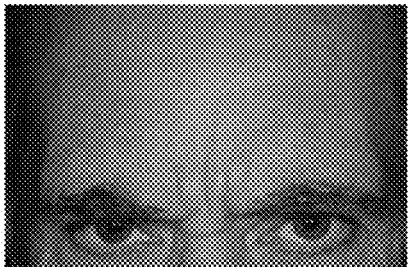

3-Severe

Glabellar furrow -- deep groove(s) in the glabellar area (inter-brow space) surrounded by profound muscle contraction and bulging

FIG. 9B

At Rest Lines

*Characterized by muscle activity at the time of evaluation having
limited impact on their presence or absence*

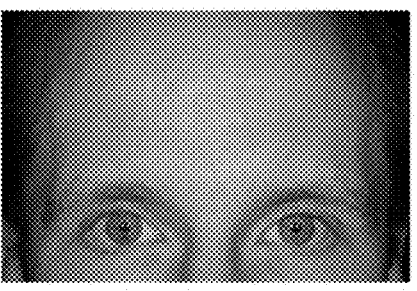

0-None

Relaxed Skin Tension Line -- no wrinkle.

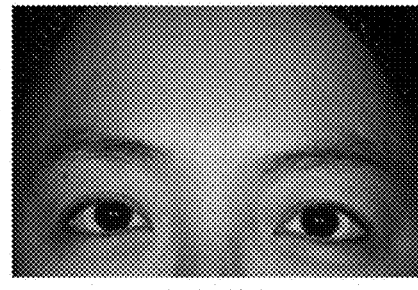

1-Mild

Fine Wrinkle -- a fine linear depression in the
skin surface clearly deeper than relaxed skin
tension lines and persistent in its presence.

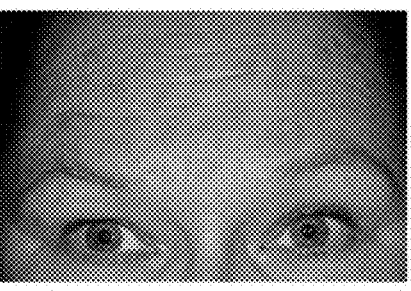

2-Moderate

Dermal crease -- a deep linear depression in the
skin surface that is deeper and/or wider than a
fine wrinkle distinguishable from a dermal groove
by the absence of muscle contractions at rest.

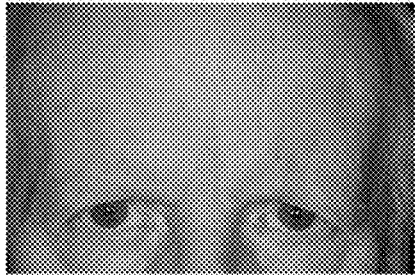

3-Severe

Dermal groove -- a deep linear depression in the
skin surface distinguishable from a dermal crease
by the presence of persistent muscle contraction
or spasm visible when the patient is "at rest."

1.  Alternative injection sites (A)       2. Alternative injection sites (B)

* the selection of injection site alternative depended on the LCL exhibited by the subject FIG. 13
(A) Maximum smile
Left LCL, Investigator's assessment
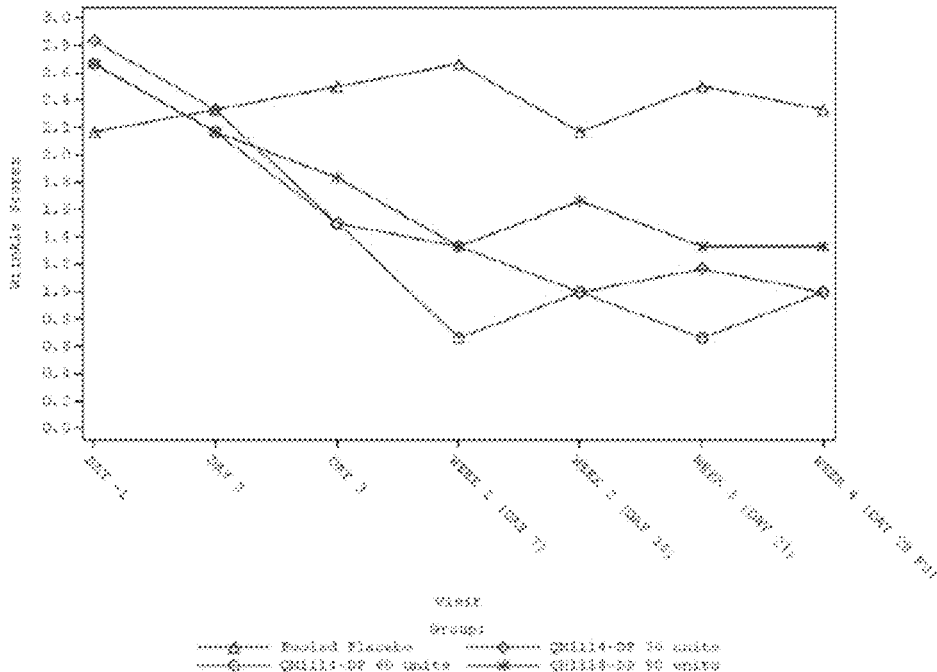
Right LCL, Investigator's assessment
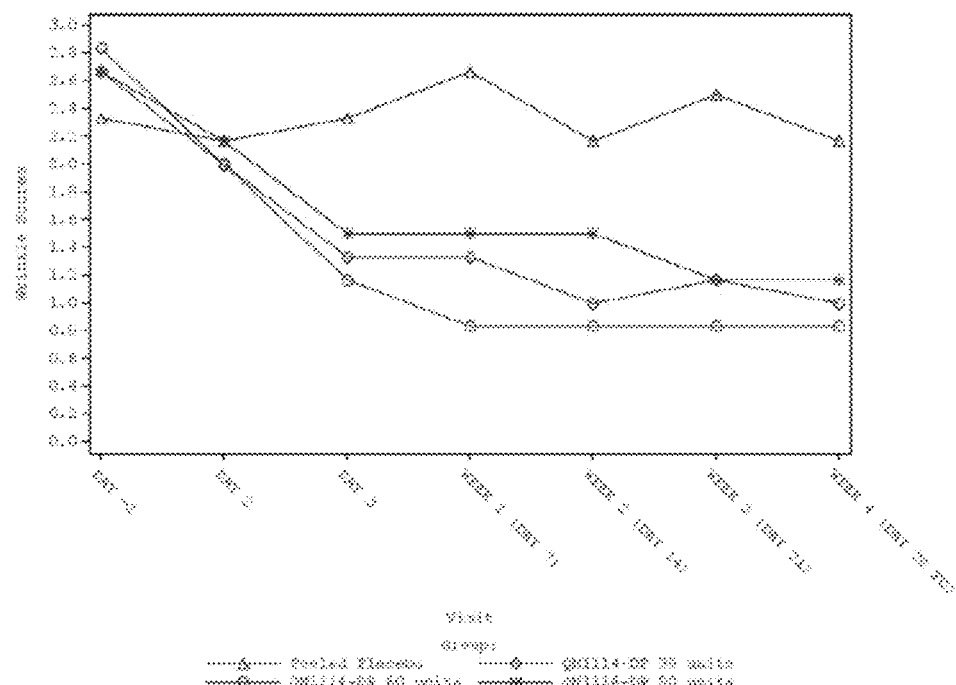

FIG. 13, CON'T
(B) Rest
Left LCL, Investigator's assessment
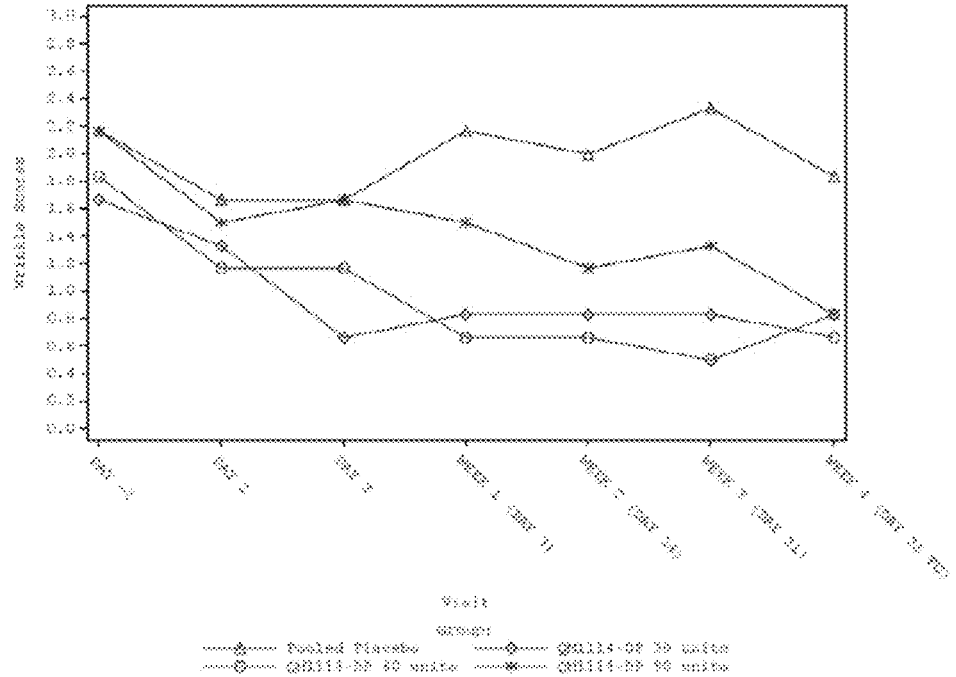
Right LCL, Investigator's assessment
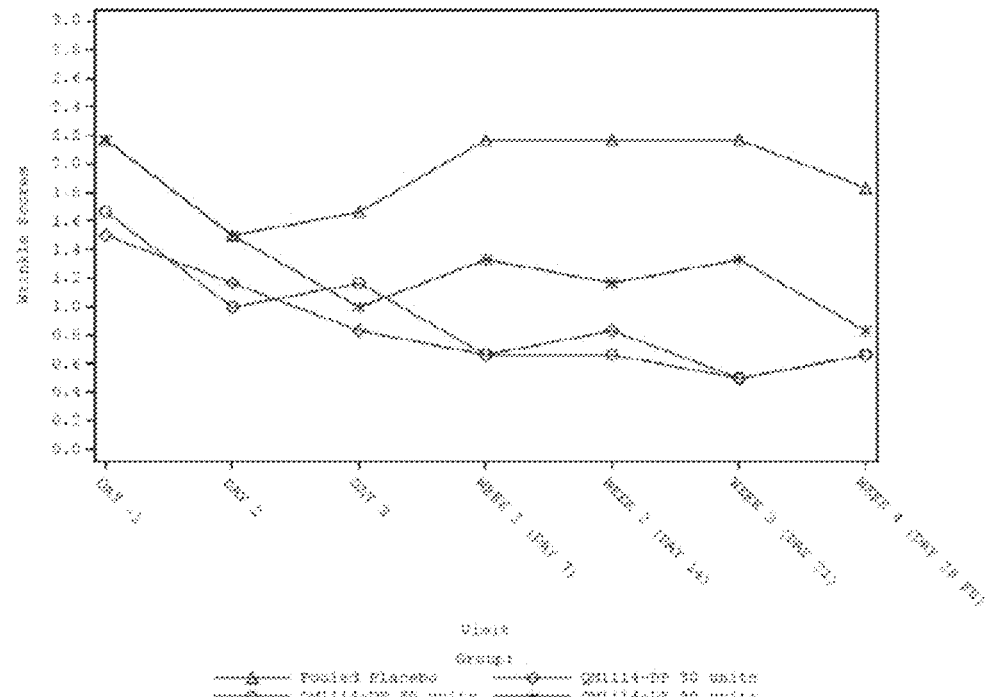

FIG. 14
(A) Maximum smile
Left LCL, Subject's assessment
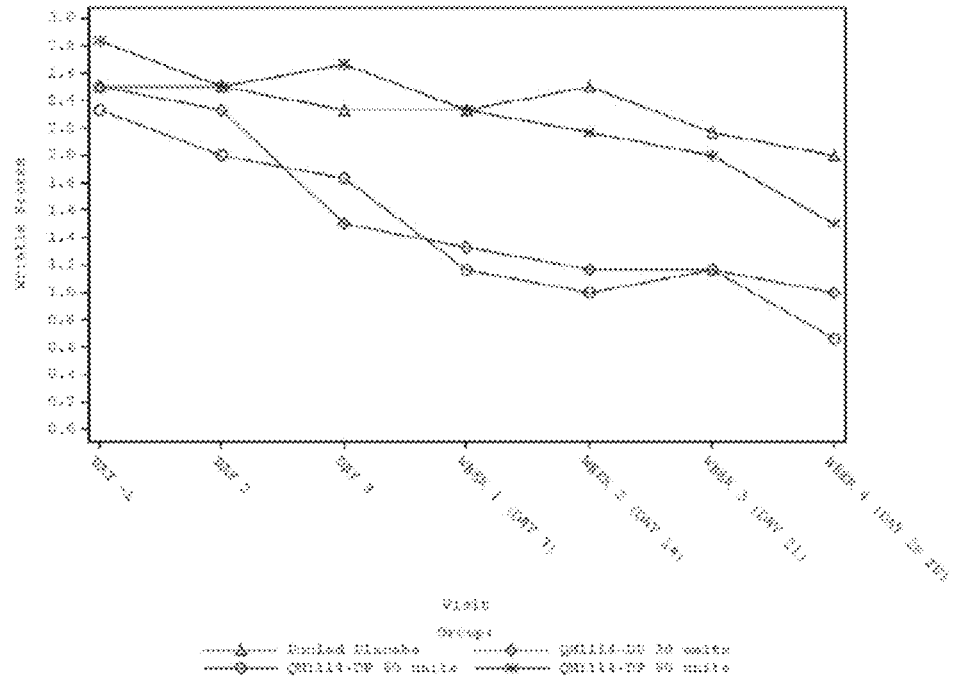
Right LCL, Subject's assessment
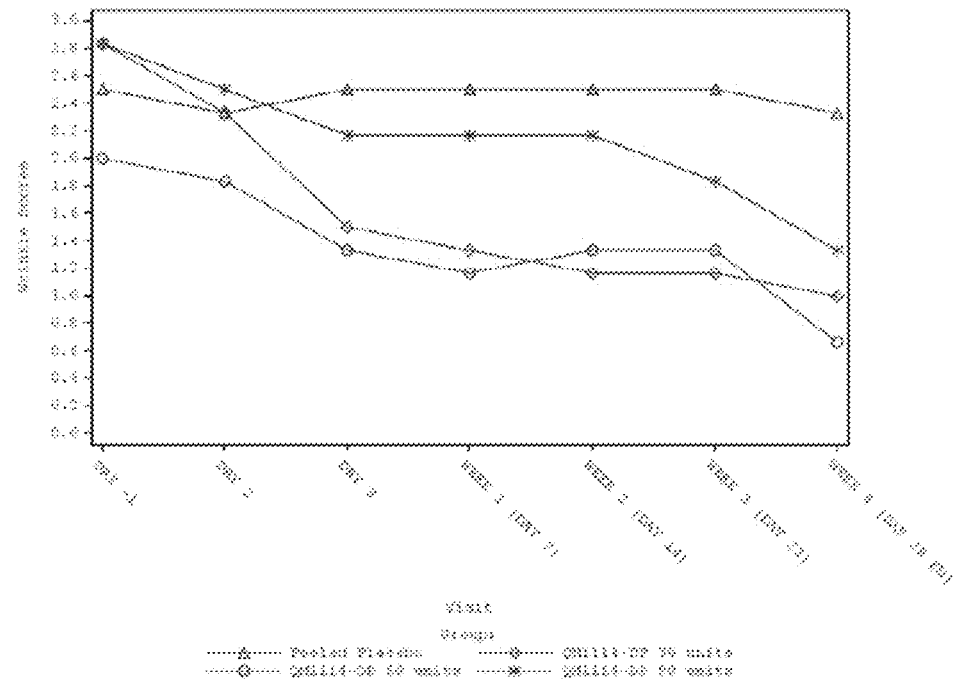

FIG. 14, CON'T
(B) Rest
Left LCL, Subject's assessment
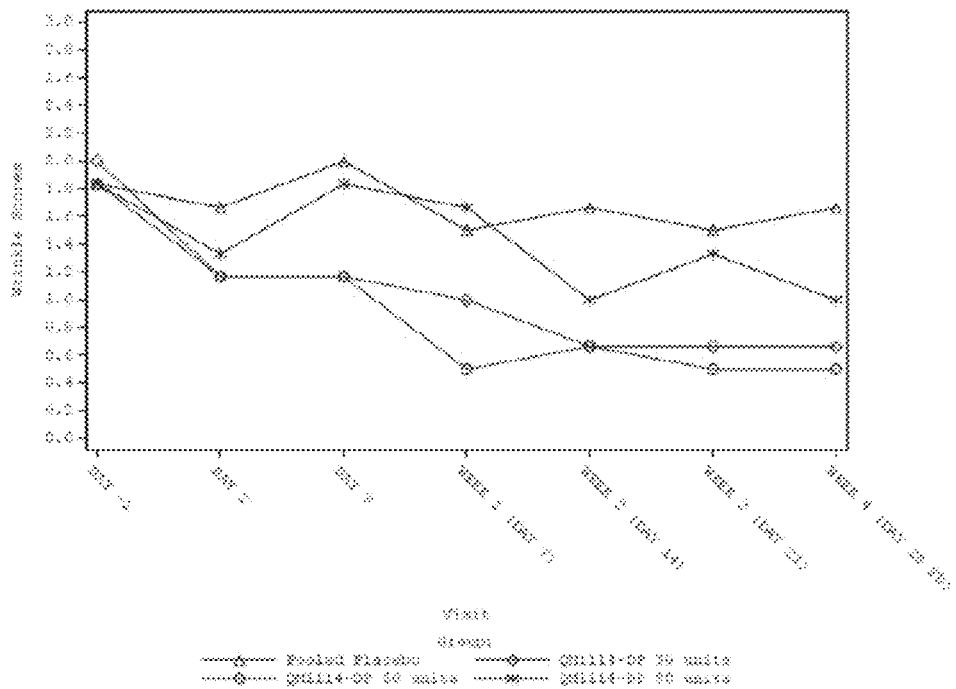
Right LCL, Subject's assessment
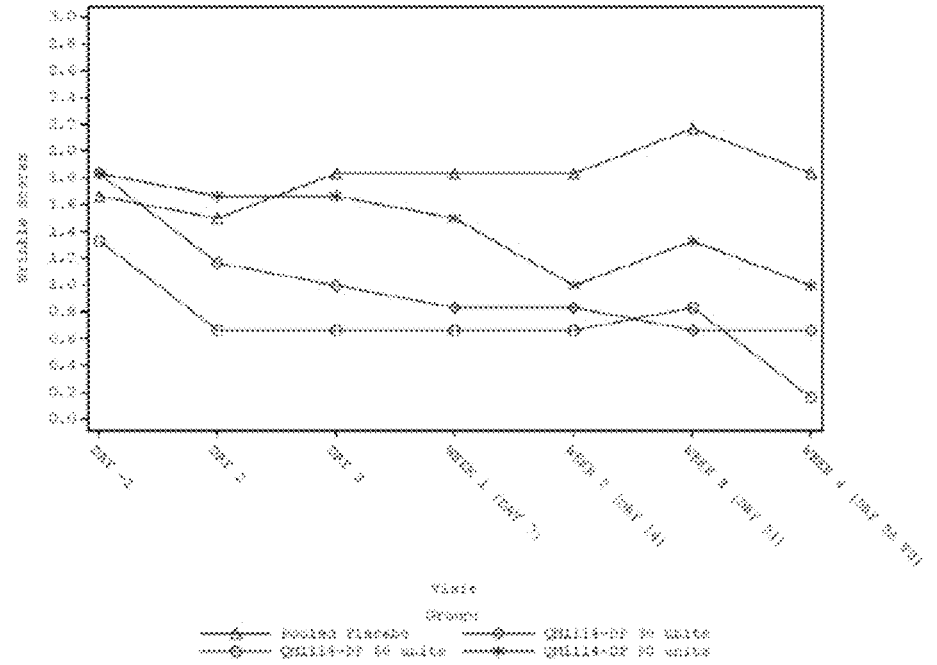

FIG. 15
(A) At maximum frown (GL indication) and maximum smile (LCL indication)
Indication: GL, maximum frown, investigator's assessment
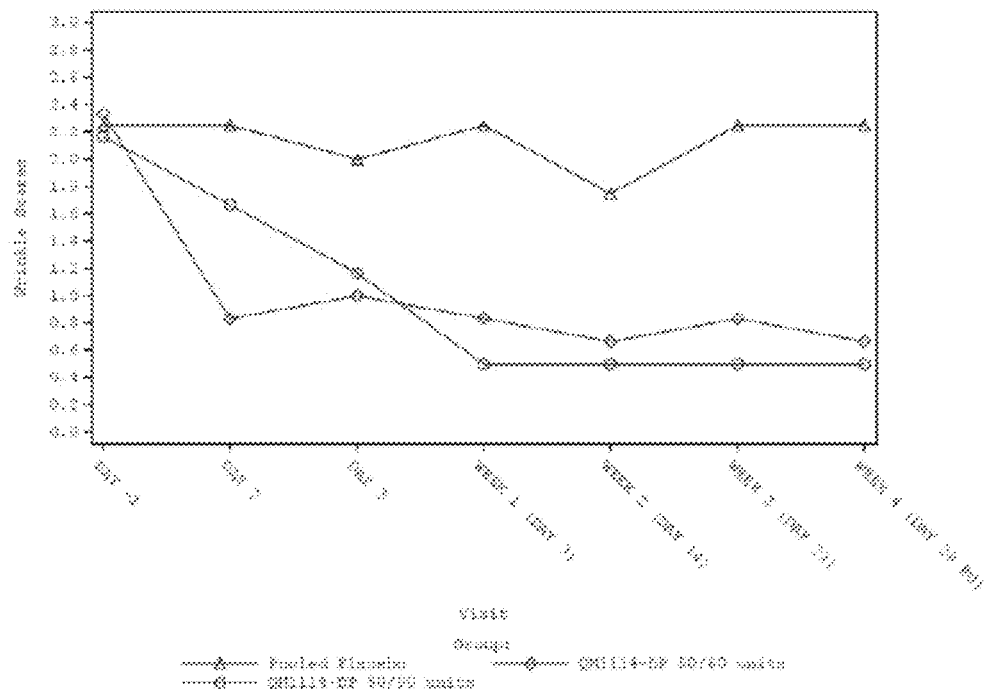
Indication: LCL (L), maximum smile, investigator's assessment
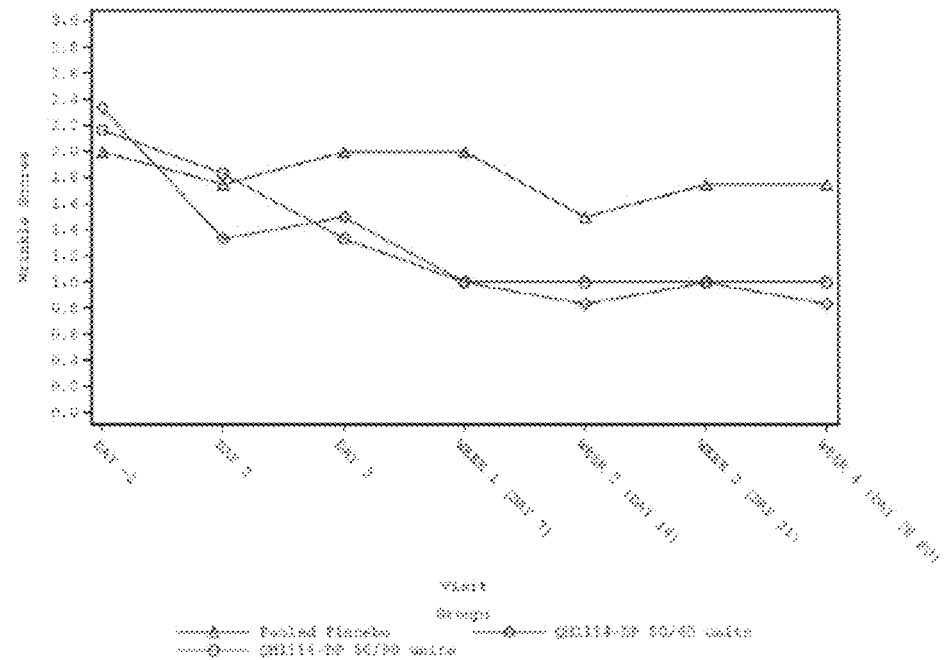

FIG. 15, CON'T
Indication: LCL (R), maximum smile, Investigator's assessment
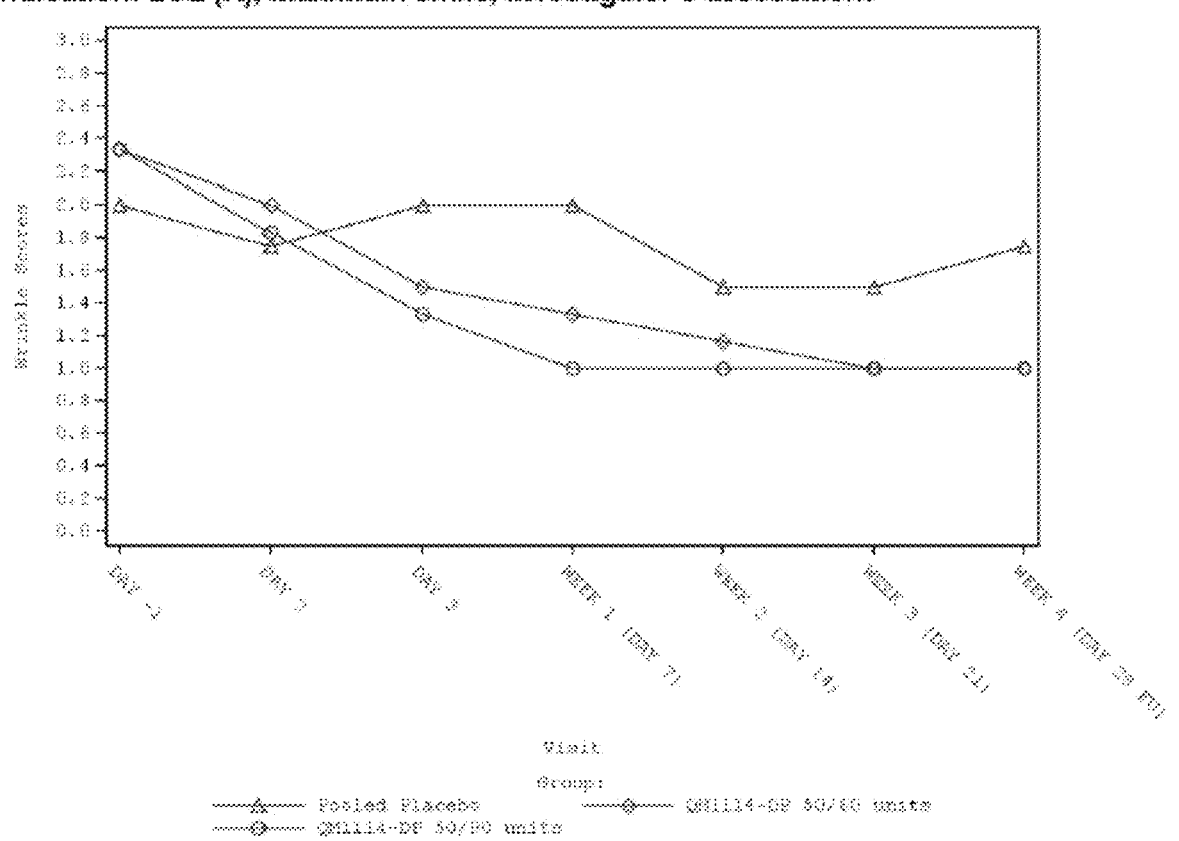

FIG. 15, CON'T
(B) Rest
Indication: GL, rest, investigator's assessment
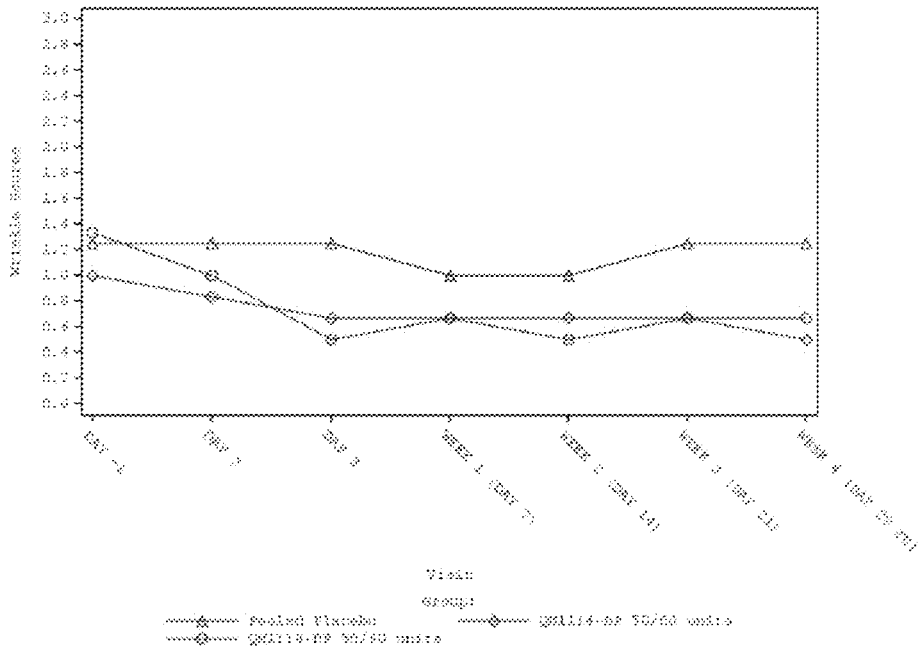
Indication: LCL (L), rest, Investigator's assessment
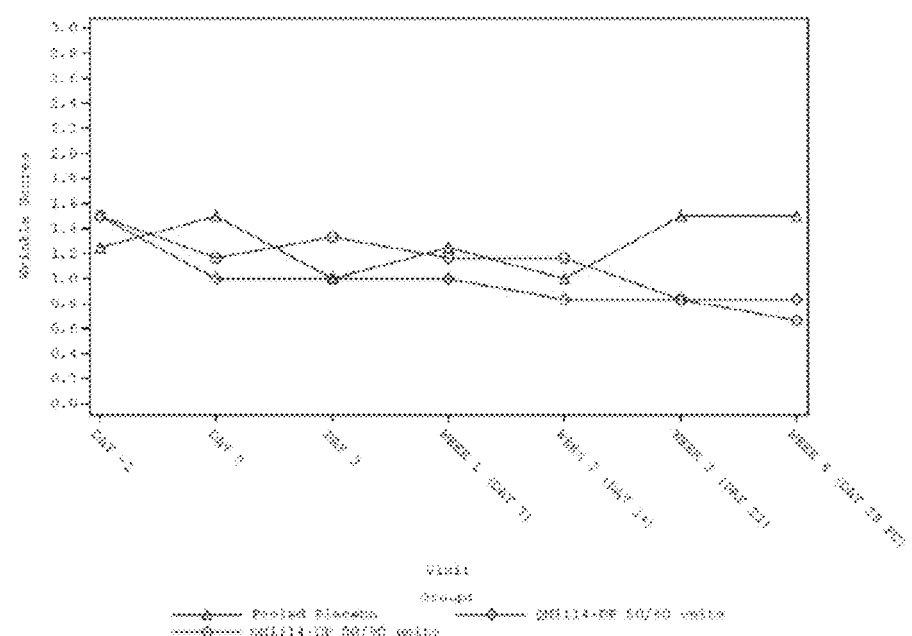

FIG. 15, CON'T
Indication: LCL (R), rest, Investigator's assessment
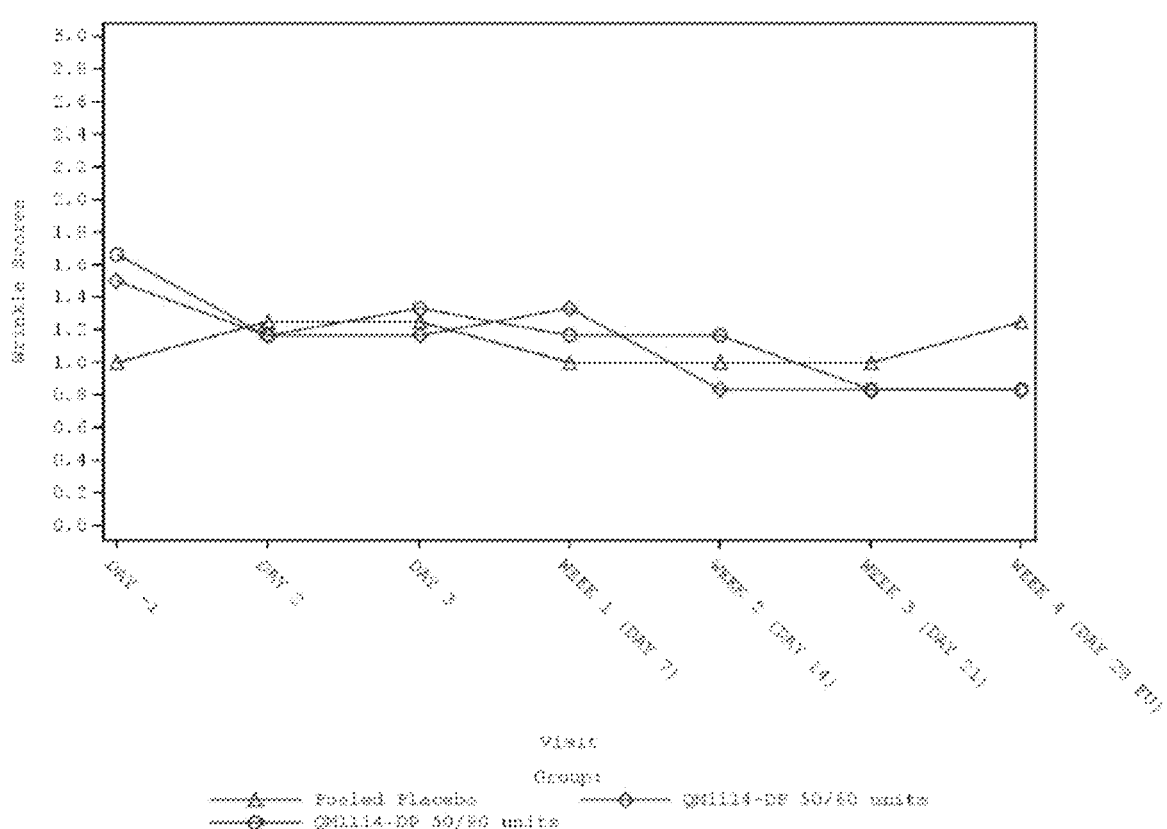

FIG. 16
(A) At maximum frown (GL indication) and maximum smile (LCL indication)
Indication: GL, maximum frown, Subject's assessment
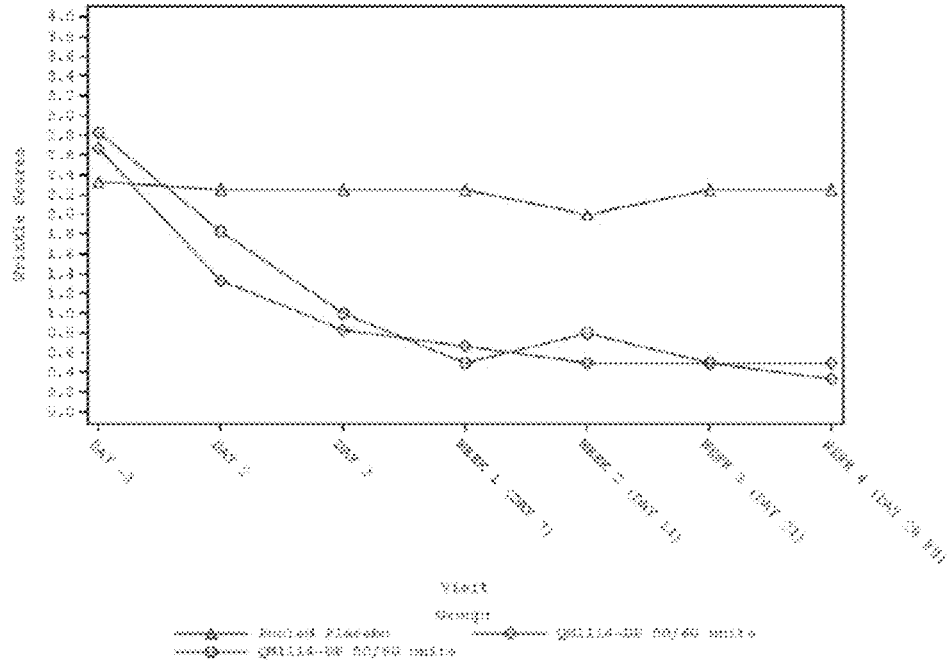
Indication: LCL (L), rest, Subject's assessment
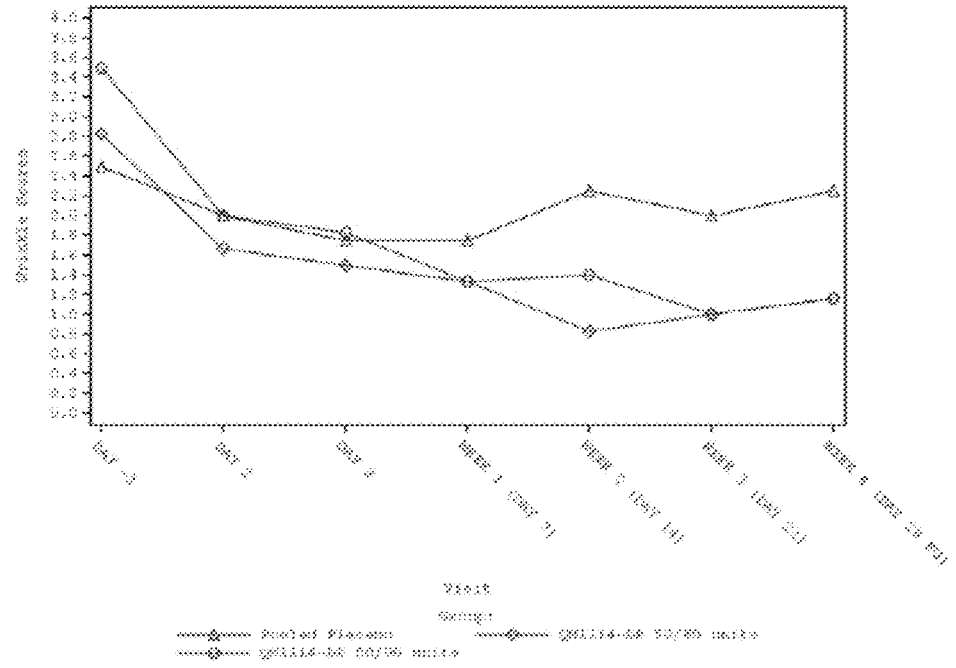

FIG. 16, CON'T
Indication: LCL (R), rest, Subject's assessment
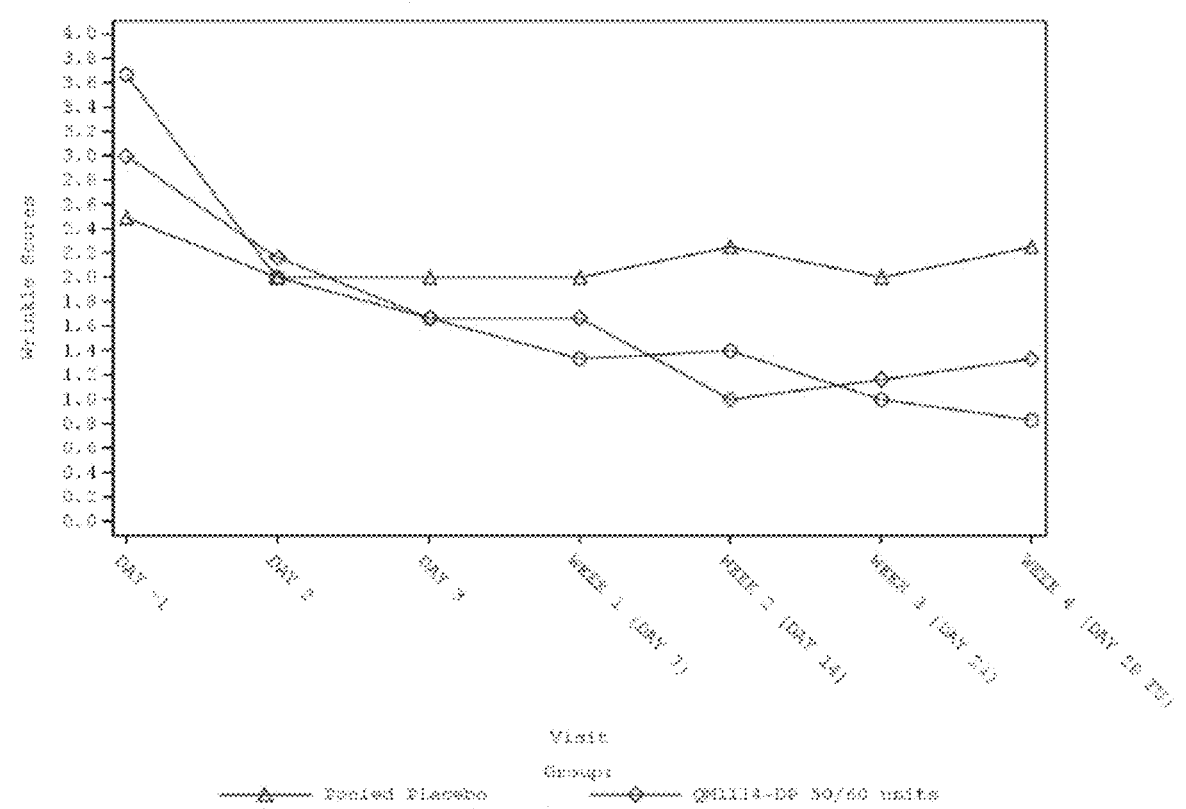

FIG. 16, CON'T
(B) Rest
Indication: GL, rest, Subject's assessment
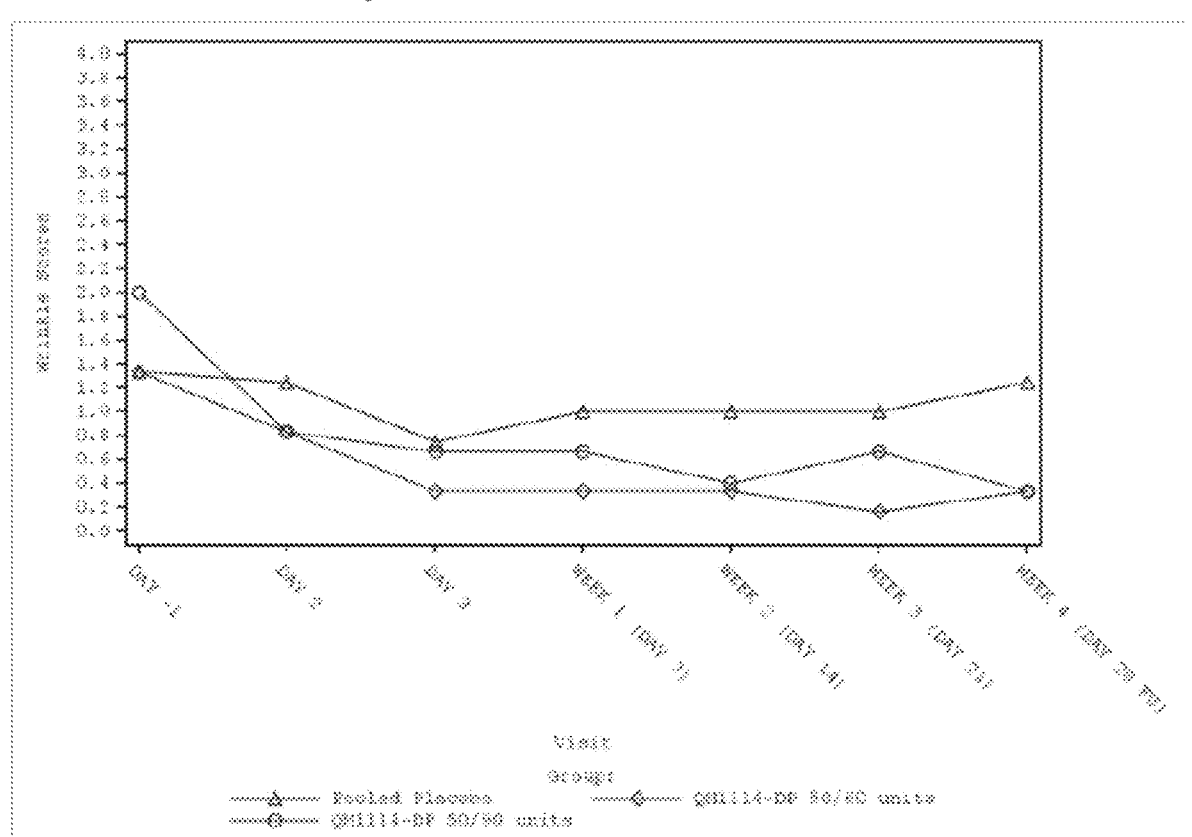

FIG. 16, CON'T
Indication: LCL (L), rest, Subject's assessment
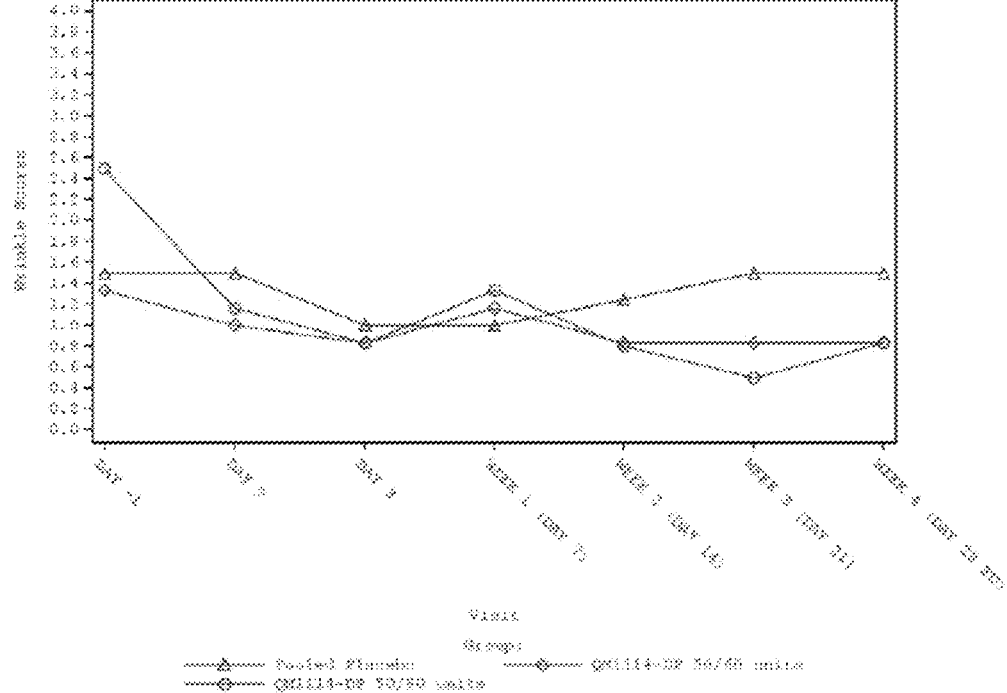
Indication: LCL (R), rest, Subject's assessment
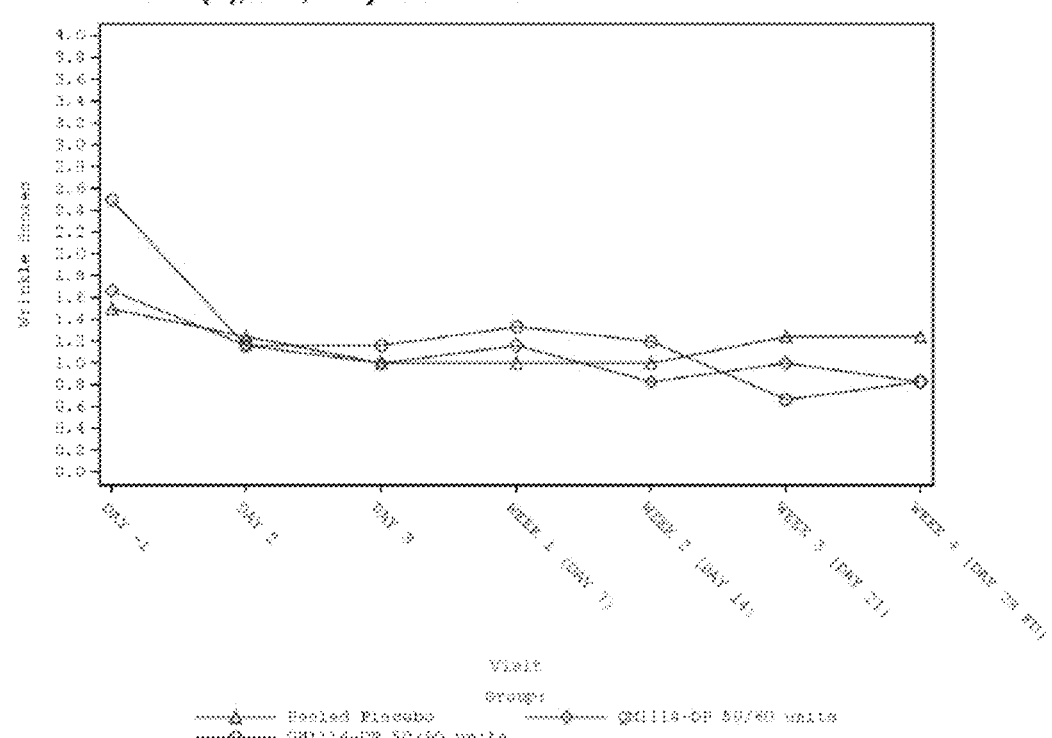

TREATMENT OF MODERATE TO VERY SEVERE GLABELLAR LINES AND LATERAL CANTHAL LINES

CROSS-REFERENCE TO RELATED APPLICATION

The present application claims priority to U.S. Provisional Application No. 62/858,766, filed Jun. 7, 2019. The benefit of priority to this prior-filed application is hereby claimed and the entire content of this application is incorporated herein by reference.

FIELD

Described herein are methods for treatment of moderate to severe and very severe glabellar lines (GL) and lateral canthal lines (LCL) using botulinum neurotoxin formulations. Also provided are liquid botulinum neurotoxin formulations.

BACKGROUND

The following description of the background of the present technology is provided simply as an aid in understanding the present technology and is not admitted to describe or constitute prior art to the present technology.

Seven generally immunologically distinct botulinum neurotoxins have been characterized—botulinum neurotoxin serotypes A, B, C, D, E, F, and G—each of which is distinguishable by neutralization with type-specific antibodies. As one example, BOTOX® is the trademark of a botulinum toxin type A (BoNT-A) purified neurotoxin complex available commercially from Allergan, Inc. (Irvine, California). BOTOX® is a popular injection-based cosmetic treatment that temporarily reduces the appearance of fine lines and wrinkles.

There are four BoNT-A products currently approved in the US for the treatment of GL (BOTOX COSMETIC®, DYS-PORT®, XEOMIN® and JEUVEAU®) in adults (BOTOX COSMETIC® and XEOMIN®) or adults under 65 years of age (DYSPORT®). All of these products are stored in lyophilized or freeze-dried form for stability reasons. Such formulations need to be reconstituted by the physician in a sterile saline solution before administration to the patient. This reconstitution step is associated with a loss of physician time, a risk of dilution error, and a risk of contamination. The botulinum toxin provider must also train the physicians in order to ensure that the reconstitution step is performed adequately.

Thus, there is currently a need for a botulinum neurotoxin formulation, preferably in liquid form that is suitable for storage and use in therapy.

SUMMARY OF THE INVENTION

The present disclosure is generally directed to compositions and methods that fulfill the need for liquid formulations of botulinum toxin that are both stable and ready to be administered without physician reconstitution or admixing.

In one aspect, the present disclosure provides liquid compositions comprising a botulinum neurotoxin and 1-5 buffering agents, at least one stabilizer, and at least one surfactant.

In another aspect, the present disclosure provides methods of treating moderate to severe glabellar lines and/or lateral canthal lines in a human subject, comprising administering a therapeutically effective amount of a liquid composition comprising a botulinum neurotoxin to the subject, thereby reducing the appearance of moderate to severe glabellar lines and/or lateral canthal lines, wherein the liquid composition further comprises 1-5 buffering agents, at least one stabilizer, and at least one surfactant.

In some embodiments, the liquid composition comprises at least 2 buffering agents, at least 3 buffering agents, or at least 4 buffering agents.

In some embodiments, the liquid composition comprises a first buffering agent, and in some embodiments, the first buffering agent is present at a concentration of about 100 to about 300 mM, or at a concentration of about 0.1-10 mg/mL.

In some embodiments, the liquid composition comprises a second buffering agent, and in some embodiments, the second buffering agent is present at a concentration of about 1 to about 25 mM, or at a concentration of about 0.1-1.0 mg/mL.

In some embodiments, the liquid composition comprises a third buffering agent, and in some embodiments, the third buffering agent is present at a concentration of about 1 to about 25 mM, or at a concentration of about 0.1-1.0 mg/mL.

In some embodiments, the liquid composition comprises a fourth buffering agent, and in some embodiments, the fourth buffering agent is present at a concentration of about 1 to about 25 mM, or at a concentration of about 0.1-1.0 mg/mL.

In some embodiments, the liquid composition comprises a fifth buffering agent, and in some embodiments, the fifth buffering agent is present at a concentration of about 1 to about 25 mM, or at a concentration of about 0.1-1.0 mg/mL.

In some embodiments, the buffering agents are selected from the group consisting of sodium chloride, potassium chloride, sodium phosphate, potassium phosphate, di-sodium hydrogen phosphate dehydrate, and sodium dihydrogen phosphate dehydrate.

In some embodiments, the at least one stabilizer is an amino acid. For example, the amino acid is selected from the group consisting of alanine, valine, leucine, isoleucine, methionine, phenylalanine, tyrosine, and tryptophan. Additionally, the amino acid may be the D isoform or the L isoform. In some embodiments, the amino acid is present at a concentration of about 0.1 to about 3.0 mg/mL.

In some embodiments, the at least one surfactant is a non-ionic surfactant (e.g., polysorbate 20 or polysorbate 80), and in some embodiments, the non-ionic surfactant is present at a concentration of about 0.01% (v/v) to about 5.0% (v/v), or at a concentration of about 0.1 to about 3.0 mg/mL.

In some embodiments, the botulinum neurotoxin is selected from the group consisting of botulinum neurotoxin types A, B, C, D, E, F and G, for example, the botulinum neurotoxin may be botulinum neurotoxin type A (i.e., BoNT-A). In some embodiments, the botulinum neurotoxin has a molecular weight of about 150 kDa.

In some embodiments, the pH of the liquid composition is between 6.6 and 6.9. In some embodiments, the osmolality of the liquid composition is between 270 mosm/kg and 310 mosm/kg.

In some embodiments, the liquid composition comprises 10 to 200 units of botulinum neurotoxin per mL, for example, in some embodiments, the liquid composition may comprise 100 units of botulinum neurotoxin per mL.

In some embodiments of the disclosed method, between 1 and 100 units of botulinum toxin is administered to the subject. In some embodiments of the disclosed method, between 10 and 75 units of botulinum toxin is administered to the subject. In some embodiments of the disclosed method, between 25 and 75 units of botulinum toxin is administered to the subject. In some embodiments of the disclosed method, 10, 25, 30, 45, 50, 60, 75, or 90 units of botulinum toxin is administered to the subject.

In some embodiments of the disclosed method, the liquid composition is administered by injection, for example, by subdermal, transdermal, intradermal or intramuscular injection. In some embodiments of the disclosed method, the subject is injected multiple times in the glabellar region. In some embodiments of the disclosed method, adjacent injections in the glabellar region are separated by about 0.5 to about 10 cm, while in some embodiments, adjacent injections are separated by about 1.5 to about 3 cm. In some embodiments of the disclosed method, the injections are in the procerus muscle and the corrugator supercillii muscles on each side of the face, while in some embodiments, the injections are first made in the procerus muscle followed by the corrugator supercillii muscles on each side of the face, moving outwards from the median. In some embodiments of the disclosed method, all the injections are about 1 cm above the upper orbital rim and internal to the mid-pupillary lines. In some embodiments of the disclosed method, all the injections are at least 1 cm above the central eyebrow or the bony supraorbital ridge. In some embodiments, the subject is injected multiple times below the lateral canthus, in the external part of the orbicularis oculi, and/or 1-2 cm from the orbital rim. In some embodiments, the subject is injected multiple times in the glabellar region and below the lateral canthus, in the external part of the orbicularis oculi, and/or 1-2 cm from the orbital rim.

In some embodiments of the disclosed method further comprise applying pressure on the upper orbital rim while injecting to minimize risks of regional effect of the botulinum neurotoxin.

In some embodiments of the disclosed method, said method is repeated at intervals from about 1 month to about 6 months to inhibit said recurrence, for example, the method may be repeated at intervals from about 3 months to about 6 months to inhibit said recurrence or the method may be repeated at intervals of about 4 months to inhibit said recurrence.

The disclosure also provides liquid formulations of botulinum neurotoxin according to any one of the foregoing embodiments for use in treating glabellar lines and/or lateral canthal lines.

The disclosure also provides uses of any of the foregoing embodiments of the liquid formulations of botulinum neurotoxin for treating glabellar lines and/or lateral canthal lines in a subject comprising administering the disclosed formulation to the subject.

The following detailed description is exemplary and explanatory, but it is not intended to be limiting.

BRIEF DESCRIPTION OF THE DRAWINGS

FIG. 1 demonstrates that Merz Aesthetic Severity (MAS) glabellar line (GL) Scale at Rest and MAS GL Scale Dynamic.

4

FIG. 5 compares the treatment by botulinum neurotoxin (QM1114-DP formulation) to currently marketed botulinum toxins in the US.

Figure 6:
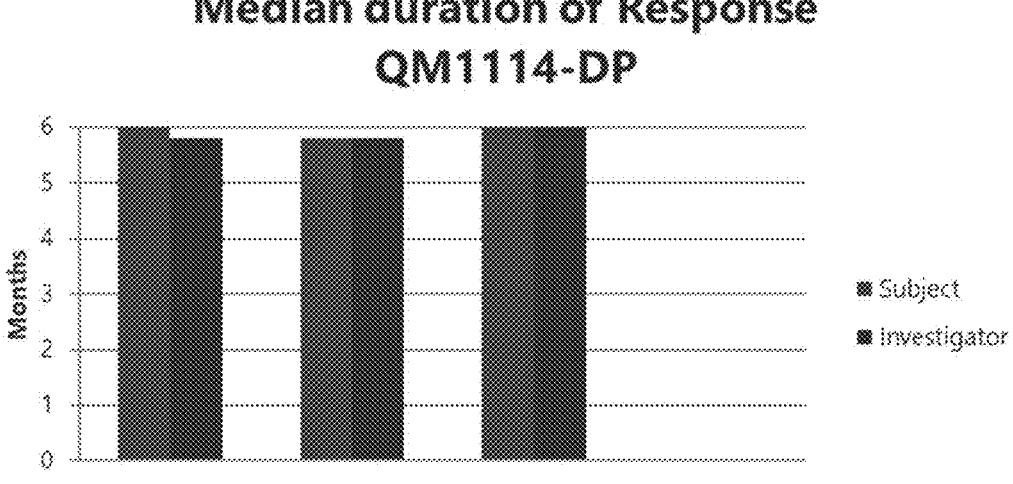

FIG. 6 demonstrate the duration of response of botulinum neurotoxin (QM1114-DP formulation) treatment. The duration of response was measured separately for the investigator and the subject assessment of GL severity using MAS Dynamic as time between the first occurrence of at least 2 points reduction and the return to the baseline score.

Figure 7:
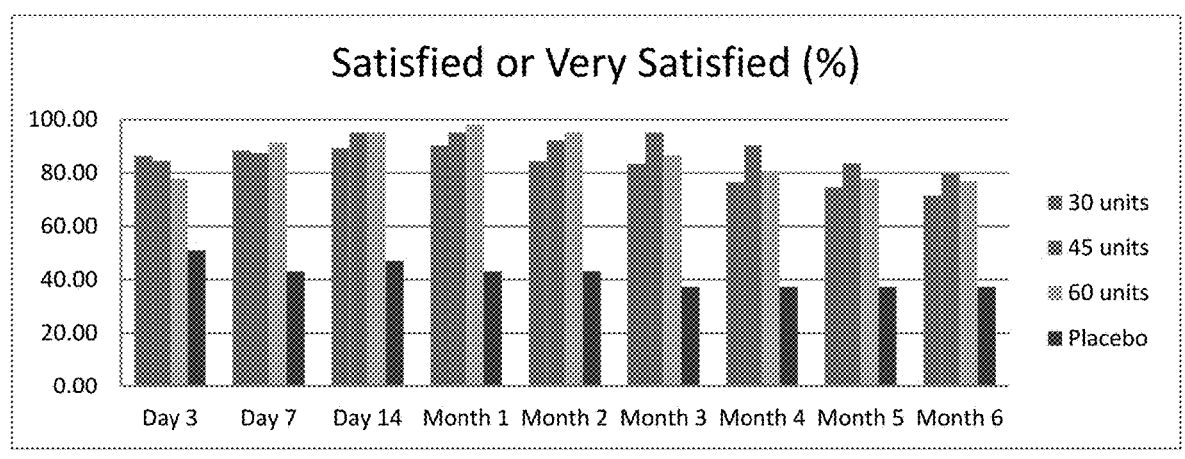

FIG. 7 shows patient satisfaction of botulinum neurotoxin (QM1114-DP formulation) treatment.

Figure 8A:
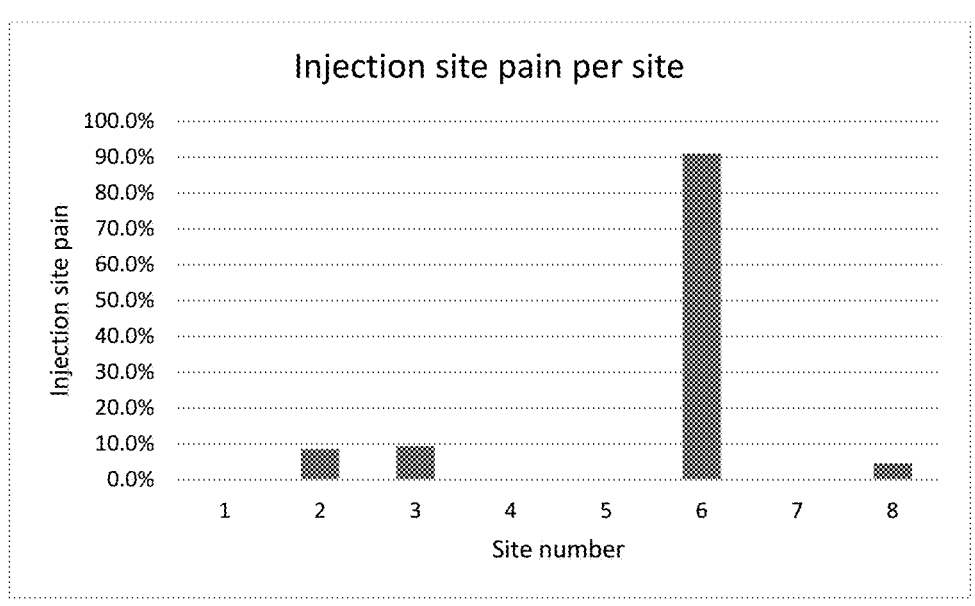
Figure 8B:
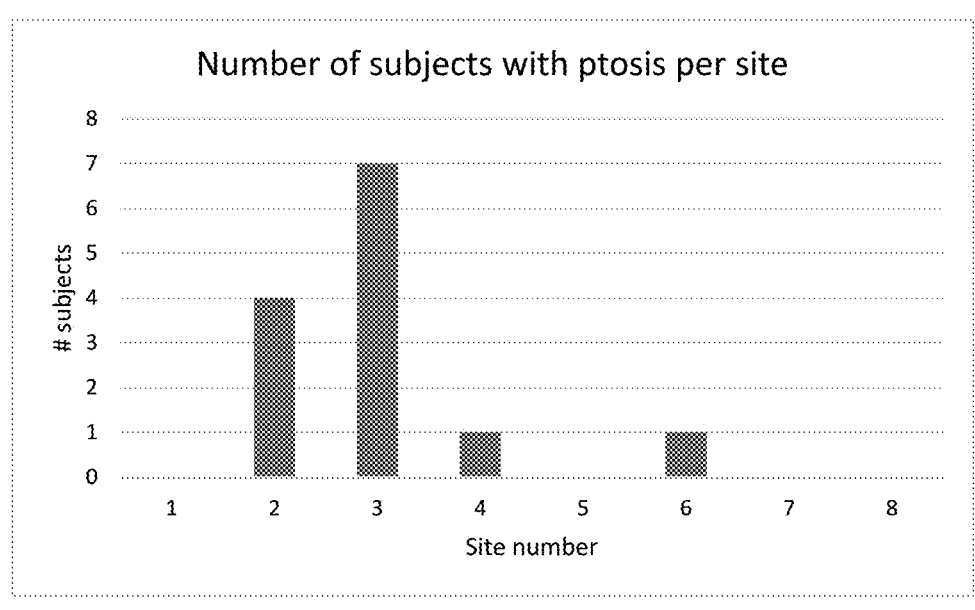

FIGS. 8A-8B show adverse events and site effects of botulinum neurotoxin treatment. FIG. 8A shows injection site pain and FIG. 8B shows the number of subject that reported ptosis.

FIGS. 9A-9B show different scores of glabellar lines under different conditions.

FIG. 9A shows a scale of glabellar lines produced by maximal voluntary muscular activity (i.e., maximal frown lines) and FIG. 9B shows glabellar lines at rest.

Figure 10:
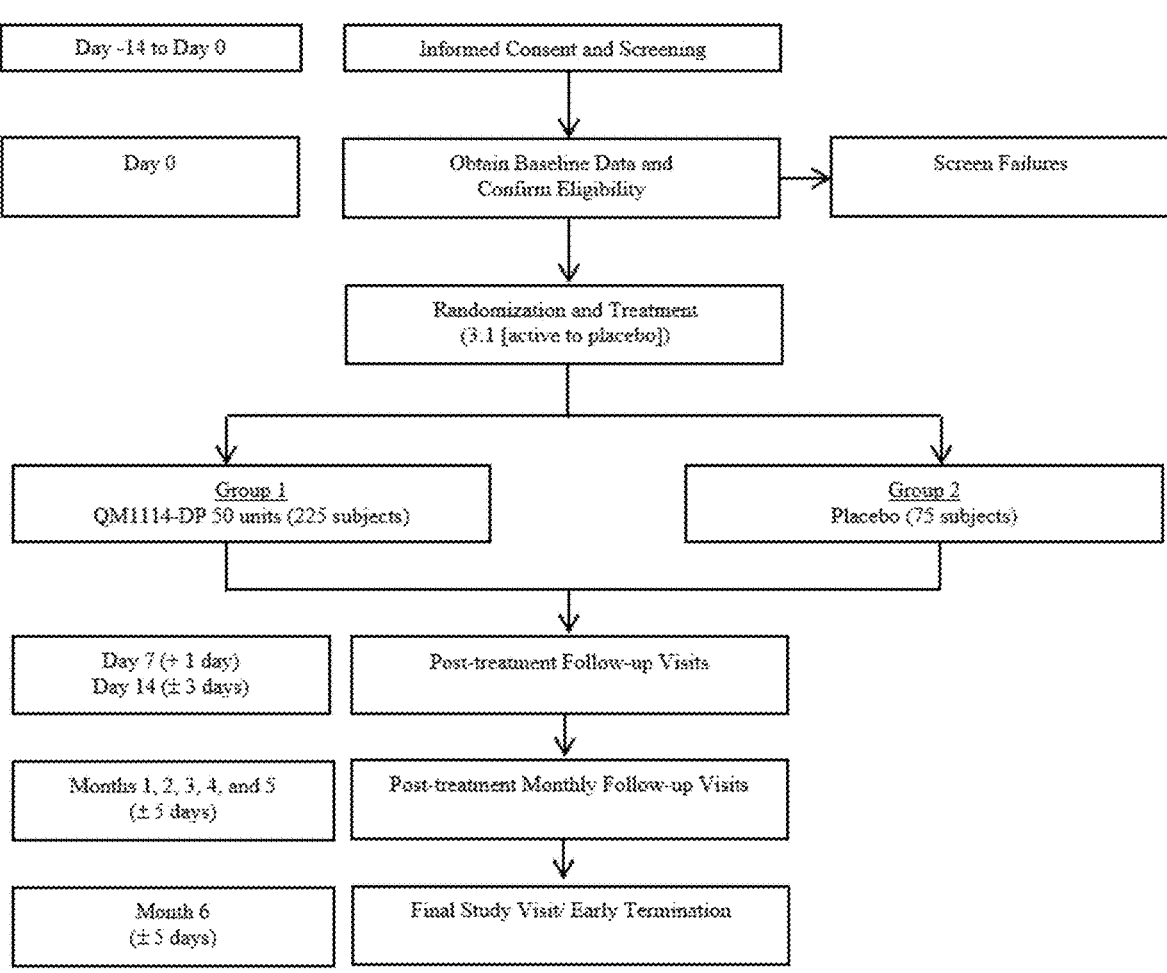

FIG. 10 shows clinical study flow chart.

Figure 11:
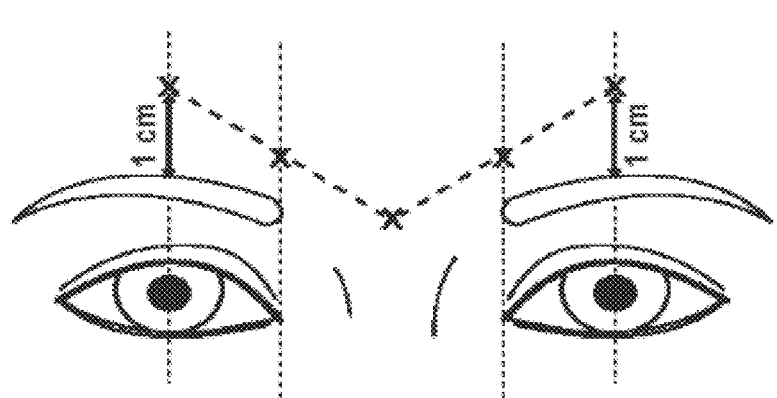

FIG. 11 shows injection sites for treating glabellar lines.

Figure 12:
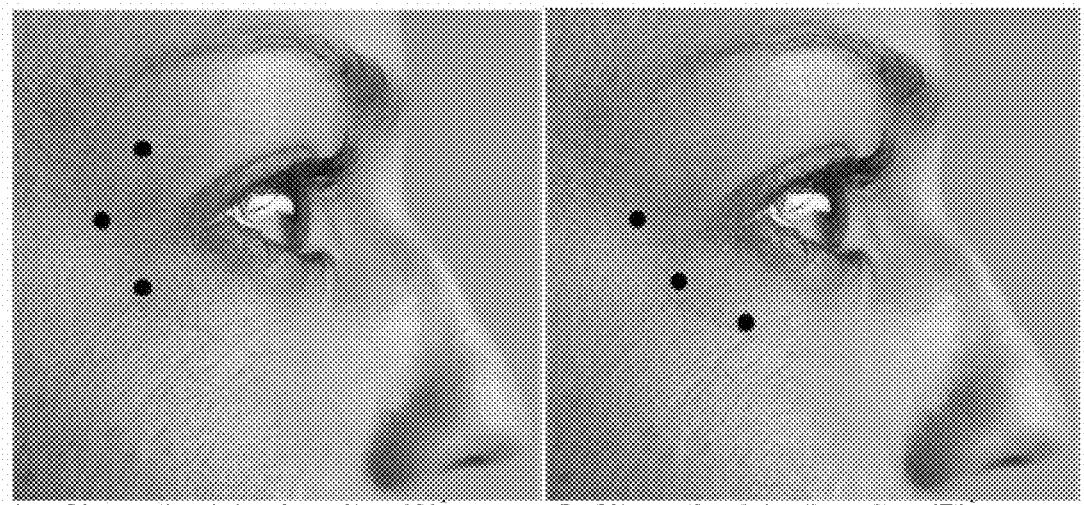

FIG. 12 shows shows injection sites for treating lateral canthal lines (LCL). The injection sites may be set as shown in (A) or (B) depending on the LCL exhibited by the subject.

FIG. 13 shows mean rhytid scores by treatment group over time (Investigator): at maximum smile (A) and at rest (B).

FIG. 14 shows mean rhytid scores by treatment group over time (Subject): at maximum smile (A) and at rest (B).

FIG. 15 shows mean rhytid scores by treatment group over time (Investigator): at maximum frown/smile (A) and at rest (B).

FIG. 16 shows mean rhytid scores by treatment group over time (Subject): at maximum frown/smile (A) and at rest (B).

DETAILED DESCRIPTION

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

I. Definitions

As used herein, the singular forms "a," "an," and "the" designate both the singular and the plural, unless expressly stated to designate the singular only.

It is to be understood, although not always explicitly stated, that all numerical designations are preceded by the term "about." The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 15%, 10%, 5%, 1%, or 0.1% of the particular term.

Also as used herein, "and/or" refers to and encompasses any and all possible combinations of one or more of the associated listed items, as well as the lack of combinations when interpreted in the alternative ("or").

The terms "administer," "administration," or "administering" as used herein refer to (1) providing, giving, dosing and/or prescribing, such as by either a health professional or his or her authorized agent or under his direction, and (2) putting into, taking or consuming, such as by a health professional or the subject. Administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule. The pharmaceutical compositions disclosed herein are "locally administered" (local administration), that is administered at or in the vicinity of the site at which a therapeutic result or outcome is desired.

The terms "treat", "treating" or "treatment", as used herein, include reducing or improving the appearance of glabellar lines (GL) and/or lateral canthal lines (LCL), or one or more symptoms thereof, whether or not GL or LCL are considered to be "cured" or "eliminated" and whether or not all symptoms are resolved. The terms also include reducing or preventing progression of GL, LCL, and/or one or more symptoms thereof, and achieving any therapeutic and/or prophylactic benefit.

The term "Botulinum toxin" means a botulinum neurotoxin type A, B, C, D, E, F or G as either pure toxin (i.e. the about 150 kiloDalton molecular weight neurotoxic component) or as a botulinum toxin complex (about 300 to about 900 kiloDaltons molecular weight), including recombinant, chimeric, hybrid, retargeted, and amino acid sequence modified botulinum neurotoxins, but excluding botulinum toxins which are not neurotoxins such as the cytotoxic botulinum toxins $C_2$ and $C_3$.

"Local administration" means administration (i.e. by a subcutaneous, intramuscular, subdermal, intradermal, subcutaneous, intra-organ, e.g. injected into the bladder wall or into the body of the prostate] or transdermal route) of a pharmaceutical agent to or to the vicinity of a target tissue, muscle or subdermal location by a non-systemic route. Thus, local administration excludes systemic (i.e. to the blood circulation system) routes of administration, such as intravenous or oral administration. Peripheral administration means administration to the periphery (i.e. to a location on or within a face, limb, trunk or head of a patient) as opposed to a visceral or gut (i.e. to the viscera) administration.

"Pharmaceutical composition" means a formulation in which an active ingredient (the active agent) can be a botulinum neurotoxin. The word "formulation" means that there is at least one additional ingredient in the pharmaceutical composition besides the active agent. A pharmaceutical composition is therefore a formulation which is suitable for diagnostic or therapeutic administration (i.e. by subdermal or intramuscular injection) to a subject, such as a human patient.

An "effective amount" is an amount sufficient to effect beneficial or desired results such as lessening, smoothing, or straightening glabellar lines and/or lateral canthal lines. An effective amount as used herein would also include an amount sufficient prevent worsening of glabellar line or lateral canthal line formation, or reverse the formation of existing glabellar lines. Thus, it is not possible to specify the exact "effective amount." An effective amount can be administered in one or more administrations, applications, or dosages. Such delivery is dependent on a number of variables including the time period for which the individual dosage unit is to be used, the location of administration of the agent, the severity of the glabellar lines, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. The dosage can be determined by a physician and adjusted, as necessary, to suit observed effects of the treatment.

II. Liquid Composition

Provided herein are liquid compositions comprising a botulinum neurotoxin and a buffer that are suitable for storage as a liquid and for treatment of glabellar lines without further reconstitution or admixing.

The botulinum neurotoxin (BoNT) is a protein dimer of 150 kilodalton (kDa) consisting of a 100 kDa heavy chain and 50 kDa light chain. The two chains are connected by a disulphide bond of two cysteine residues. The light chain is an enzyme that cuts the synaptosomal-associated protein of 25 kDa (SNAP-25). The heavy chain mediates binding and internalization of the toxin protein. Unlike other commercially available BoNTs, the botulinum neurotoxin in the present liquid composition (herein referred to as QM1114) is stable in liquid form and does not require reconstitution or admixing prior to use. In some embodiments, the BoNT formulated in the liquid composition is botulinum neurotoxin type A (BoNT-A1).

The liquid composition according to the invention comprises a buffer which comprises sodium, chloride, and/or phosphate ions. The addition of such ions usually occurs through the addition of buffering salts.

For example, the liquid composition may comprise at least one source of chloride ions, such as sodium chloride, potassium chloride, or another source of chloride ions at a concentration of about 100 to about 300 mM, such as 100, 110, 120, 130, 140, 150, 160, 170, 180, 190, 200, 210, 220, 230, 240, 250, 260, 270, 280, 290, or 300 mM, or at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM. In some embodiments, the liquid composition may comprise more than one source of chloride ions at the same or differing concentrations, for instance, sodium chloride or another source of sodium or chloride ions at a concentration of about 100 to about 300 mM, such as 100, 110, 120, 130, 140, 150, 160, 170, 180, 190, 200, 210, 220, 230, 240, 250, 260, 270, 280, 290, or 300 mM, and potassium chloride or another source of chloride ions at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM. In some embodiments, the one or more source(s) of sodium/chloride ions may be present at the same or differing concentrations in the range of about 0.1-10 mg/mL, such as 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 mg/mL or any value in between.

Similarly, the liquid composition may comprise at least one source of phosphate ions, such as sodium phosphate, potassium phosphate, di-sodium hydrogen phosphate dehydrate, sodium dihydrogen phosphate dehydrate, or another source of phosphate ions at a concentration of about 1 to about 50 mM or about 5 to about 15 mM, such as 1, 5, 10, 15, 20, 25, 30, 35, 40, 45, or 50 mM. In some embodiments, the liquid composition may comprise more than one source of phosphate ions at the same or differing concentrations, for instance, sodium phosphate, potassium phosphate, di-sodium hydrogen phosphate dehydrate, sodium dihydrogen phosphate dehydrate, or another source of phosphate ions at a concentration of about 1 to about 50 mM or about 5 to about 15 mM, such as 1, 5, 10, 15, 20, 25, 30, 35, 40, 45, or 50 mM, and a different source of phosphate ions selected from sodium phosphate, potassium phosphate, di-sodium hydrogen phosphate dehydrate, sodium dihydrogen phosphate dehydrate, or another source of phosphate ions at a concentration of about 1 to about 50 mM or about 5 to about 15 mM, such as 1, 5, 10, 15, 20, 25, 30, 35, 40, 45, or 50 mM. In some embodiments, the one or more source(s) of phosphate ions may be present at the same or differing concentrations in the range of about 0.1-1.0 mg/mL, such as 0.1, 0.2, 0.3, 0.4, 0.5, 0.6, 0.7, 0.8, 0.9, or 1.0 mg/mL or any value in between.

In some embodiments, the liquid composition may comprise 1-5 or more buffering agents. Thus, the liquid composition may comprise 1, 2, 3, 4, or 5 or more buffering agents, including but not limited to, sodium chloride, potassium chloride, sodium phosphate, potassium phosphate, di-sodium hydrogen phosphate dehydrate, or sodium dihydrogen phosphate dehydrate. The 1, 2, 3, 4, or 5 or more buffering agents may be present at the same or differing concentrations. For example, in some embodiments, a first buffering agent (e.g., sodium chloride, potassium chloride, sodium phosphate, potassium phosphate, di-sodium hydrogen phosphate dehydrate, or sodium dihydrogen phosphate dehydrate) may be present at a concentration of about 100 to about 300 mM, such as 100, 110, 120, 130, 140, 150, 160, 170, 180, 190, 200, 210, 220, 230, 240, 250, 260, 270, 280, 290, or 300 mM, or at a concentration of about 0.1-10 mg/mL, such as 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.95.05.1, 5.2, 5.3, 5.4, 5.5, 5.6, 57, 58, 59, 60, 6.1, 6.2, 6.3, 6.4, 6.5, 6.6, 6.7, 6.8, 6.9, 7.0, 7.1, 7.2, 73, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 mg/mL or any value in between. In some embodiments, a second buffering agent (e.g., sodium chloride, potassium chloride, sodium phosphate, potassium phosphate, di-sodium hydrogen phosphate dehydrate, or sodium dihydrogen phosphate dehydrate) may be present at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM, or at a concentration of about 0.1-1.0 mg/mL, such as 0.1, 0.2, 0.3, 0.4, 0.5, 0.6, 0.7, 0.8, 0.9, or 1.0 mg/mL or any value in between. In some embodiments, a third buffering agent (e.g., sodium chloride, potassium chloride, sodium phosphate, potassium phosphate, di-sodium hydrogen phosphate dehydrate, or sodium dihydrogen phosphate dehydrate) may be present at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM, or at a concentration of about 0.1-1.0 mg/mL, such as 0.1, 0.2, 0.3, 0.4, 0.5, 0.6, 0.7, 0.8, 0.9, or 1.0 mg/mL or any value in between. In some embodiments, a fourth buffering agent (e.g., sodium chloride, potassium chloride, sodium phosphate, potassium phosphate, di-sodium hydrogen phosphate dehydrate, or sodium dihydrogen phosphate dehydrate) may be present at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM, or at a concentration of about 0.1-1.0 mg/mL, such as 0.1, 0.2, 0.3, 0.4, 0.5, 0.6, 0.7, 0.8, 0.9, or 1.0 mg/mL or any value in between. In some embodiments, a fifth buffering agent (e.g., sodium chloride, potassium chloride, sodium phosphate, potassium phosphate, di-sodium hydrogen phosphate dehydrate, or sodium dihydrogen phosphate dehydrate) may be present at a concentration of about 1 to about 25 mM, such as 1, 2, 3, 4, 5, 6, 7, 8, 9, 10, 11, 12, 13, 14, 15, 16, 17, 18, 19, 20, 21, 22, 23, 24, 25 mM, or at a concentration of about 0.1-1.0 mg/mL, such as 0.1, 0.2, 0.3, 0.4, 0.5, 0.6, 0.7, 0.8, 0.9, or 1.0 mg/mL or any value in between.

Other components may be included in the liquid composition as well in order to improve stability or other properties of the composition. For example, applicable stabilizers may include, but are not limited to amino acids (e.g., alanine, valine, leucine, serine, threonine, lysine histidine, tryptophan, aspartic acid, or glutamic acid), sodium hydrogen sulfite, sodium citrate or other citrates, etc. In some embodiments, the amino acid may be an amino acid with a hydrophobic side chain (e.g., alanine, valine, leucine, isoleucine, methionine, phenylalanine, tyrosine, and tryptophan). In some embodiments, the amino acid may be in the D isoform, while in some embodiments, the amino acid may be in the L isoform Thus, in some embodiments, the liquid composition may comprise at least one D- or L-amino acid (e.g., alanine, valine, leucine, serine, threonine, lysine histidine, tryptophan, aspartic acid, or glutamic acid) at a concentration of about 0.1 to about 3.0 mg/mL, about 0.5 to about 2.5 mg/mL, or about 0.75 to about 2.25 mg/mL. In some embodiments, the liquid composition may comprise at least one D- or L-amino acid (e.g., alanine, valine, leucine, serine, threonine, lysine histidine, tryptophan, aspartic acid, or glutamic acid) at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 mg/mL or any value in between. In some embodiments, the liquid composition may comprise at least one D- or L-amino acid (e.g., alanine, valine, leucine, serine, threonine, lysine histidine, tryptophan, aspartic acid, or glutamic acid) at a concentration of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 18, about 1.9, about 2.0, about 2.1, about 2.2, about 2.3, about 2.4, about 2.5, about 2.6, about 2.7, about 2.8, about 2.9, or about 3.0 mg/m L or any value in between.

In some embodiments, the liquid composition may further comprise one or more surfactants (e.g., non-ionic surfactants like a polysorbate (e.g., polysorbate 80 or polysorbate 20) or nonoxynols; anionic surfactants like docusate, or cationic surfactants like quaternary ammonium salts). Thus, in some embodiments, the liquid composition may comprise a non-ionic surfactant, including but not limited to a polysorbate (e.g., polysorbate 80 or polysorbate 20) or a nonoxynol. In some embodiments, the liquid composition may comprise an anionic surfactant, including but not limited to docusate. In some embodiments, the liquid composition may comprise a cationic surfactant, including but not limited to a quaternary ammonium salt. In some embodiments, the surfactant may be present in a concentration of about 0.01% (v/v) to about 5.0% (v/v), about 0.05% (v/v) to about 2.5% (v/v), or about 0.1% (v/v) to about 1.5% (v/v). In some embodiments, the at least one surfactant may be present in a concentration of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 30, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% (v/v) or any value in between. In some embodiments, the at least one surfactant may be present in a concentration of about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0% (v/v) or any value in between. In some embodiments, the liquid composition may comprise at least one surfactant at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 mg/mL or any value in between. In some embodiments, the liquid composition may comprise at least one surfactant at a concentration of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 19, about 2.0, about 2.1, about 2.2, about 2.3, about 2.4, about 2.5, about 2.6, about 2.7, about 2.8, about 2.9, or about 3.0 mg/mL or any value in between.

In some embodiments, the liquid composition may further comprise one or more emulsifiers (e.g., soy lecithin), wetting agents, excipients (lactose, mannitol, glucose, microcrystal cellulose, colloidal silica, and starch, etc.), binders (hydroxypropylcellulose, polyvinylpyrrolidone, and magnesium metasilicate aluminate, etc.), disintegrator (starch, L-hydroxypropylcellulose, carboxymethylcellulose, cross-carmellose sodium, and cellulose calcium glycolate, etc.), lubricants (magnesium stearate etc.), swelling agents (hydroxypropylcellulose, hydroxypropylmethylcellulose, carbopole, carboxymethylcellulose, polyvinyl alcohol, xanthan gum, and Cyamoposis Gum, etc.), swelling adjuvants (glucose, fructose, mannitol, xylitol, erythritol, maltose, trehalose, phosphate salt, citrate, silicate, glycine, glutamate, and arginine, etc.), and/or solubilizers (polyethylene glycol, propylene glycol, etc.)

In some embodiments, the liquid composition may comprise 1-5 or more buffering agents (e.g., sodium chloride, potassium chloride, sodium phosphate, potassium phosphate, di-sodium hydrogen phosphate dehydrate, or sodium dihydrogen phosphate dehydrate): one or more stabilizers (e.g., alanine, valine, leucine, serine, threonine, lysine histidine, tryptophan, aspartic acid, or glutamic acid); and one or more surfactants (e.g., non-ionic surfactants like a polysorbate (e.g., polysorbate 80 or polysorbate 20) or nonoxynols; anionic surfactants like docusate; or cationic surfactants like quaternary ammonium salts). In some embodiments, the liquid composition may comprise: (i) a first buffering agent (e.g., sodium chloride, potassium chloride, sodium phosphate, potassium phosphate, di-sodium hydrogen phosphate dehydrate, or sodium dihydrogen phosphate dehydrate) at a concentration of about 100 to about 300 mM, or at a concentration of about 0.1-10 mg/mL; (ii) a second buffering agent (e.g., sodium chloride, potassium chloride, sodium phosphate, potassium phosphate, di-sodium hydrogen phosphate dehydrate, or sodium dihydrogen phosphate dehydrate) at a concentration of about 1 to about 25 mM, or at a concentration of about 0.1-1.0 mg/mL; (iii) a third buffering agent (e.g., sodium chloride, potassium chloride, sodium phosphate, potassium phosphate, di-sodium hydrogen phosphate dehydrate, or sodium dihydrogen phosphate dehydrate) at a concentration of about 1 to about 25 mM, or at a concentration of about 0.1-1.0 mg/mL; (iv) a fourth buffering agent (e.g., sodium chloride, potassium chloride, sodium phosphate, potassium phosphate, di-sodium hydrogen phosphate dehydrate, or sodium dihydrogen phosphate dehydrate) at a concentration of about 1 to about 25 mM, or at a concentration of about 0.1-1.0 mg/mL; (v) one or more stabilizers (e.g., alanine, valine, leucine, serine, threonine, lysine histidine, tryptophan, aspartic acid, or glutamic acid) at a concentration of about 0.1 to about 3.0 mg/mL, and (vi) one or more surfactants (e.g., non-ionic surfactants like a polysorbate (e.g., polysorbate 80 or polysorbate 20) or nonoxynols; anionic surfactants like docusate; or cationic surfactants like quaternary ammonium salts) at a concentration of about 0.05% (v/v) to about 2.5% (v/v), or at a concentration of about 0.1 to about 3.0 mg/mL In some embodiments, the stabilizer may be an amino acid, and in some embodiments, the surfactant may be a non-ionic surfactant such as a polysorbate. For the purposes of the present disclosure, it should be understood that QM1114-DP may exemplify any of the foregoing embodiments.

The liquid composition according to the invention has a pH between 5.5 and 8. According to a preferred embodiment, the pH is between 6.0 and 7.5, for example about 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5. Preferably the pH is between 6.6 and 6.9. The liquid composition preferably comprises an aqueous diluent, more preferably water, for example sterile water, water for injection, purified water, and sterile water for injection.

Preferably the liquid composition is suitable for injection to a patient, in particular a human patient. The quantity of botulinum neurotoxin is commonly expressed in mouse LD50 (lethal dose 50) units, defined as the median lethal intraperitoneal dose in mice. The mouse LD50 (MLD50) unit for botulinum toxins is not a standardized unit. Indeed, assays used by different manufacturers of marketed toxins differ in particular in the choice of dilution buffer. For example the test used for DYSPORT® uses gelatine phosphate buffer, whereas the assay used for BOTOX® uses saline as a diluent. It is believed that gelatine buffers protect the toxin at the high dilutions used in LD50 assays. In contrast the use of saline as a diluent is thought to lead to some loss of potency. This could explain why when tested with the DYSPORT™ assay, one BOTOX® unit is equivalent to approximately three units of DYSPORT® (Straughan, D. W., 2006, AT LA 34(3), 305-313; Hambleton and Pickett, Hambleton, P., and A. M Pickett., 1994, Journal of the Royal Society of Medicine 87.11:719).

Preferably, the dilution buffer used to determine the mouse LD50 is a gelatine phosphate buffer. For example, the mouse LD50 can be determined as described in Hambleton, P. et al. Production, purification and toxoiding of *Clostridium botulinum* type A toxin. Eds. G. E. Jr Lewis, and P. S. Angel. Academic Press, Inc., New York, USA, 1981, p. 248 Briefly, botulinum toxin samples are serially diluted in 0.2% (w/v) gelatine 0.07M Na2HP04 buffer at pH 6.5. Groups of mice (e.g., 4 to 8 mice per group) weighing about 20 g are injected intraperitoneally with a sample of diluted toxin (for example 0.5 ml per animal). Dilution groups, for example 5 dilution groups, are selected to span the 50% lethality dose. The mice are observed for up to 96 hours and the mouse lethal dose 50 (MLD50) is estimated.

The liquid composition according to the invention preferably comprises from 4 to 10000 LD50 units of botulinum neurotoxin per mL, more preferably from 10 to 200 LD50 units of botulinum neurotoxin per mL, for example 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 LD50 units of botulinum neurotoxin per mL. The quantity of botulinum neurotoxin can also be expressed in ng.

The liquid composition according to the present invention has osmolality of 200-400 mosm/kg, and preferably from 270-310 mosm/kg, for example, 270, 275, 280, 285, 290, 295, 300, 305, or 310 mosm/kg or any value in between.

III. Treatment

Also provided herein are methods of treating moderate to severe glabellar lines and/or lateral canthal lines in a human subject, comprising administering a therapeutically effective amount of a liquid composition comprising a botulinum neurotoxin to the subject, thereby reducing the appearance of moderate to severe glabellar lines. The liquid composition may correspond to any of the foregoing embodiments disclosed in Section II supra.

In some embodiments, between 1 and 100 units of botulinum toxin is administered to the subject. In some embodiments, between 10 and 75 units of botulinum toxin is administered to the subject. In some embodiments, between 25 and 75 units of botulinum toxin is administered to the subject. In some embodiments, 10, 15, 20, 25, 30, 35, 40, 45, 50, 55, 60, 65, 70, 75, 80, 85, 90, 95, or 100 units of botulinum toxin is administered to the subject. In some embodiments, between 50 and 250 units of botulinum toxin is administered to the subject. In some embodiments, between 75 and 200 units of botulinum toxin is administered to the subject. In some embodiments, the concentration of the liquid composition being administered to the subject is between 1 and 300 units of botulinum toxin/mL, such as 1, 5, 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 210, 215, 220, 225, 230, 235, 240, 245, 250, 255, 260, 265, 270, 275, 280, 285, 290, 295, or 300 units/mL.

In some embodiments, the composition is administered by injection. In some embodiments, the injection is subdermal, transdermal, intradermal or intramuscular. In some embodiments, the method comprises multiple injections in the glabellar region. In some embodiments, the sites of adjacent injections are separated by about 0.5 to 10 cm. In some embodiments, the sites of adjacent injections are separated by about 1.5 to 3 cm.

In some embodiments, the injections are in the procerus muscle and the corrugator supercillii muscles on each side of the face, and in some embodiments, the injections are performed in a particular order, for example, starting in the procerus muscle followed by corrugator supercillii muscles on each side of the face, moving outwards from the median. In some embodiments, all the injections are about 1 cm above the upper orbital rim and internal to the mid-pupillary lines.

In some embodiments, the method further comprises applying pressure on the upper orbital rim while injecting to minimize risks of regional effect of the neurotoxin.

In some embodiments, all the injections are at least 1 cm above the central eyebrow or the bony supraorbital ridge.

In some embodiments, the composition may be administered to treat, prevent, or improve lateral canthal lines (LCL). In some embodiments, the treatment may include about three injections (one injection per injection site). For example, the treatment may include 1, 2, 3, 4, or 5 injections. The position of the injections may adjusted in accordance with the LCL pattern of rhytids for the individual subject. Depending on the pattern of rhytids for individual subjects, if the lines in the LCL region were above and below the lateral canthus, injections were administered as described in FIG. 12A, for examples. Alternatively, if the lines in the LCL for the individual subject were primarily below the lateral canthus, injections were administered as described in FIG. 12B, for example. In some embodiments, the injection points may be at the external part of the orbicularis oculi and, when applicable, at about 1-2 cm from the orbital rim. Some embodiments may comprise three injections of equal volume (100 µl) administered to each side of the face (i.e., six injections total).

In some embodiments, the composition may be administered to treat, prevent, or improve GL and LCL concurrently (i.e., at the same time). In some embodiments, treatment may include, for example, 11 injections (one injection per injection site) of equal volume (100 µl) administered to the GL area (five injections) and LCL area (three injections to each side of the face). In some embodiments, the concurrent treatment of GL and LCL may comprise 5, 6, 7, 8, 9, 10, 11, 12, 13, or 14 or more injections. For example, for GL, the five injection sites may include two injections in each corrugator supercilii muscle, and one injection in the procerus muscle, and for LCL, the position of the injections may adjusted in accordance with the LCL pattern of rhytids for the individual subject. Depending on the pattern of rhytids for individual subjects, if the lines in the LCL region were above and below the lateral canthus, injections may be administered as described in FIG. 12A.

Alternatively, if the lines in the LCL for the individual subject were primarily below the lateral canthus, injections may be administered as described in FIG. 12B. In some embodiments, the injection points for treating LCL may be at the external part of the orbicularis oculi and, when applicable, at about 1-2 cm from the orbital rim.

In some embodiments, the method is repeated at intervals from about 3 months to about 6 months to inhibit said recurrence. In some embodiments, the method is repeated at intervals of about 4 months to inhibit said recurrence.

The method provided herein results in a temporary reduction in the appearance of glabellar lines and/or lateral canthal lines in the subject. The efficacy of the treatment can be assessed by methods known to those skilled in the art. The exemplary assessment methods are provided below and in the Examples.

a. 4-Point Photographic Scale of Glabellar Line Severity: Investigator Live Assessment (GL-ILA)

The validated 4-point Photographic Scale of Glabellar Line Severity includes two grading systems: one for Investigator live assessments at maximum frown, and one for Investigator live assessments at rest. The scale represents the severity of glabellar lines from none (grade 0), mild (grade 1), moderate (grade 2) to severe glabellar lines (grade 3). Each grade is also depicted by an individual photograph and a descriptive text. The Investigators will be trained on the use of the 4-point Photographic Scale. The Investigators will use the 4-point Photographic Scale for direct, live comparison with the subject's face at screening, baseline (prior to treatment), and at all post-treatment visits. Subjects will make their assessment of glabellar line severity independently of the Investigator's assessment. Subjects will be asked to evaluate their glabellar lines at maximum frown at screening, baseline (prior to treatment), and at all post-treatment visits using the Static 4-Point Categorical Scale.

| Grade | Severity of Glabellar Lines | Description |
| --- | --- | --- |
| 0 | No wrinkles | Smooth skin |
| 1 | Mild wrinkles | Fairly smooth skin |
| 2 | Moderate wrinkles | Frown lines |
| 3 | Severe wrinkles | Deep frown lines | b. Global Aesthetic Improvement Scale (GAIS)

Subjects will rate the global aesthetic improvement of their glabellar lines at maximum frown, relative to their pre-treatment appearance, using the following categorical scale at all post-treatment visits.

| Rating |
| --- |
| Very Much Improved |
| Much Improved |

-continued

| Rating |
| --- |
| Improved |
| No Change |
| Worse |
| Much Worse |
| Very Much Worse |

Subjects will be asked: "How would you rate the change in appearance of your glabellar lines (lines between your eyebrows) at maximum frown compared with immediately before the injection?"

Subjects will be instructed to select the one rating that best describes the degree to which the appearance of their glabellar lines at maximum frown have changed relative to baseline. The subject may review the baseline photograph to aid in the assessment.

c. Diary Card

Subjects will be asked to record their assessment of study treatment response in a diary card starting the day after treatment (Day 1) through day 7 (study visit 3). They will be asked to respond "yes" or "no" to the following question: "Since being injected have you noticed an improvement in the appearance of your glabellar lines (lines between your eyebrows)?" Subjects are to complete the diary card daily and return the diary to study center at the Day 7 visit.

d. FACE-Q

The FACE-Q is a patient-reported outcome instrument to evaluate the experience and outcomes of aesthetic facial procedures from the subject's perspective. FACE-Q is composed of over 40 scales, covering four domains (Satisfaction with Facial Appearance, Health Related Quality of Life, Adverse Effects, and Process of Care). Each domain has one or more independently functioning scale(s). For the purpose of this study and given the condition treated, the Psychological Function scale has been selected to be completed by the subjects at the time points indicated in the Schedule of Assessments.

e. Facial Lines Treatment Satisfaction Questionnaire

These questions ask the subject to think about the area of the face that was treated with their most recent procedure. The subjects select a response that best matches how much they agree with a given statement. An exemplary questionnaire is provided below. Only one response for each question.

| | Thinking about the area of my face that was treated with my most recent procedure . . . | Strongly disagree | Disagree | Agree | Strongly agree |
| --- | --- | --- | --- | --- | --- |
| 1 | I would have this treatment done again | 1 | 2 | 3 | 4 |
| 2 | I would recommend this treatment to others | 1 | 2 | 3 | 4 |
| 3 | Treatment results are what I expected | 1 | 2 | 3 | 4 |
| 4 | I feel like this is the right treatment choice for me | 1 | 2 | 3 | 4 |
| 5 | I am happy with the results of my treatment | 1 | 2 | 3 | 4 |
| 6 | I feel comfortable with how my face looks when I laugh | 1 | 2 | 3 | 4 |
| 7 | I feel comfortable with how my face looks when I smile | 1 | 2 | 3 | 4 |
| 8 | My face expresses my emotions | 1 | 2 | 3 | 4 |
| 9 | I fell comfortable with how my face looks when I | 1 | 2 | 3 | 4 |

-continued

| Thinking about the area of my face that was treated with my most recent procedure . . . | Strongly disagree | Disagree | Agree | Strongly agree |
|---|---|---|---|---|
| express emotions | | | | |
| 10 My facial lines aren't very visible | 1 | 2 | 3 | 4 |
| 11 My facial lines are minimized | 1 | 2 | 3 | 4 |
| 12 I look youthful | 1 | 2 | 3 | 4 |
| 13 I have a natural look | 1 | 2 | 3 | 4 |
| 14 I look great for my age | 1 | 2 | 3 | 4 |
| 15 I look beautiful | 1 | 2 | 3 | 4 |
| 16 I look relaxed | 1 | 2 | 3 | 4 |
| 17 I look attractive | 1 | 2 | 3 | 4 |
| 18 I look well-rested | 1 | 2 | 3 | 4 |
| 19 I look renewed | 1 | 2 | 3 | 4 |
| Overall, thinking about the area of my face that was treated with my most recent procedure . . . | | | | |
| 20 I am satisfied with the outcome of my treatment | 1 | 2 | 3 | 4 |
| 21 I am satisfied with the improvement in my facial lines | 1 | 2 | 3 | 4 | f. Satisfaction with Lines (SWL) Questionnaire

At baseline (prior to treatment) and at all post-treatment visits, subjects will be asked to complete the validated SWL Questionnaire, developed by Galderma.

g. Independent Photographic Reviewer (PR)

Three IPRs, blinded to the subject's randomized treatment, will perform photographic assessments of each subject's GL at maximum frown using the validated 4-point Photographic Scale of Glabellar Line Severity. IPR assessment is performed at the end of the study for all subjects. The IPRs will use the scale for comparison with photographs of each subject's GL at maximum frown at baseline and each post-treatment visit. The IPR score is determined as the median of the scores of the three reviewers. The IPRs are not involved in any other aspect of the study.

EXAMPLES

Example 1 Treatment of Moderate to Very Severe Glabellar Lines (GL)

Multicenter, randomized, double-blind, placebo-controlled studies were conducted to evaluate different doses of botulinum neurotoxin for treatment of moderate to severe upper facial wrinkles, including glabellar lines (GL), lateral canthal lines (LCL), and GL/LCL combo. GL patients were treated with 4 dosages (10, 25, 50 and 75 units). LCL patients were treated with 3 dosages (30, 60 and 90 units). GL/LCL combo patients were treated with 2 dosages (50/60 and 50/90 units).

Phase 1 study was conducted to investigate the safety and tolerability of the treatment. There were no severe adverse events (SAEs) in this study and no subject withdrawals due to AEs or any other reason. The majority of the AEs were of mild intensity. All doses were safe and well tolerated.

At all dose levels, the botulinum neurotoxin was efficacious in reducing GL severity up to 28 days at maximum frown and at rest. At all dose levels, botulinum neurotoxin was efficacious in reducing LCL severity up to 28 days at maximum frown and at rest. At all dose levels, botulinum neurotoxin was efficacious in reducing GL and LCL severity, when treated in combination, up to 28 days at maximum frown. The effect was less apparent at rest.

Figure 2:
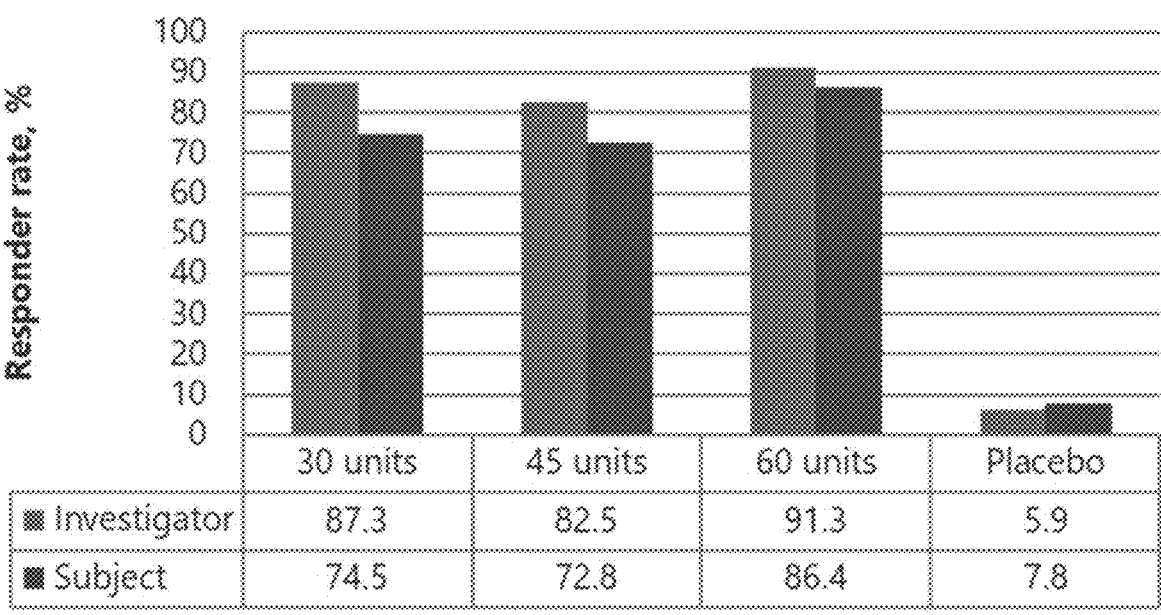
FIG. 2 demonstrates that the responder rate of treatment at 30, 45, and 60 units dosage level of BoNT (QM1114-DP formulation) are significantly higher than the placebo group.

Phase 2 study was conducted to evaluate the efficacy of 3 doses (30, 45 and 60 units) of BoNT in the treatment of GL on Day 14, by Investigator and subject separately. As shown in FIG. 2, the primary objective was met for all dose levels of botulinum neurotoxin compared to placebo. At each dose level, the treatment group has significant higher level of responder rate than the placebo group.

Most common TEAEs in the botulinum neurotoxin treatment groups include injection site pain (15.9%), headache (10.4%), eyelid ptosis (3.9%), and injection site swelling (1.3%).

TABLE 1

| TEAEs in phase II trial | | | | |
|---|---|---|---|---|
| | 30 units (%) | 45 units (%) | 60 units (%) | Placebo (%) |
| Injection site pain | 13.7 | 14.6 | 18.5 | 15.7 |
| Headache | 7.8 | 9.7 | 13.6 | 5.9 |
| Eyelid ptosis | 2.9 | 3.9 | 4.9 | 0 |
| Injection site swelling | 1.0 | 1.0 | 1.9 | 0 |

Figure 3:
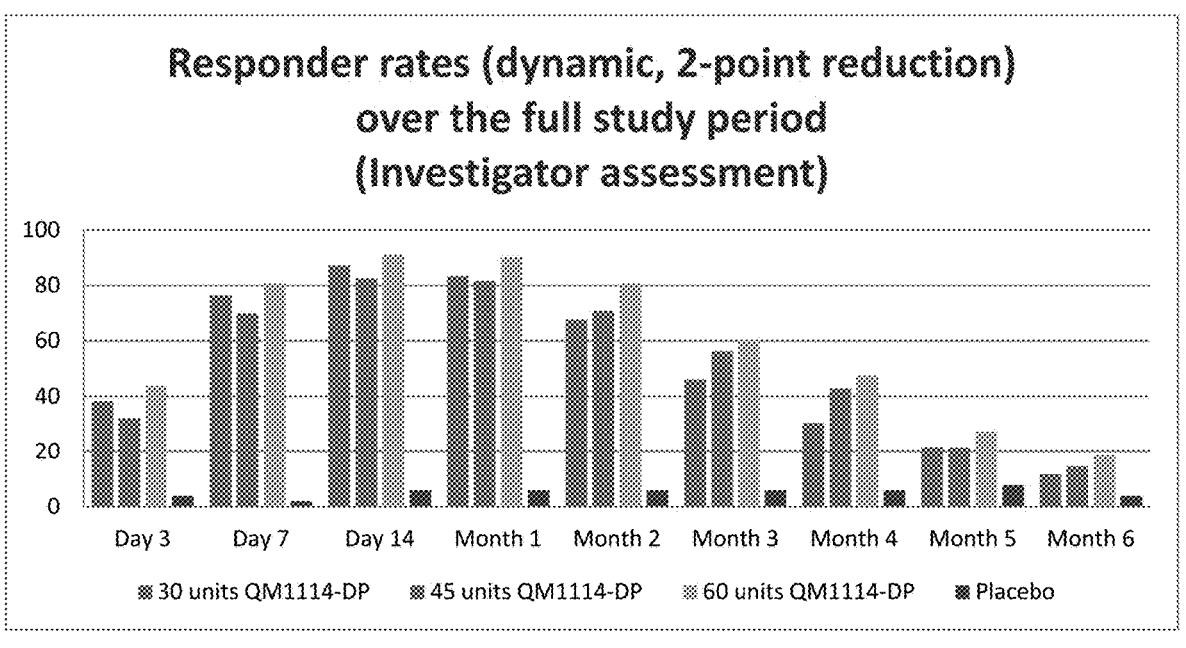
FIG. 3 demonstrates the responder rates over the full study period of six months using QM1114-DP formulation of BoNT.
Figure 4:
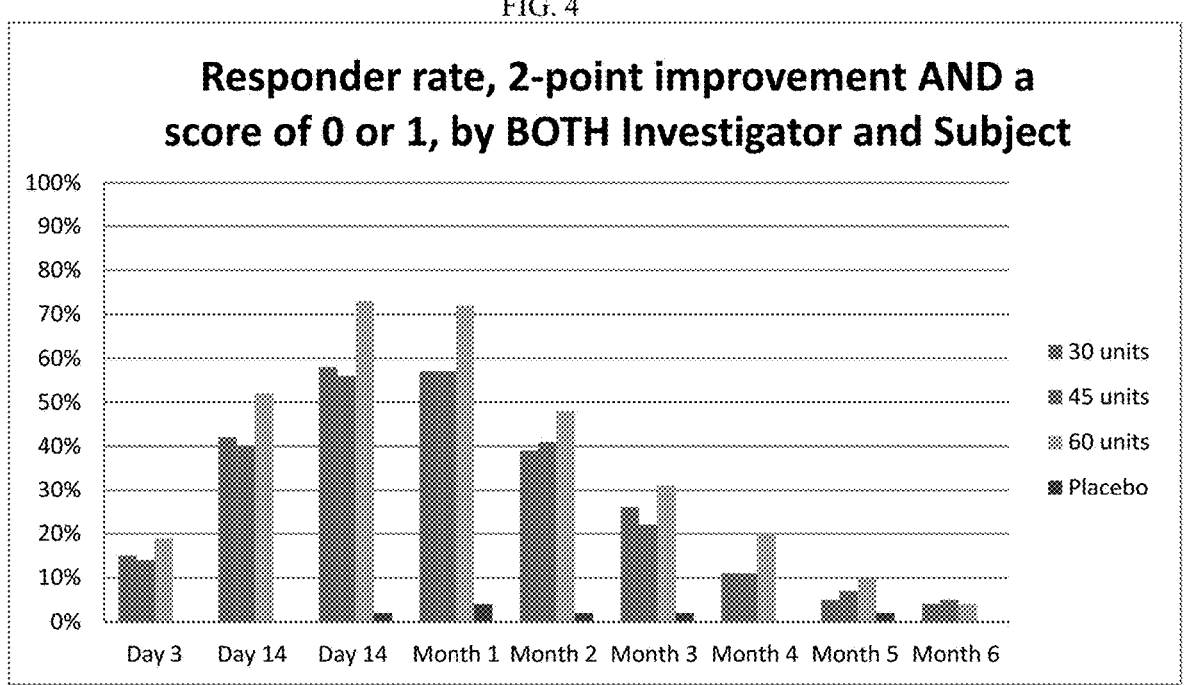
FIG. 4 demonstrates that responder rate, 2-point improvement and a score of 0 or 1, by both investigator and subject using QM1114-DP formulation of BoNT.

In conclusion, phase II study shows that botulinum neurotoxin is safe, and efficacious in reducing GL at all dose levels. Median duration of response is approximately 6 months, as shown in FIG. 3. Patient satisfaction is high.

Phase III Study

The glabellar lines assessments were made using the Merz Aesthetic Severity Scale (MAS) both at rest and at maximum frown (dynamic).

Major eligibility criteria included:

1. Age 18 years or older with Moderate to Very Severe GL at maximum frown as assessed by the subject and the Investigator using MAS (Dynamic) and at least Mild GL at rest using MAS (At Rest).

2. No previous treatment with any botulinum neurotoxin (BoNT), no rhytids of the glabellar region that could not be smoothed out by manually spreading the skin apart.

3. No previous insertion of any permanent or semi-permanent material, hyaluronic acid or collagen fillers to the glabellar region and no history of facial surgery above the lower orbital rim, no planned facial surgery or aesthetic procedure during the study period or ablative skin resurfacing or chemical peels above the lower orbital rim in the previous 12 months or during the study period.

4. No history of eyelid or eyebrow ptosis or amblyopia.

The study population is described in Table 2 below.

TABLE 2

| Study Population | |
|---|---|
| Age | 23-79 years (54% were ≤ 50 years) |
| Gender | 87% females, 13% males |
| Race | 98% White, < 2% Black/African American, < 0.5% Asian |
| Ethnicity | 21% Hispanic/Latino |
| Fitzpatrick | 2% I, 34% II, 45% III, 17% IV, 1% V, 1% VI |

Baseline Demographics

TABLE 3

| | | | 30 units QM1114-DP (N = 102) | 45 units QM1114-DP (N = 103) | 60 units QM1114-DP (N = 103) | Placebo (N = 51) |
|---|---|---|---|---|---|---|
| | | | Baseline MAS Scores | | | |
| MAS Scores at Baseline | | | | | | |
| MAS Dynamic | Subject | Mean (SD) | 3.2 (0.75) | 3.2 (0.74) | 3.2 (0.71) | 3.3 (0.77) |
| | | Moderate | 19 (18.63) | 19 (18.45) | 17 (16.50) | 10 (19.61) |
| | | Severe | 40 (39.22) | 43 (41.75) | 47 (45.63) | 18 (35.29) |
| | | Very Severe | 43 (42.16) | 41 (39.81) | 39 (37.86) | 23 (45.10) |
| | Investigator | Mean (SD) | 3.3 (0.66) | 3.3 (0.73) | 3.3 (0.68) | 3.4 (0.63) |
| | | Moderate | 12 (11.76) | 17 (16.50) | 13 (12.62) | 4 (7.84) |
| | | Severe | 51 (50.00) | 42 (40.78) | 48 (46.80) | 24 (47.06) |
| | | Very Severe | 39 (38.24) | 44 (42.72) | 42 (40.78) | 23 (45.10) |
| MAS At Rest | Subject | Mean (SD) | 1.9 (0.87) | 2.0 (0.86) | 1.9 (0.91) | 1.9 (0.98) |
| | | None | 1 (0.98) | 0 | 0 | 0 |
| | | Mild | 40 (39.22) | 35 (33.98) | 44 (42.72) | 21 (41.18) |
| | | Moderate | 36 (35.29) | 42 (40.78) | 37 (35.92) | 18 (35.29) |
| | | Severe | 22 (21.57) | 21 (20.39) | 15 (14.56) | 7 (13.73) |
| | | Very Severe | 3 (2.94) | 5 (4.85) | 7 (6.80) | 5 (9.80) |
| | Investigator | Mean (SD) | 1.5 (0.74) | 1.6 (0.74) | 1.6 (0.74) | 1.6 (0.80) |
| | | Mild | 61 (59.80) | 56 (54.37) | 53 (51.46) | 30 (58.82) |
| | | Moderate | 34 (33.33) | 31 (30.10) | 36 (34.95) | 13 (25.49) |
| | | Severe | 3 (2.94) | 16 (15.53) | 13 (12.62) | 7 (13.73) |
| | | Very Severe | 4 (3.92) | 0 | 1 (0.97) | 1 (1.96) |

At Baseline, mean MASDynamic scores were similar for the subject and Investigator assessments but mean MAS At Rest scores were higher for the subject assessment than Investigator assessment.

Primary Endpoint

TABLE 4

| | 30 units QM1114-DP (N = 102) | 45 units QM1114-DP (N = 103) | 60 units QM1114-DP (N = 103) | Placebo (N = 51) |
|---|---|---|---|---|
| | Assessment at primary endpoint | | | |
| Subject Assessment | | | | |
| Responded, n (%) | 76 (74.51) | 75 (72.82) | 89 (86.41) | 4 (7.84) |
| [95% Cl] | [64.92, 82.62] | [63.16, 81.12] | [78.25, 92.37] | [2.18, 18.88] |
| Did Not Respond, n (%) | 26 (25.49) | 28 (27.18) | 14 (13.59) | 47 (92.16) |
| [95% Cl] | [17.38, 35.08] | [18.88, 36.84] | [7.63, 21.75] | [81.12, 97.82] |
| Missing Responses, n (%) [a] | 1 (0.98) | 0 | 1 (0.97) | 2 (3.92) |
| Difference vs. placebo (95% Cl) | 66.67 (55.44, 77.89) | 64.97 (53.65, 76.30) | 78.56 (68.65. 88.48) | |
| Investigator Assessment | | | | |
| Responded, n (%) | 89 (87.25) | 85 (82.52) | 94 (91.26) | 3 (5.88) |
| [95% Cl] | [79.19, 93.04] | [73.79, 89.30] | [84.06, 95.93] | [1.23, 16.24] |
| Did Not Respond, n (%) | 13 (12.75) | 18 (17.48) | 9 (8.74) | 48 (94.12) |
| [95% Cl] | [6.96, 20.81] | [10.70, 26.21] | [4.07, 15.94] | [83.76, 98.77] |
| Missing Responses, n (%) [a] | 1 (0.98) | 0 | 1 (0.97) | 2 (3.92) |
| Difference vs. placebo (95% Cl) | 81.37 (72.23, 90.51) | 76.64 (66.87, 86.41) | 85.38 (76.93, 93.83) | |

As shown in Table 4 above, the difference in MAS Dynamic responder rates at Day 14 for 60 units, 45 units, and 30 units botulinum neurotoxin compared to placebo were statistically significant for both co-primary variables (p<0.001).

Secondary Endpoints

MAS Dynamic: For the secondary efficacy analyses, a responder was defined as a subject with at least 2 points reduction from Baseline in GL severity using MAS Dynamic, separately for the subject and investigator assessment. Subject assessment was conducted up to month 6 for all botulinum neurotoxin treatment groups. Investigator assessment was conducted up to month 5 for the 30 units and 45 units treatment groups and up to month 6 for the 60 units treatment group.

MAS At Rest: For the secondary efficacy analyses, a responder was defined as a subject with at least 1 point reduction from Baseline in GL severity using MAS At Rest. Subject assessment was conducted up to month 6 for all botulinum neurotoxin treatment groups. Investigator assessment was conducted up to month 4 for the 30 units and 45 units treatment groups and up to month 5 for the 60 units treatment group.

Results: The definition of duration of response was specifically defined for this study. Duration of response (as defined in this study) was measured separately for the Investigator and the subject assessment of GL severity using MAS Dynamic as time between the first occurrence of at least 2 points reduction and the return to the baseline score.

For investigator assessment, median duration of response (as defined above) was close to 6 Months for the 30 units and 45 units treatment groups, while 53% of subjects with response had not returned to baseline at month 6 in the 60 units treatment group. In the placebo group, median duration of response was approximately 3.5 months.

For subject assessment, the difference between botulinum neurotoxin treatment groups and placebo was less pronounced, median duration of response was approximately 6 Months for the botulinum neurotoxin treatment groups and 4.5 Months for the placebo treatment group.

Onset of action (as defined in this study) was measured separately for the Investigator and the subject assessment of GL severity using MAS Dynamic as time to a first reduction of 1 point compared to Baseline and a time to first reduction of 2 points compared to Baseline.

The results show that time course to first reduction of at least 1 point was similar in the botulinum neurotoxin treatment groups when using the Investigator and subject assessments, with a median of 8 days. Time course to first reduction of at least 2 points was similar in the botulinum neurotoxin treatment groups when using the Investigator and subject assessments, with a median of 8 or 9 days.

In addition, the proportions of subjects who were 'very satisfied' or 'satisfied' were higher in the botulinum neurotoxin treatment groups than in the Placebo group at all time points. The reverse was also true, i.e., the proportions of subjects who were 'dissatisfied' or 'very dissatisfied' were lower in the botulinum neurotoxin treatment groups than in the Placebo group. The highest level of treatment satisfaction was found at Month 1. There did not appear to be any relationship between dose and level of treatment satisfaction.

Safety

Botulinum neurotoxin was safe and well tolerated at all dose levels in this study. The treatment-related treatment-emergent adverse events (TEAEs) seen were of similar type as reported for other toxins in GL treatment. The most common (at least 1% of subjects in any botulinum neurotoxin treatment group) treatment-related TEAEs were injection site pain, headache, eyelid ptosis, injection site swelling, injection site pruritus and visual impairment. There was a trend for a dose-effect for most of these treatment-related TEAEs. The majority of the treatment-related TEAEs were mild or moderate.

Treatment-related eyelid ptosis was found in: 3 subjects (2.9%) in the 30 units treatment group; 4 subjects (3.9%) in the 45 units treatment group; and 5 subjects (4.9%) in the 60 units treatment group. There were no treatment related TEAEs suggestive of a more distant spreading effect of the toxin.

There were no treatment-related severe adverse events (SAEs). Four unrelated SAEs occurred in the study, including a positive maternal test for Down syndrome (30 units), a major depression (45 units), a live birth with cleft palate (45 units), and a pancreatitis (60 units). There were no deaths or AEs leading to withdrawal during the study.

In conclusion, the primary efficacy endpoint at Day 14 confirmed the efficacy of all botulinum neurotoxin doses (30, 45, and 60 units) versus placebo. The MAS Dynamic responder rates at Day 14 were high across all the botulinum neurotoxin treatment groups (73% to 91%) versus placebo (6% to 8%). The results also confirm that botulinum neurotoxin is efficacious in reducing GL severity. Specifically, at maximum frown in comparison to placebo treatment at all time points up to Month 6 by subject assessment and up to Month 5 for the 30 units and 45 units treatment groups and up to Month 6 for the 60 units treatment group by Investigator assessment. At Rest in comparison to placebo for all botulinum neurotoxin dose levels at all time points up to Month 6 by subject assessment and up to Month 4 for the 30 units and 45 units treatment groups and up to Month 5 for the 60 units treatment group by Investigator assessment. The onset of reduction in GL severity using the MAS scale also showed a similar trend as the subject's treatment satisfaction in this study.

The most common treatment-related TEAEs are: injection site pain, headache, eyelid ptosis, injection site swelling, injection site pruritus and visual impairment. The incidence of treatment-related TEAEs was highest in the 45 unit (33%) and 60 unit (36%) botulinum neurotoxin dose groups. The incidence of eyelid ptosis in this study was 3% to 5%.

There were no treatment related SAEs (4 unrelated SAEs occurred in the study and were entered in the safety database), and no death. There were no AEs leading to withdrawal during the study. There were three pregnancies reported during the study, one pregnancy in the 30 units dose group and two pregnancies in the 45 units dose group.

Results are summarized in the tables below.

TABLE 5

2 point reduction in MAS Dynamic score by Investigator and subject, separately

| Responder Rates | 30 units QM1114-DP (N = 102) n (%) p-value [b] | 45 units QM1114-DP (N = 103) n (%) p-value [b] | 60 units QM1114-DP (N = 103) n (%) p-value [b] | Placebo (N = 51) n (%) p-value [b] |
|---|---|---|---|---|
| Subject assessment | | | | |
| Day 3-Responded | 32 (31.37) <0.001 | 34 (33.01) <0.001 | 33 (32.04) <0.001 | 2 (3.92) |
| Day 7-Responded | 60 (58.82) <0.001 | 64 (62.14) <0.001 | 78 (75.73) <0.001 | 2 (3.92) |
| Day 14-Responded [e] | 76 (74.51) <0.001 | 75 (72.82) <0.001 | 89 (86.41) <0.001 | 4 (7.84) |
| Month 1-Responded | 80 (78.43) <0.001 | 72 (69.90) <0.001 | 88 (85.44) <0.001 | 5 (9.80) |

TABLE 5-continued 2 point reduction in MAS Dynamic score by Investigator and subject, separately

| Responder Rates | 30 units QM1114-DP (N = 102) n (%) p-value [b] | 45 units QM1114-DP (N = 103) n (%) p-value [b] | 60 units QM1114-DP (N = 103) n (%) p-value [b] | Placebo (N = 51) n (%) |
|---|---|---|---|---|
| Month 2-Responded | 65 (63.73) <0.001 | 60 (58.25) <0.001 | 77 (74.76) <0.001 | 3 (5.88) |
| Month 3-Responded | 51 (50.00) <0.001 | 47 (45.63) <0.001 | 57 (55.34) <0.001 | 3 (5.88) |
| Month 4-Responded | 43 (42.16) <0.001 | 39 (37.86) <0.001 | 38 (36.89) <0.001 | 1 (1.96) |
| Month 5-Responded | 24 (23.53) <0.001 | 26 (25.24) <0.001 | 25 (24.27) <0.001 | 1 (1.96) |
| Month 6-Responded | 16 (15.59) 0.012 | 25 (24.27) <0.001 | 14 (13.59) 0.021 | 1 (1.96) |
| Investigator assessment | | | | |
| Day 3-Responded | 39 (38.24) <0.001 | 33 (32.04) <0.001 | 45 (43.69) <0.001 | 2 (3.92) |
| Day7-Responded | 78 (76.47) <0.001 | 72 (69.90) <0.001 | 83 (80.58) <0.001 | 1 (1.96) |
| Day 14-Responded | 89 (87.25) <0.001 | 85 (82.52) <0.001 | 94 (91.25) <0.001 | 3 (5.88) |
| Month 1-Responded | 85 (83.33) <0.001 | 84 (81.55) <0.001 | 93 (90.29) <0.001 | 3 (5.88) |
| Month 2-Responded | 69 (67.65) <0.001 | 73 (70.87) <0.001 | 83 (80.58) <0.001 | 3 (5.88) |
| Month 3-Responded | 47 (46.08) <0.001 | 58 (56.31) <0.001 | 62 (60.19) <0.001 | 3 (5.88) |
| Month 4-Responded | 31 (30.39) <0.001 | 44 (42.72) <0.001 | 49 (47.57) <0.001 | 3 (5.88) |
| Month 5-Responded | 22 (21.57) 0.040 | 22 (21.36) 0.040 | 26 (27.18) 0.006 | 4 (7.84) |
| Month 6-Responded | 12 (11.76) 0.143 | 15 (14.56) 0.057 | 19 (18.45) 0.013 | 2 (3.92) |

TABLE 6

1 point reduction in MAS Dynamic score, by subject
Summary of Alternative Responder 1 by the Subject (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Response P-value [2] | 64 (62.75) <0.001 | [52.61, 72.12] | 63 (61.17) <0.001 | [51.06, 70.61] | 70 (67.96) <0.001 | [58.04, 76.82] | 13 (25.49) | [14.33, 39.63] |
| Day 7 | | | | | | | | |
| Response P-value [2] | 88 (86.27) <0.001 | [78.04, 92.29] | 91 (88.35) <0.001 | [80.53, 93.83] | 97 (94.17) <0.001 | [87.75, 97.83] | 16 (31.37) | [19.11, 45.89] |
| Day 14 | | | | | | | | |
| Response P-value [2] | 97 (95.10) <0.001 | [88.93, 98.39] | 98 (95.15) <0.001 | [89.03, 98.41] | 101 (98.06) <0.001 | [93.16, 99.76] | 17 (33.33) | [20.76, 47.92] |
| Day 30 | | | | | | | | |
| Response P-value [2] | 92 (90.20) <0.001 | [82.71, 95.20] | 100 (97.09) <0.001 | [91.72, 99.40] | 99 (96.12) <0.001 | [90.35, 98.93] | 16 (31.37) | [19.11, 45.89] |
| Month 2 | | | | | | | | |
| Response P-value [2] | 85 (83.33) <0.001 | [74.66, 89.98] | 93 (90.29) <0.001 | [82.87, 96.25] | 98 (95.15) <0.001 | [89.03, 98.41] | 13 (25.49) | [14.33, 39.63] |
| Month 3 | | | | | | | | |
| Response P-value [2] | 76 (74.51) <0.001 | [64.92, 82.62] | 86 (83.50) <0.001 | [74.89, 90.08] | 91 (88.35) <0.001 | [80.53, 93.83] | 17 (33.33) | [20.76, 47.92] |

TABLE 6-continued 1 point reduction in MAS Dynamic score, by subject
Summary of Alternative Responder 1 by the Subject (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Month 4 | | | | | | | | |
| Response | 73 (71.57) | [61.78, 80.06] | 78 (75.73) | [66.29, 83.64] | 78 (75.73) | [66.29, 83.64] | 17 (33.33) | [20.76, 47.92] |
| P-value [2] | <0.001 | | <0.001 | | <0.001 | | | |
| Month 5 | | | | | | | | |
| Response | 58 (56.86) | [46.68, 66.63] | 61 (59.22) | [49.10, 68.80] | 68 (66.02) | [56.03, 75.06] | 15 (29.41) | [17.49, 43.83] |
| P-value [2] | 0.002 | | <0.001 | | <0.001 | | | |
| Month 6 | | | | | | | | |
| Response | 53 (51.96) | [41.84, 61.96] | 52 (50.49) | [40.46, 60.49] | 60 (58.25) | [48.12, 67.90] | 10 (19.61) | [9.82, 33.12] |
| P-value [2] | <0.001 | | <0.001 | | <0.001 | | | |

Note:
Baseline is defined as the observation taken that is closest to but prior to study treatment on Day 1.
Responder 1 is defined as a subject with at least 1 point reduction in glabeliar severity compared to baseline using MAS Dynamic.
Data that is missing for any reason is imputed using the baseline observation carried forward method (BOCF).
Percentages are based on the number of subjects in the ITT population in each treatment group.
95% CIs were calculated using the exact binomial distribution.
[1]Missing Responses are the values imputed using BOCF.
[2]The Fisher's Exact test is the primary analysis of responder rates between each of the three doses of QM1114-DP and placebo.

TABLE 7

1 point reduction in MAS Dynamic score, by Investigator
Summary of Alternative Responder 1 by Investigator (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Response | 74 (72.55) | [62.82, 80.92] | 74 (71.84) | [62.13, 80.27] | 77 (74.76) | [65.24, 82.80] | 16 (31.37) | [19.11, 45.89] |
| P-value [2] | <0.001 | | <0.001 | | <0.001 | | | |
| Day 7 | | | | | | | | |
| Response | 94 (92.16) | [85.13, 96.55] | 90 (87.38) | [79.38, 93.11] | 100 (97.09) | [91.72, 99.40] | 21 (41.18) | [27.58, 55.83] |
| P-value [2] | <0.001 | | <0.001 | | <0.001 | | | |
| Day 14 | | | | | | | | |
| Response | 101 (99.02) | [94.66, 99.98] | 99 (96.12) | [90.35, 98.93] | 101 (98.06) | [93.16, 99.76] | 23 (45.10) | [31.13, 59.55] |
| P-value [2] | <0.001 | | <0.001 | | <0.001 | | | |
| Day 30 | | | | | | | | |
| Response | 99 (97.06) | [91.64, 99.39] | 98 (95.15) | [89.03, 96.41] | 102 (99.03) | [94.71, 99.98] | 26 (50.98) | [36.60, 55.25] |
| P-value [2] | <0.001 | | <0.001 | | <0.001 | | | |
| Month 2 | | | | | | | | |
| Response | 93 (91.18) | [83.91, 95.89] | 94 (91.26) | [84.06, 95.93] | 102 (99.03) | [94.71, 99.98] | 19 (37.25) | [24.13, 51.92] |
| P-value [2] | <0.001 | | <0.001 | | <0.001 | | | |
| Month 3 | | | | | | | | |
| Response | 86 (84.31) | [75.78, 90.76] | 92 (89.32) | [81.69, 94.55] | 91 (88.35) | [80.53, 93.83] | 18 (35.29) | [22.43, 49.93] |
| P-value [2] | <0.001 | | <0.001 | | <0.001 | | | |
| Month 4 | | | | | | | | |
| Response | 76 (74.51) | [64.92, 82.52] | 85 (82.52) | [73.79, 89.30] | 85 (82.52) | [73.79, 89.30] | 16 (31.37) | [19.11, 45.89] |
| P-value [2] | <0.001 | | <0.001 | | <0.001 | | | |
| Month 5 | | | | | | | | |
| Response | 69 (67.65) | [57.56, 76.58] | 69 (66.99) | [57.03, 75.94] | 75 (72.82) | [63.16, 81.12] | 17 (33.33) | [20.76, 47.92] |
| P-value [2] | <0.001 | | <0.001 | | <0.001 | | | |

TABLE 7-continued 1 point reduction in MAS Dynamic score, by Investigator
Summary of Alternative Responder 1 by Investigator (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Month 6 | | | | | | | | |
| Response | 47 (46.08) | [36.16, 56.23] | 58 (56.31) | [46.18, 66.06] | 63 (61.17) | [51.06, 70.61] | 13 (25.49) | [14.33, 39.63] |
| P-value [2] | 0.015 | | <0.001 | | <0.001 | | | |

Source: Listing 16.2.5.4

Note:

Baseline is defined as the observation taken that is closest to but prior to study treatment on Day 1.

Responder 1 is defined as a subject with at least 1 point reduction in glabeliar severity compared to baseline using MAS At Rest.

Data that is missing for any reason is imputed using the baseline observation carried forward method (BOCF).

Percentages are based on the number of subjects in the ITT population in each treatment group.

95% CIs were calculated using the exact binomial distribution.

[1]Missing Responses are the values imputed using BOCF.

[2]The Fisher's Exact test is the primary analysis of responder rates between each of the three doses of QM1114-DP and placebo.

TABLE 8

2 point reduction in MAS Dynamic AND a score of 0 or 1 by both Investigator and subject (composite)
Summary of Subjects with at Least 2 Points Improvement and Score of 0 or 1 (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Responded [1] | 15 (14.71) | [0.08, 0.23] | 15 (14.56) | [0.08, 0.23] | 20 (19.42) | [0.12, 0.28] | 0 | |
| P-value | 0.003 | | 0.003 | | <0.001 | | | |
| Day 7 | | | | | | | | |
| Responded [1] | 43 (42.16) | [0.32, 0.52] | 42 (40.78) | [0.31, 0.51] | 54 (52.43) | [0.42, 0.52] | 0 | |
| P-value | <0.001 | | <0.001 | | <0.001 | | | |
| Day 14 | | | | | | | | |
| Responded [1] | 60 (58.82) | [0.49, 0.68] | 59 (57.28) | [0.47, 0.67] | 75 (72.82) | [0.63, 0.81] | 1 (1.96) | [0.00, 0.10] |
| P-value | <0.001 | | <0.001 | | <0.001 | | | |
| Day 30 | | | | | | | | |
| Responded [1] | 59 (57.84) | [0.46, 0.68] | 80 (58.25) | [0.48, 0.68] | 75 (72.82) | [0.63, 0.81] | 2 (3.92) | [0.00, 0.13] |
| P-value | <0.001 | | <0.001 | | <0.001 | | | |
| Month 2 | | | | | | | | |
| Responded [1] | 39 (38.24) | [0.29, 0.48] | 43 (41.75) | [0.32, 0.52] | 50 (48.54) | [0.39, 0.59] | 1 (1.96) | [0.00, 0.10] |
| P-value | <0.001 | | <0.001 | | <0.001 | | | |
| Month 3 | | | | | | | | |
| Responded [1] | 26 (25.49) | [0.17, 0.35] | 23 (22.33) | [0.15, 0.32] | 33 (32.04) | [0.23, 0.42] | 1 (1.95) | [0.00, 0.10] |
| P-value | <0.001 | | <0.001 | | <0.001 | | | |
| Month 4 | | | | | | | | |
| Responded [1] | 11 (10.78) | [0.06, 0.18] | 11 (10.68) | [0.05, 0.18] | 22 (21.36) | [0.14, 0.31] | 0 | |
| P-value | 0.016 | | 0.016 | | <0.001 | | | |
| Month 5 | | | | | | | | |
| Responded [1] | 5 (4.90) | [0.02, 0.11] | 7 (6.80) | [0.03, 0.14] | 11 (10.68) | [0.05, 0.18] | 1 (1.96) | [0.00, 0.10] |
| P-value | 0.664 | | 0.272 | | 0.106 | | | |

TABLE 8-continued 2 point reduction in MAS Dynamic AND a score of 0 or 1 by both Investigator and subject (composite)
Summary of Subjects with at Least 2 Points Improvement and Score of 0 or 1 (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Month 6 | | | | | | | | |
| Responded [1] | 4 (3.92) | [0.01, 0.10] | 5 (4.85) | [0.02, 0.11] | 4 (3.88) | [0.01, 0.10] | 0 | |
| P-value | 0.302 | | 0.171 | | 0.302 | | | |

Note:

Baseline is defined as the observation taken that is closest to but prior to study treatment on Day 1.

The Responder is is a composite endpoint, defined as a subject with at least 2 points reduction from baseline and a score of 0 or 1 by both Investigator and subject assessment using MAS Dynamic.

Data that is missing for any reason is imputed using the baseline observation carried forward method (BOCF)..

Percentages are based on the number of subjects in the ITT population in each treatment group.

95% CIs were calculated using the exact binomial distribution.

[1]The Fisher's Exact test is the primary analysis of responder rates between each of the three doses of QM1114-DP and placebo.

TABLE 9

2 point reduction in MAS Dynamic by both Investigator and subject (composite)
Table 14.2.1.12 Summary of Alternative Responder 2 (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Responded | 23 (22.55) | [14.86, 31.89] | 24 (23.30) | [15.54, 32.66] | 25 (24.27) | [16.36, 33.71] | 0 | |
| P-value [2] | <0.001 | | <0.001 | | <0.001 | | | |
| Day 7 | | | | | | | | |
| Responded | 55 (53.92) | [43.77, 63.84] | 52 (50.49) | [40.46, 60.49] | 70 (67.96) | [58.04, 76.82] | 0 | |
| P-value [2] | <0.001 | | <0.001 | | <0.001 | | | |
| Day 14 | | | | | | | | |
| Responded | 70 (68.63) | [58.69, 77.45] | 67 (65.05) | [55.02, 74.18] | 85 (82.52) | [73.79, 89.30] | 1 (1.96) | [0.05, 10.45] |
| P-value [2] | <0.001 | | <0.001 | | <0.001 | | | |
| Day 30 | | | | | | | | |
| Responded | 71 (69.61) | [59.71, 78.33] | 67 (65.05) | [55.02, 74.18] | 83 (80.56) | [71.62, 87.72] | 2 (3.92) | [0.48, 13.46] |
| P-value [2] | <0.001 | | <0.001 | | <0.001 | | | |
| Month 2 | | | | | | | | |
| Responded | 51 (50.00) | [39.93, 60.07] | 53 (51.46) | [41.40, 61.42] | 67 (65.05) | [55.02, 74.18] | 1 (1.96) | [0.05, 10.45] |
| P-value [2] | <0.001 | | <0.001 | | <0.001 | | | |
| Month 3 | | | | | | | | |
| Responded | 33 (32.35) | [23.42, 42.34] | 35 (34.95) | [25.82, 44.98] | 46 (44.68) | [34.86, 54.78] | 1 (1.96) | [0.05, 10.45] |
| P-value [2] | <0.001 | | <0.001 | | <0.001 | | | |
| Month 4 | | | | | | | | |
| Responded | 20 (19.61) | [12.41, 28.65] | 25 (24.27) | [16.36, 33.71] | 28 (27.18) | [18.88, 36.84] | 0 | |
| P-value [2] | <0.001 | | <0.001 | | <0.001 | | | |
| Month 5 | | | | | | | | |
| Responded | 11 (10.78) | [5.51, 18.48] | 11 (10.68) | [5.45, 18.31] | 13 (12.62) | [6.89, 20.62] | 1 (1.96) | [0.05, 10.45] |
| P-value [2] | 0.062 | | 0.106 | | 0.036 | | | |
| Month 6 | | | | | | | | |
| Responded | 5 (4.90) | [1.61, 11.07] | 12 (11.65) | [6.17, 19.47] | 7 (6.80) | [2.78, 13.50] | 0 | |
| P-value [2] | 0.170 | | 0.009 | | 0.096 | | | |

Note:

Baseline is defined as the observation taken that is closest to but prior to study treatment on Day 1.

Responder 2 is a composite endpoint, defined as a subject with at least 2 points reduction from baseline by both Investigator and subject assessment using MAS Dynamic.

Data that is missing for any reason is imputed using the worst observation carried forward method (WOCF).

Percentages are based on the number of subjects in the ITT population in each treatment group.

95% CIs were calculated using the exact binomial distribution.

[2]The Fisher's Exact test is the primary analysis of responder rates between each of the three doses of QM1114-DP and placebo.

TABLE 10

2 point reduction in MAS Dynamic AND a score of 0 or 1, by subject
Summary of Subjects with at Least 2 Points Improvement and Score of 0 or 1 by the Subject (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Responded [1] | 23 (22.55) | [0.15, 0.32] | 21 (20.39) | [0.13, 0.29] | 23 (22.33) | [0.15, 0.32] | 1 (1.96) | [0.00, 0.10] |
| P-value | <0.001 | | 0.001 | | <0.001 | | | |
| Day 7 | | | | | | | | |
| Responded [1] | 47 (46.08) | [0.36, 0.56] | 52 (50.49) | [0.40, 0.60] | 64 (62.14) | [0.52, 0.72] | 0 | |
| P-value | <0.001 | | <0.001 | | <0.001 | | | |
| Day 14 | | | | | | | | |
| Responded [1] | 65 (63.73) | [0.54, 0.73] | 65 (63.11) | [0.53, 0.72] | 80 (77.67) | [0.68, 0.55] | 2 (3.92) | [0.00, 0.13] |
| P-value | <0.001 | | <0.001 | | <0.001 | | | |
| Day 30 | | | | | | | | |
| Responded [1] | 66 (64.71) | [0.55, 0.74] | 66 (64.06) | [0.54, 0.73] | 78 (75.73) | [0.66, 0.842] | 2 (3.92) | [0.00, 0.13] |
| P-value | <0.001 | | <0.001 | | <0.001 | | | |
| Month 2 | | | | | | | | |
| Responded [1] | 42 (41.18) | [0.32, 0.51] | 47 (45.63) | [0.36, 0.56] | 61 (50.22) | [0.49, 0.89] | 1 (1.96) | [0.00, 0.10] |
| P-value | <0.001 | | <0.001 | | <0.001 | | | |
| Month 3 | | | | | | | | |
| Responded [1] | 34 (33.33) | [0.24, 0.43] | 33 (32.04) | [0.23, 0.42] | 41 (39.81) | [0.30, 0.50] | 1 (1.96) | [0.00, 0.10] |
| P-value | <0.001 | | <0.001 | | <0.001 | | | |
| Month 4 | | | | | | | | |
| Responded [1] | 23 (22.55) | [0.15, 0.32] | 22 (21.36) | [0.14, 0.31] | 27 (26.21) | [0.18, 0.36] | 0 | |
| P-value | <0.001 | | <0.001 | | <0.001 | | | |
| Month 5 | | | | | | | | |
| Responded [1] | 11 (10.78) | [0.06, 0.18] | 15 (14.56) | [0.06, 0.23] | 16 (15.53) | [0.09, 0.24] | 1 (1.96) | [0.00, 0.10] |
| P-value | 0.062 | | 0.022 | | 0.012 | | | |
| Month 6 | | | | | | | | |
| Responded [1] | 9 (8.82) | [0.04, 0.16] | 10 (9.71) | [0.06, 0.17] | 11 (10.68) | [0.05, 0.18] | 1 (1.95) | [0.00, 0.10] |
| P-value | 0.166 | | 0.102 | | 0.106 | | | |

Note:
Baseline is defined as the observation taken that is closest to but prior to study treatment on Day 1.
The Responder is defined as a subject with at least 2 points reduction from baseline and a score of 0 or 1 by the subject.
Data that is missing for any reason is imputed using the baseline observation carried forward method (BOCF).
Percentages are based on the number of subjects in the PP population in each treatment group.
95% CIs were calculated using the exact binomial distribution.
[1]The Fisher's Exact test is the primary analysis of responder rates between each of the three doses of QM1114-DP and placebo.

TABLE 11

2 point reduction in MAS Dynamic AND a score of 0 or 1, by Investigator
Summary of Subjects with at Least 2 Points Improvement and Score of 0 or 1 by the Investigator (ITT Population)

| | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
| | n (%) | [95% CI] | n (%) | [95% CI] | n (%) | [95% CI] | n (%) | [95% CI] |
| Day 3 | | | | | | | | |
| Responded [1] | 24 (23.53) | [0.16, 0.33] | 23 (22.33) | [0.15, 0.32] | 29 (28.16) | [0.20, 0.38] | 1 (1.96) | [0.00, 0.10] |
| P-value | <0.001 | | 0.001 | | <0.001 | | | |
| Day 7 | | | | | | | | |
| Responded [1] | 66 (64.71) | [0.55, 0.74] | 62 (80.19) | [0.50, 0.70] | 70 (67.96) | [0.58, 0.77] | 1 (1.96) | [0.00, 0.10] |
| P-value | <0.001 | | <0.001 | | <0.001 | | | |
| Day 14 | | | | | | | | |
| Responded [1] | 79 (77.45) | [0.68, 0.85] | 78 (75.73) | [0.66, 0.84] | 92 (89.32) | [0.82, 0.95] | 3 (5.88) | [0.01, 0.16] |
| P-value | <0.001 | | <0.001 | | <0.001 | | | |

TABLE 11-continued 2 point reduction in MAS Dynamic AND a score of 0 or 1, by Investigator
Summary of Subjects with at Least 2 Points Improvement and Score of 0 or 1 by the Investigator (ITT Population)

|  | 30 Units QM1114-DP (N = 102) | | 45 Units QM1114-DP (N = 103) | | 60 Units QM1114-DP (N = 103) | | Placebo (N = 51) | |
|---|---|---|---|---|---|---|---|---|
|  | n (%) | [95% CI] | n (%) | [95% CI] | n (%) | [95% CI] | n (%) | [95% CI] |
| Day 30 | | | | | | | | |
| Responded [1] | 75 (73.53) | [0.64, 0.82] | 74 (71.84) | [0.62, 0.80] | 87 (84.47) | [0.78, 0.91] | 3 (5.88) | [0.01, 0.16] |
| P-value | <0.001 | | <0.001 | | <0.001 | | | |
| Month 2 | | | | | | | | |
| Responded [1] | 54 (52.94) | [0.43, 0.63] | 62 (60.19) | [0.50, 0.70] | 89 (66.99) | [0.57, 0.76] | 2 (3.92) | [0.00, 0.13] |
| P-value | <0.001 | | <0.001 | | <0.001 | | | |
| Month 3 | | | | | | | | |
| Responded [1] | 37 (36.27) | [0.27, 0.46] | 36 (34.95) | [0.26, 0.45] | 52 (50.49) | [0.48, 0.60] | 2 (3.92) | [0.00, 0.13] |
| P-value | <0.001 | | <0.001 | | <0.001 | | | |
| Month 4 | | | | | | | | |
| Responded [1] | 24 (23.53) | [0.16, 0.33] | 23 (22.33) | [0.15, 0.32] | 32 (31.07) | [0.22, 0.41] | 1 (1.96) | [0.00, 0.10] |
| P-value | <0.001 | | <0.001 | | <0.001 | | | |
| Month 5 | | | | | | | | |
| Responded [1] | 13 (12.75) | [0.07, 0.21] | 14 (13.59) | [0.08, 0.22] | 16 (15.53) | [0.09, 0.24] | 2 (3.92) | [0.00, 0.13] |
| P-value | 0.148 | | 0.091 | | 0.036 | | | |
| Month 6 | | | | | | | | |
| Responded [1] | 8 (7.84) | [0.03, 0.15] | 7 (6.80) | [0.03, 0.14] | 12 (11.65) | [0.06, 0.19] | 1 (1.96) | [0.00, 0.10] |
| P-value | 0.273 | | 0.272 | | 0.061 | | | |

Note:
Baseline is defined as the observation taken that is closest to but prior to study treatment on Day 1.
The Responder is defined as a subject with at least 2 points reduction from baseline and a score of 0 or 1 by the Investigator.
Data that is missing for any reason is imputed using the baseline observation carried forward method (BOCF).
Percentages are based on the number of subjects in the ITT population in each treatment group.
95% CIs were calculated using the exact binomial distribution.
[1]The Fisher's Exact test is the primary analysis of responder rates between each of the three doses of QM1114-DP and placebo.

Example 2—A Randomized, Double-Blind,
Placebo-Controlled, Single Treatment,
Dose-Escalation Study to Evaluate the Safety and
Efficacy of QM1114-DP in Healthy Male and
Female Subjects with Moderate to Severe Upper
Facial Wrinkles Pre-Clinical Studies The pre-clinical pharmacology-toxicology program to support the Phase I clinical trial included pre-clinical pharmacology studies to provide proof-of-concept for first in man (FIM) administration of the product for the indication. The pre-clinical program also included appropriate toxicology studies to support safety for first-in-man administration of QM1114-DP.

Proof-of-concept pharmacology studies with QM1114-DP have been performed in a mouse hind limb paralysis assay to demonstrate that intramuscular (IM) administration of the product induces partial muscle paralysis at the local injection site in a manner similar to the currently marketed BoNT-A products. A pre-clinical pharmacology study was also performed using both an early version of a mouse LD50 assay (the standard assay for assessment of BoNT-A potency) and the mouse hind limb assay.

No safety pharmacology or pharmacokinetic studies were conducted for QM1114-DP since no systemic exposure to the product is expected with a single IM administration to specific facial muscles using the doses proposed for the clinical study. Additionally, BoNT-A binds with high affinity at the neuronal synapses at the local injection site (Montecucco et al., 2004). Therefore, any metabolism and elimination of the product would occur at the local site of injection.

General toxicology studies were conducted for QM1114-DP, including pilot single IM dose administration toxicity studies in Wistar rats and Beagle dogs. These were non-GLP (Good Laboratory Practice) studies performed for the purpose of determining the maximum tolerated dose for QM1114-DP to allow for setting the appropriate dose levels for the pivotal GLP toxicology study. Results of these pilot toxicology studies have clearly demonstrated that the Wistar rat was more sensitive to the toxic effects of QM1114-DP than the dog, and therefore the pivotal GLP toxicology study was conducted only in Wistar rats.

No separate local tolerance studies were performed with QM1114-DP. Instead, local tolerance was carefully evaluated through clinical observation and histopathology evaluation of the local injection sites as part of the pivotal GLP toxicology study in Wistar rats. No unexpected data were determined from these additional observations which indicated tolerance issues with the product.

Clinical Studies

In Example 1 (GL only) of this clinical study, (43QM1302 [n=30]) the safety and tolerability of 10, 25, 50 and 75 units of QM1114-DP was evaluated. A total of 48 adverse events (AE) were reported in 23 subjects, none of which were serious and the majority were of mild intensity. Thirty-two (32) AEs in 16 subjects were assessed as treatment related by the Investigator. Of the 32 treatment related AEs the majority (17 events) were reported in the 75 unit QM1114-DP dose level of which general disorders and administration site conditions followed by skin and subcutaneous tissue disorders were the most commonly reported AEs. The frequency of eye disorders, general disorders and administration site conditions, and skin and subcutaneous tissue disorders appeared to be associated with dose. Eye disorders such as asthenopia were not reported for any subject in the 10 unit and 25 unit QM1114-DP dose levels; however the 50 unit and 75 unit QM1114-DP dose levels were associated with a modest increase in the frequency of eye disorders. Similarly, this trend was also observed for general disorders and administration site conditions. Apart from these trends, there were no clinically meaningful safety findings including clinical laboratory values, vital signs, physical examinations and electrocardiogram (ECG) parameters for any of the treatments.

Efficacy

In Part 1 of this clinical study 43QM1302 (n=30), the efficacy of 10, 25, 50 and 75 units of QM1114-DP was evaluated using Merz 5-point photo scales (Merz Aesthetic Scale: MAS) for Investigator's and subject's assessments of severity of rhytids of the glabellar region at rest and at maximum frown. The scales used the following grades for the severity of GL: 0 (none), 1 (mild), 2 (moderate), 3 (severe) and 4 (very severe). The efficacy analyses revealed that at all dose levels QM1114-DP was efficacious in reducing GL severity up to 28 days at maximum frown in comparison to those subjects in the placebo treatment group. At rest the GL severity was decreased in the active treatment groups as assessed by the Investigator and subject in comparison to the placebo treatment group. This effect was maintained up to 28 days. The subject's assessment of GL satisfaction showed that with the exception of one subject all subjects in active treatment groups were either very satisfied or satisfied with treatment through to Day 28. Furthermore, the reduction in rhytid severity was still apparent up to Day 28 for all dose levels. In conclusion, the efficacy data showed that QM1114-DP is efficacious in reducing GL severity at maximum frown at all dose levels in comparison to those subjects evaluated in the placebo treatment group.

The efficacy of QM1114-DP in reduction of rythid severity of the lateral canthal lines had not been studied prior to the study disclosed in this example.

Study Objectives

Primary Objective: To evaluate the safety and tolerability of QM1114-DP at each dose level.

Secondary Objectives: To assess the efficacy of QM1114-DP at each dose level for the temporary improvement of the glabellar lines (GL) and lateral canthal lines (LCL); and to assess the efficacy of QM1114-DP at each dose level for the temporary improvement of the GL and LCL, when treated in combination.

Study Endpoints

Safety: Incidence and severity of AEs.

Efficacy:

Investigator's rating of LCL severity at maximum smile through Day 28 (week 4) by live assessment using Merz Aesthetic Scale (MAS) LCL—dynamic;

Investigator's rating of LCL severity at rest through Day 28 (week 4) by live assessment using MAS LCL—at rest (static);

Subject's rating of LCL severity at maximum smile through Day 28 (week 4) by live assessment using MAS LCL—dynamic;

Subject's rating of LCL severity at rest through Day 28 (week 4) by live assessment using MAS LCL—at rest (static); and Subject's assessment of satisfaction through Day 28 (week 4) using a 4-point rating scale.

Exploratory:

Investigator's rating of LCL severity at maximum smile until the rhytid scoring returns to baseline or for up to 6 months by live assessment using MAS LCL—dynamic;

Investigator's rating of LCL severity at rest until the rhytid scoring returns to baseline or for up to 6 months by live assessment using MAS LCL—at rest;

Subject's rating of LCL severity at maximum smile until the rhytid scoring returns to baseline or for up to 6 months by live assessment using MAS LCL—dynamic;

Subject's rating of LCL severity at rest until the rhytid scoring returns to baseline or for up to 6 months by live assessment using MAS LCL—at rest; and Subject's assessment of satisfaction using a 4-point rating scale.

Subjects who participated in the exploratory phase of this study visited the clinical pharmacology unit (CPU) every month. The exploratory endpoints were not included in this example.

Investigational Plan

Overall Study Design and Plan

This clinical Phase I study example deals with LCL only. The Phase I study also included in a separate part (cohorts 1-4), treatment in escalating doses for GL as previously reported. A separate phase (cohorts 8 and 9) evaluating treatment of GL in combination with LCL is reported separately in Example 3.

The study was a randomized, double-blind, placebo-controlled design to evaluate the safety and efficacy of ascending botulinum toxin type A (QM1114-DP; active) doses administered to healthy male and female subjects aged 18 to 65 years with moderate to severe LCL. A total of 24 subjects were enrolled in 3 cohorts (cohorts 5, 6 and 7) with 8 subjects in each cohort (6 active: 2 placebo).

Each healthy subject received verbal (from a Research Physician) and written information prior to signing of the ICF. Subjects were screened for eligibility within 28 days prior to the study treatment on Day 1, and attended study visits for safety and efficacy assessments through the follow-up visit on Day 28 (week 4). All subjects were admitted to the CPU on Day −1 and stayed overnight on the day before dosing on Day 1. Sentinel groups at each dose level were used to minimize risks to subjects. Accordingly, a longer hospitalization in the CPU was required for the first 2 subjects (1 active and 1 placebo) in cohorts 5, 6 and 7. These subjects were admitted to the CPU on Day −1, treated on Day 1, discharged from the CPU on Day 2 and then attended study visits through the follow-up visit on Day 28 (week 4). The study consisted of the following visits: Screening, Day −1, Days 1, 2, 3, 7, 14, 21 and 28.

Investigators and subjects assessed the appearance of LCL at screening, pre-treatment, and at all post-treatment visits using Merz scales LCL dynamic and at rest. Subjects also assessed their satisfaction with the appearance of their LCL using a 4-point rating scale at all post-treatment visits (Ascher et al., 2009).

Subjects were randomized to receive one treatment with study drug (QM1114-DP or placebo). Each treatment included three injections of equal volume (100 µl) administered to each side of the face. The position of the injections were adjusted in accordance with the LCL pattern of rhytids for the individual subject. In all cases, the injection points were at the external part of the orbicularis oculi and, when applicable, at about 1-2 cm from the orbital rim.

The dose levels of QM1114-DP were:

Cohort 5, Dose 1: QM1114-DP at 5 units per injection site (total of 30 units per treatment);

Cohort 6, Dose 2: QM1114-DP at 10 units per injection site (total of 60 units per treatment); and Cohort 7, Dose 3: QM1114-DP at 15 units per injection site (total of 90 units per treatment).

The procedures and assessments that were conducted during this study are presented by study visit in Table 12. The clinical study included the screening and up to week 4 (follow-up) visit. If scoring (maximum smile) had returned to baseline as assessed by the Investigator, subjects had their last visit to the CPU at Day 28 (week 4). At this point the study was completed according to the primary endpoint for these subjects. Subjects whose rhytid severity scores (maximum smile) did not return to baseline at Day 28 (week 4) as assessed by the Investigator, participated in the exploratory phase of this study and visited the CPU every month until the rhytid scoring returned to baseline. Data from this exploratory follow-up of efficacy will be reported separately and not in this CSR.

This study was conducted in a randomised, placebo controlled design to assess the safety and tolerability of QM1114-DP at each dose level and to assess the efficacy of QM1114-DP at each dose level for the temporary improvement of facial line of the left and right lateral canthal region. The selection criteria were defined such that subjects selected for participation in the study were free from any illness.

Selection of Study Population

Within 28 days before the start of the study, subject underwent a full screening procedure as described in Table 12.

TABLE 12

Study Flowchart

| Study Period | Screening Day −28- Day −1 | D −1 | D 1 | D 2 | D 3 | W 1[f] (D7) | W 2[f] (D14) | W 3[f] (D21) | W4[g] (D28) Follow- up |
|---|---|---|---|---|---|---|---|---|---|
| Informed Consent | X | | | | | | | | |
| Inclusion/Exclusion criteria | X | X | | | | | | | |
| Demographic data | X | | | | | | | | |
| Medical History | X | X | | | | | | | |
| Concomitant medication recording | X | X | X | X | X | X | X | X | X |
| Serology | X | | | | | | | | |
| Body weight/height/BMI | X | | | | | | | | X |
| Vital signs | X | X | X[a] | X | X | X | X | X | X |
| Full physical examination | X | X | | | | | | | |
| Focused physical examination[c] | X | X | X[a] | X | X | X | X | X | X |
| 12-lead ECG | X | X | X[a] | X | X | X | X | X | X |
| Alcohol breath test | X | X[b] | | | | | | | |
| Serum pregnancy test | X | X | | | | | | | |
| Haematology/Biochemistry | X | X | | X | | X | X | X | X |
| Urinalysis | X | X | | X | | X | X | X | X |
| Urine Drugs of Abuse | X | X | | | | | | | |
| Clinical Immunogenicity Assay | | X | | | | | | | X |
| AEs (AEs) | X | X | X | X | X | X | X | X | X |
| Efficacy assessments[f] | | | | | | | | | |
| Investigator 'live' assessments | X | X | | X | X | X | X | X | X |
| Subject 'live' assessments | X | X | | X | X | X | X | X | X |
| Subject satisfaction | | | X | X | X | X | X | X | X |
| Photography | X | X | | X | X | X | X | X | X |
| Meals[d] | | X | X | X | | | | | |
| Study drug administration | | X | | | | | | | |
| Hospitalisation[e] | | → | | | | | | | |
| Outpatient visits | | | | X | X | X | X | X | X |

[a]At pre-dose, 1 hour, 4 hours, 8 hours and 12 hours.

[b]An abbreviated physical examination was done on Day −1 and focused on any health changes since screening.

[c]Focused examination of eyes and face.

[d]A light meal was given prior to dosing. At all other times standardised meals were consumed at standard unit times during the in-house period.

[e]All subjects were hospitalised in the morning of Day −1. Subjects in the sentinel groups for cohorts 5, 6 and 7 were hospitalised until Day 2. All other subjects were discharged from the CPU on Day 1.

[f]Flexibility of ±1 day from the scheduled visit was permitted at week 1 and ±2 days from the scheduled visit was permitted from week 2 onwards.

[g]If the efficacy score (investigator 'live' assessment, maximum smile) had not returned to baseline at week 4, the subject attended monthly exploratory follow up visits at the CPU until the score had returned to baseline (as assessed by the Investigator at maximum smile). For subjects whose scoring had returned to baseline, week 4 was their last visit to the CPU.

Inclusion Criteria

To be eligible for inclusion Part 2 of the study, each subject fulfilled each of the following criteria:

Healthy male or female aged between 18 and 65 years (inclusive) at screening.

Had no prior treatment with BoNT-A or B.

Had moderate to severe (Grade 2 or 3) LCL during maximum smile on both sides of the face, as assessed by the Investigator at screening and baseline visits using a validated photo scale (MAS LCL—dynamic).

Had a mild to severe (Grade 1, 2 or 3) LCL at rest on both sides of the face as assessed by the Investigator at screening and baseline visits using a validated photo scale (MAS LCL—at rest).

Subjects agreed to use one of several acceptable methods of contraception.

Were able to understand and comply with the requirements of the protocol and had signed the ICF prior to undergoing any study-related procedures.

Had no clinically significant disease or abnormal laboratory, ECG or vital signs values as determined by medical history, physical examination or other evaluations, conducted at the screening visit or on admission to the CPU.

Exclusion Criteria

A subject was not eligible for inclusion in this study if any of the following criteria applied:

Had received prior BoNT-A or B treatment.

Had rhytids of the LCL area that could not be substantially smoothed-out manually by spreading the skin apart.

Had previous insertion of any permanent or semi-permanent material or had dermal filler treatment to the LCL lines area.

Had an infection in the LCL area within 14 days prior to the baseline visit.

Currently had a history of eyelid or eye brow ptosis.

Had dry eyes, prominent eye bags or morning eyelid oedema.

Had cancerous or pre-cancerous lesions, active or chronic skin disease, inflammation or related conditions including scar near or on the glabellar area.

Had prior facial cosmetic surgery (e.g., blepharoplasty, periorbital surgery, facial lift, brow lift, eyelid lift or eyebrow surgery).

Had facial laser or light treatment, microdermabrasion, or superficial peels within 6 months prior to screening for this study.

Had a history of facial nerve paralysis.

Used topical preparations that claim to have anti-wrinkle activity within 7 days prior to study drug administration or planned to use such preparations while on study.

Subject had facial cosmetic surgery or procedures planned during the study period.

Had flu-like syndrome within 14 days prior to day of injection.

Currently received or had received aminoglycoside antibiotic therapy, curare-like drugs, quinidine, succinylcholine, polymyxins, anticholinesterases, magnesium sulfate, or lincosamides. Any other prescription or non-prescription medications were allowed at the discretion of the Investigator as long as it did not negatively impact on the safety of the subject or integrity of the study data.

Was pregnant or lactating (female subjects of childbearing potential must have had a negative pregnancy test [serum] prior to randomisation).

Had a confirmed positive urine drug screen indicating drug abuse including: opiates, barbiturates, cocaine metabolite, methadone, benzodiazepine, cannabinoid, or amphetamine.

Had a history or clinical evidence of alcoholism or drug abuse. Alcohol abuse is defined as regular weekly intake of more than 14 units if female and 21 units if male (using alcohol tracker nhs.uk/Tools/Pages/NH-SAlcoholtracker.aspx); drug abuse is defined as compulsive, repetitive and/or chronic use of drugs or other substances with or without problems related to their use and/or where stopping or a reduction in dose will lead to withdrawal symptoms.

Had a positive screen for hepatitis B consisting of HBsAG (Hepatitis B surface antigen), anti-HCV (hepatitis C virus antibody) and human immunodeficiency virus (HIV).

Had a history of dysphagia, aspiration or inhalation pneumopathy.

Had a history of a bleeding disorder.

Had a history of autoimmune disease that may have potentially interfered with study outcomes.

Had an active multisystem disease that may have potentially influenced safety or assessment of study outcomes; including, but not limited to, clinically significant cardiovascular, respiratory, hepatic/biliary, renal, gastrointestinal, endocrine, psychiatric or neurologic disorder.

Had a history of myasthenia gravis or another neurotransmission disease.

Had a neuromuscular disorder that may have potentially interfered with subject outcomes.

Had received any investigational product during the 90 days prior to screening for this study.

Smoked more than 10 cigarettes or equivalent amount of tobacco per day and could not stop smoking while in the CPU.

Had any condition(s) that in the opinion of the Principal Investigator (PI) would compromise the safety of the subject or prevent the subject from completing the study.

Could not communicate reliably with the Investigator.

Subjects who were vegetarians, vegans or had medical dietary restrictions conflicting with the study standardized menus.

Removal of Subjects from Therapy or Assessment

Standard toxicity grading according to the National Cancer Institute Common Terminology Criteria (NCI CTC, version 4.0) was used to grade the AEs. This is owing to the fact that these are the only standardised set of comprehensive criteria available and have proven useful in healthy volunteer Phase I studies. Local laboratory normal values were applied. Abnormal laboratory and other tests were always repeated prior to grading in order to ensure consistency and to exclude technical errors. Diurnal variations in laboratory parameters and other measurements as well as baseline status and conditions (e.g. Gilbert's syndrome) were always taken into account when assessing whether abnormalities constitute a drug related toxicity and when grading, if applicable.

The CTC for AE (CTCAE) displays Grades I through V with detailed clinical descriptions of severity for each AE based on this general guideline. The grade definitions are described as follows:

Grade I: Mild; asymptomatic or mild symptoms; clinical or diagnostic observations only; intervention not indicated.

Grade II: Moderate; minimal, local or non-invasive intervention indicated; limiting age-appropriate instrumental ADL*.

*Instrumental Activities of Daily Living (ADL) refer to preparing meals, shopping for groceries or clothes, using the telephone, managing money, etc.

Grade III: Severe or medically significant but not immediately life-threatening; hospitalization or prolongation of hospitalization indicated; disabling; limiting self care ADL**.

**Self care ADL refer to bathing, dressing and undressing, feeding self, using the toilet, taking medications and not bedridden.

Grade IV: Life-threatening consequences; urgent intervention indicated.

Grade V: Death related to AE.

The CTCAE criteria and their interpretation are consistent with the standard intensity grading for AEs during clinical trials: Grade I: mild, Grade II: moderate, Grade III: severe or medically significant but not immediately life-threatening, may constitute serious adverse event (SAE)/suspected unexpected serious adverse reaction (SUSAR). Grades IV and V constitute SAE/SUSAR.

The study was to be stopped if certain adverse events occurred with a reasonable possibility of a causal relationship with the IMP.

Withdrawal of Subjects

In accordance with the Declaration of Helsinki, subjects could have withdrawn at any time, but once treatment or dosing occurred every attempt was made to continue assessments to ensure the safety of the subject. Specific reasons for withdrawing a subject were:

Voluntary discontinuation by the subject, who was at any time free to discontinue his or her participation in the study.

Severe non-compliance or major deviation from the protocol as judged by the Investigator and/or Sponsor.

Incorrect inclusion, i.e. the subject, with the benefit of hindsight, did not meet the required eligibility criteria for the study at the time of inclusion.

Other reasons as judged by the PI.

Subjects were at any time free to withdraw from the study, without prejudice (withdrawal of consent). Such subjects were always asked about the reason(s) and the presence of any AEs. If possible, subjects who were withdrawn from the study after dosing and before completion of the week 4 visit were to have been seen by the PI or delegate and undergo the assessments and procedures scheduled for the follow-up visit. AEs were to be followed until resolution, return to baseline or stabilization if a non-study related cause had been established, whenever possible.

Replacement of Subjects

The planned number of subjects must have completed each cohort in order to assess the safety and tolerability of a given dose of QM1114-DP or placebo (7 days post treatment). If the number of completed subjects was less than the minimum requirement of a given cohort, in order to make a decision on dose escalation, the sponsor and PI may have decided that these subjects were to be replaced and those subjects were treated and assessed accordingly prior to the next dose escalation.

Treatments

Treatments Administered

Subjects received one treatment of 30 units, 60 units or 90 units of QM1114-DP or placebo of equal volume (100 µl) administered to the LCL region. Each treatment included three injections (one injection per injection site). The position of the injections were adjusted in accordance with the LCL pattern of rhytids for the individual subject. Depending on the pattern of rhytids for individual subjects, if the lines in the LCL region were above and below the lateral canthus, injections were administered as described in FIG. 12A. Alternatively, if the lines in the LCL for the individual subject were primarily below the lateral canthus, injections were administered as described in FIG. 12B. In all cases, the injection points were at the external part of the orbicularis oculi and, when applicable, at about 1-2 cm from the orbital rim.

Assigning Subjects to Treatment Groups

Subjects who signed the informed consent for the study and thereafter underwent screening procedures were identified during this period by their unique RPL ID number (identification number from the RPL volunteer database) and screening number.

Subjects fulfilling the eligibility criteria were assigned subject numbers before dosing in the morning of Day 1. Subject numbers were assigned from 201 to 208 (Cohort 5), 221 to 228 (Cohort 6) and 241 to 248 (Cohort 7). Subject numbers were allocated in consecutive order and corresponded to a number on the computer generated randomization list, which determined the treatment sequence. If a subject discontinued from the study, the subject number was not re-used and the subject was not allowed to re-enter the study.

Selection of Doses

Any new BoNT-A product entering clinical studies for the first time must use the clinical knowledge available for existing products of the same serotype and origin in determining the FIM approaches.

The starting dose for the LCL indication was 5 units per injection (in total 30 units) to be followed by dose escalations (after SRC decisions) to 10 units per injection (in total 60 units) then 15 units per injection (in total 90 units). The maximum dose used in the study for the treatment of LCL was based upon previous studies that examined 15, 30 and 45 units of BoNT administered to each side for the treatment of LCL (totals of 30, 60 and 90 units administered). The incidence of treatment-emergent AEs was similar for all doses studied.

Selection of Timing of Dose

In this study, subjects received one treatment of 30, 60 or 90 units of QM1114-DP or placebo in the morning of Study Day 1.

Study Procedures

For screening, study days and follow-up please refer to Table 12.

All study measurements obtained are described below.

Should there have been any safety concerns based on a review of the safety data for an individual subject, additional vital signs, ECG recordings and/or laboratory safety samples may have been taken. The total volume of blood to be withdrawn during the study should not have exceeded 300 ml per subject.

Vital Signs

Blood Pressure, Heart Rate, Tympanic Temperature and Respiratory Rate

Supine blood pressure (BP) and heart rate (HR) were measured using a semi-automatic BP recording device (Critikon Dinamap® monitors) with an appropriate cuff size. For respiratory rate measurements subjects were required to rest in a supine position for at least 10 minutes prior to respiratory rate measurement. For timings of individual measurements, refer to the Study Flowchart (Table 12). The timings of all measurements performed during the study might have been subject to change based on the ongoing review of safety and tolerability data. Body temperature (tympanic) was measured (a single measurement) in degrees Celsius using an automated thermometer at the times indicated in the Study Flowchart (Table 12). Additional temperature assessments may have been taken for safety at the discretion of the PI or delegate.

ECG Measurements

Triplicate 12-lead ECGs were recorded using a GE Marquette MAC1200@/MAC1200ST® recorder connected via a fixed network connection to the MUSE® Cardiology Information System (MUSE). All ECGs recorded during the study were stored electronically on the MUSE information CRF. If a subject showed an abnormal ECG at any stage, additional safety recordings (including the use of 5 or 12-lead Holter equipment) were to be made and the abnormality followed to resolution if required.

The timings of all measurements performed during the study could have been subject to change based on the ongoing review of safety and tolerability data.

Clinical Laboratory Safety Measurements

Clinical laboratory safety parameters are listed in Table 13, below.

TABLE 13

| Clinical Laboratory Safety Parameters | | | | |
|---|---|---|---|---|
| Biochemistry | Haematology | Urinalysis* | Serogy | Urine Screen for Drugs of Abuse |
| Aspartate aminotransterase (AST) | Red blood cells | Leukocytes | HBsAG | Benzodiazepines |
| | Haemoglobin | Nitrite | Hepats C | Opiates |
| | Haematocrit | Urobilinogen | antibodies | Amphetamines |
| Alanine aminotransferase (ALT) | Mean corpuscular volume | Protein | HiV 1 and 2 | Methadone |
| | | pH | antibodies | Cocaine |
| Alkaline phosphatase (ALP) | Mean corpuscular | Blood Specific | | Cannabinoids |
| | concentration | gravity | | Barbiturates |
| Lactate dehydrogenase (LDH) | White blood cells | Ketones Bilirubin | | |
| Creatine kinase (CK) | Neutrophils Lymphocytes | Glucose | | |
| Gamma glutamyltransferase (Gamma GT) | Monocytes Eosinophils | | | |
| Total bilirubin | Basophils Platelet count | | | |
| Creatinine | | | | |
| Urea | | | | |
| Total Protein | | | | |
| Alburnin | | | | |
| Glucose-fasting | | | | |
| Sodium | | | | |
| Potassium | | | | |
| Calcium | | | | |
| Phosphate | | | | |
| Cholesterol-fasting | | | | |
| Triglycerides-fasting | | | | |
| β-HCGᵃ | | | | |

*If deemed necessary, based on a clinically significant positive urinalysis test, microscopic examination of sediment and/or culture was performed by The Doctors Laboratory (TDL).
[a]Serum β-HCG (beta-human chorionic gonadotrophin) was done at screening and admission.

system. Only ECGs recorded electronically were valid ECGs for any purpose other than safety assessment. ECG printouts were filed in the subject's CRF for medical safety reviews.

If at all possible, the same recorder was used for any one subject. Each ECG recorder was set up to the required technical specifications and containing the information required to identify the records. Each ECG recording was clearly identified (subject ID, scheduled time relative to dose and the actual times of ECG recordings).

12-lead ECG recordings were made at the time-points indicated in the Study Flowchart (Table 12) after the subjects had rested in a supine position for at least 10 minutes. The subjects avoided postural changes during the ECG recordings and clinical staff ensured that subjects were awake during the ECG recording.

All recorded ECG were reviewed by a Research Physician on an ongoing basis and the review was documented in the Haematology and Biochemistry Blood samples for determination of haematology and biochemistry parameters were taken at the times given in the Study Flowchart (Table 12). The date and time of collection was recorded on the appropriate CRF. The analyses were done at TDL, using routine methods. Blood samples for determination of standard haematology parameters were collected in 4 ml K3EDTA tubes and blood samples for determination of standard biochemistry parameters were collected in 5 ml Serum Separator Tubes (SST).

Laboratory values outside the reference limits, which were suspected to be of any clinical significance, were to be repeated. Subjects in whom the suspected clinical significance was confirmed on repeated sampling were either not to be included or, if already included, may have been withdrawn from further participation in the study and/or followed until normalization or for as long as the Investigator or delegate considered it necessary.

Serology

Serology was performed as detailed in the Study Flowchart (Table 12). At the screening visit, all subjects were tested for the parameters listed in Table 13. This was done for the safety of the study personnel and the results from the tests were not entered into the study database. If the subject (s) was (were) found to be positive to any of these tests, he or she would have been referred for further examination and treatment and was not included in the study. The serology tests were analyzed in the same blood sample used for clinical chemistry (collected in a 5 ml SST tube). The samples were analyzed by TDL.

β-HCG

To exclude pregnancy, a serum β-HCG blood sample was performed as described in Table 12 and whenever pregnancy was suspected. Any subject with a positive pregnancy test was to be excluded or withdrawn from the study.

Urinalysis

Urine samples for determination of urinalysis parameters were taken at the times given in the Study Flowchart (Table 12). Urinalysis was performed on the parameters described in Table 13 by RPL using a dipstick method. If deemed necessary, based on a clinically significant positive test, microscopic examination of sediment and/or culture was performed by TDL.

Drugs of Abuse

Urine was tested for the drugs of abuse at RPL at the times described in Table 12. If a subject failed the drug abuse screen, he/she was excluded from the study. A repeat drug screen was only done where methodological reasons were believed to have led to a false positive. Borderline positive results, unless covered by the preceding condition, were to be considered as positive and the subject excluded from the study. If the subject was found to be positive due to medication e.g. flu/cold remedies, a repeat drug screen was performed if the subject was still within the screening window. The results from the tests were not entered into the database.

Alcohol Breath Test

An alcohol breath test was performed using an alcometer (for time-points see Study Flowchart Table 12). The results from this test were not entered into the clinical study database. If a subject had a positive alcohol breath test they would have been excluded from the study.

Physical Examination, Height and Weight

The timing of individual examinations is indicated in the Study Flowchart (Table 12). The physical examination performed at screening and at follow-up (day 28) included a full physical examination of the following: general appearance, skin, head, neck, lymph nodes, thyroid, abdomen, musculo-skeletal, cardiovascular, respiratory and neurological systems.

The physical examination performed on Day −1 was a brief examination that focused on any changes since screening.

Height was measured in centimeters and weight in kilograms. Measurements were taken with subjects wearing light clothing and without shoes using calibrated scales for all measurements. Body mass index (BMI) was calculated from the height and weight.

Focused Physical Examination

A focused physical examination of the eyes and face (see Table 12 for time-points) was performed using a standardized scoring system to monitor local warmth, itching, pain, oedema/induration, erythema and bruising. The scoring system was as follows:

Minor change; or

Moderate change.

Efficacy Assessment

Efficacy assessment was performed at the time-points specified in the Study Flowchart (Table 12).

Investigator and Subject Assessment of Severity of Rhytids

At each visit the investigator and the subject independently rated the severity of the subject's rhytids "at rest" and "at maximum smile". The investigator assessed the rhytids using the MAS LCL dynamic and at rest according to the following grades (using high resolution photographs as a guide to the scale grading):

TABLE 14

| Grade | Severity of LCL |
| --- | --- |
| 0 | None |
| 1 | Mild |
| 2 | Moderate |
| 3 | Severe |
| 4 | Very severe |

Subject's Assessment of Satisfaction

At each post-treatment visit the subject assessed his/her degree of satisfaction with treatment using a 4-point rating scale as follows:

TABLE 15

| Grade | Subject satisfaction |
| --- | --- |
| 0 | Very satisfied |
| 1 | Satisfied |
| 2 | Dissatisfied |
| 3 | Very dissatisfied |

Photography

Standardized Digital Photographs were Taken at the Time-Points Specified in the Study Flowchart (Table 12). The photographs were used only to illustrate the effect of the IMP and were not used to assess efficacy. Subjects were instructed to remove any make-up prior to arrival at the clinic or at the clinic prior to any photography.

The following photographs were taken:

The full face at rest (no smile); and

Photographs of LCL area (one at maximum smile and one at rest).

Sample Collection

Clinical Immunogenicity Assay An assay to measure neutralizing antibodies to QM1114-DP will be developed later. Blood samples were collected at the time-points specified in the Study Flowchart (Table 12) for measurement of antibodies when the assay becomes available.

Adverse Events

The definitions of AEs, adverse drug reactions (ADRs), SAEs and suspected unexpected serious adverse reactions (SUSARs) are given below. It was of the utmost importance that all staff involved in the conduct of the clinical research was familiar with the content of this section.

Definitions

Adverse Event (AE)—An AE is the development of an undesirable medical condition or the deterioration of a preexisting medical condition following or during exposure to a pharmaceutical product, whether or not considered causally related to the product. An undesirable medical condition can be symptoms (e.g. nausea, chest pain), signs (e.g. tachycardia, enlarged liver), or the abnormal results of an investigation (e.g. laboratory findings, ECG). In clinical studies, an AE can include an undesirable medical condition occurring at any time, from the date informed consent was signed until the end of their participation in a study, i.e. the subject has discontinued or alternatively completed the study (Day 28).

The causality of AEs (i.e. their relationship to study treatment) was assessed by the Investigator(s) who, in completing the relevant case report form, must answer "yes" or "no" to the question "Do you consider that there is a reasonable possibility that the event may have been caused by any of the following—study medication—other medication?".

Note that SAEs which could be associated with any study procedure were also to be reported.

Adverse Drug Reaction (ADR)—An ADR is any AE where a causal relationship with the IMP is at least a reasonable possibility.

Serious Adverse Event (SAE)—An SAE is an AE occurring during any study phase (i.e., run-in, treatment, washout and/or follow-up) and at any dose of the IMP or placebo, that fulfils one or more of the following criteria:

Results in death.

Is life-threatening.

Requires in-patient hospitalization or prolongation of existing hospitalization.

Results in persistent or significant disability or incapacity.

Is a congenital abnormality or birth defect.

Is an important medical event that may jeopardize the subject or may require medical intervention to prevent one of the outcomes listed above.

The causality of SAEs (i.e. their relationship to study treatment) was assessed in the same way as for non-serious AEs. Note that SAEs which could be associated with any study procedure were also to be reported.

mean, SD, minimum, median and maximum) by time-point and treatment group at rest and at maximum smile separately.

Change from baseline in Investigator and subject assessments of severity of rhytid scales, at rest and at maximum frown/smile, separately, were evaluated using repeated measures model (mixed model). The analysis was performed using SAS PROC MIXED. The mixed model included treatment, time, treatment and time interaction as fixed effects, and baseline measurements as covariate. The time was used as a repeated effect in the model and subject identified groups of correlated data. Baseline was defined as Day −1.

Based on the mixed model, the Least Squares means for each dose group on different days, and the differences between different doses at different days together with 95% confidence interval were presented.

sample size of n=8 subjects per cohort was considered to be sufficient for the determination of safety and tolerability of single doses of QM1114-DP for the temporary improvement of facial lines of the LCL region in healthy male and female subjects.

Study Subjects

For this study, 24 healthy subjects, 6 males and 18 females were randomized and dosed according to the CSP. All have completed the study and were analyzed for safety and efficacy.

Descriptive statistics for demography parameters are presented in Table 16 below. Twenty three (23) subjects were Caucasian and one was Black African with a mean age per cohort ranging between 42.2 and 51.0 years (inclusive). Eighteen (18) subjects were female and 6 were male. The mean weight ranged between 66.8-71.7 kg and BMI was on average between 24.0-26.4 $kg/m^2$ for all subjects. At the entry to the study, there were no existing clinically significant findings in the subjects' medical or surgical history. There were also no remarkable findings in the physical examination for individual subjects during the study.

TABLE 16

| | | QM1114-DP | | | |
|---|---|---|---|---|---|
| Variable | Summary | Cohort 5 30 units | Cohort 6 60 units | Cohort 7 90 units | Placebo |
| n | Statistics | 6 | 6 | 6 | 6 |
| Age (years) | Mean ± SD | 42.2 ± 10.43 | 47.3 ± 6.02 | 51.0 ± 4.69 | 51.0 ± 9.69 |
| | Median (min; max) | 43.5 (28; 54) | 47.0 (40; 55) | 51.0 (44; 56) | 52.5 (34; 63) |
| Height (cm) | Mean ± SD | 169.5 ± 6.53 | 169.0 ± 8.36 | 164.5 ± 8.68 | 163.0 ± 4.73 |
| | Median (min; max) | 166.5 (164; 180) | 167.5 (159; 184) | 165.5 (153; 175) | 163.0 (155; 169) |
| Weight (kg) | Mean ± SD | 69.3 ± 10.25 | 71.7 ± 5.36 | 71.5 ± 9.67 | 66.8 ±15.99 |
| | Median (min; max) | 66.3 (58.1; 83.3) | 70.3 (66.9; 81.4) | 74.0 (53.0; 79.8) | 59.2 (53.4; 94.7) |
| BMI ($kg/m^2$) | Mean ± SD | 24.0 ± 2.22 | 25.1 ± 1.15 | 26.4 ± 2.15 | 25.1 ± 6.01 |
| | Median (min; max) | 24.5 (19.9; 26.0) | 25.1 (23.7; 26.8) | 26.3 (22.6; 29.0) | 22.3 (19.9; 36.1) |

Suspected Unexpected Serious Adverse Reaction (SUSAR)—A SUSAR is any SAE where a causal relationship with the IMP is at least a reasonable possibility, but is not listed in the Investigator's Brochure and/or Summary of Product Characteristics.

Appropriateness of Measurements

All efficacy and safety measures used in this study were standard, widely used and recognized as reliable and accurate.

Efficacy Data Analysis

Efficacy was evaluated using validated 5-point MAS and a rating scale for subjects' assessment of satisfaction. Efficacy data were summarized using descriptive statistics (n, Efficacy Evaluation The efficacy analysis set consisted of all subjects (24 subjects) who received a single dose of QM1114-DP or Placebo and for whom post-dose efficacy data existed.

One of the objectives of this study was to assess the efficacy of QM1114-DP at each dose level for the temporary improvement of facial lines of the lateral canthal region. FIG. 13 and FIG. 14 show the mean rhytid scores of the left and right canthal region by treatment group over time by Investigator and subject at rest and at maximum smile. Modelled statistics by dose group of Investigator's and subject's evaluation of the severity of rhytids at rest and at maximum smile are presented in Table 17 to Table 20. Efficacy was evaluated using the validated MAS for Investigator's and subject's assessments of severity of rhytids. The scales used the following grades for the severity: 0 (none), 1 (mild), 2 (moderate), 3 (severe) and 4 (very severe).

Severity of Rhytids at Rest

The efficacy data showed that following administration of QM1114-DP, the LCL severity at rest decreased in the active treatment groups as assessed by the Investigator and subject in comparison to the placebo treatment group (FIG. 13 and FIG. 14). Changes in rhytid severity were apparent from Day 2 for the 30 and 60 unit QM1114-DP dose levels for LCL.

For the 90 unit QM1114-DP dose level the reduction in rhytid severity began between Day 3 and Day 7. Investigator's assessment of rhytid severity indicated that the maximum effect at rest was reached between Day 21 and Day 28 for the dose levels. Where the maximum effect was reached at Day 21 the effect was maintained up to Day 28. For subject's assessment of rhytid severity the maximum effect was reached sooner. This was seen for rhytid severity of the left LCL region. Subject's assessment of rhytid severity of the left region showed that for the 30 and 90 unit QM1114-DP dose levels, the maximum effect was reached on Day 14 (mean score of 0.7 [30 unit QM1114-DP] and 1.0 [90 unit QM1114-DP] on the MAS). The maximum effect for the 60 unit QM1114-DP dose level was reached at Day 7 (mean score of 0.5 on the MAS) and this effect was maintained up to Day 28. By Day 28, subjects in the 30 unit QM1114-DP treatment group had a mean score of 0.7 on the MAS and subjects in the 60 unit QM1114-DP treatment group had a mean score of between 0.2-0.8 on the MAS. By Day 28 subjects in the 90 unit QM1114-DP treatment group had mean MAS values between 0.8-1.0.

Severity of Rhytids at Maximum Smile

Similar trends of decrease were also observed for Investigator and subject assessment of LCL severity at maximum smile (FIG. 13 and FIG. 14). At maximum smile, the severity of LCL as assessed by the Investigator in the active treatment groups decreased from Day 2 (FIG. 13). A similar pattern was also observed with subject's assessment of rhytid severity (FIG. 14). For the 30 unit QM1114-DP dose level the maximum effect (mean score of 1.0 on the MAS) as assessed by the Investigator was reached at Day 14. The maximum effect for the 60 unit QM1114-DP dose level was reached at Day 7 (mean score of 0.7 [left LCL] and 0.8 [right LCL] on the MAS) and there was still some effect up to Day 28 (mean score of 1.0 [left LCL] and 0.8 [right LCL] on the MAS). The maximum effect for the 90 unit QM1114-DP dose level was reached at Day 7 (mean score of 1.3 [left LCL] on the MAS) and Day 21 (mean score of 1.2 [right LCL] on the MAS). This trend was also observed for subject assessment of rhytid severity except that for all subjects the maximum effect (mean score between 0.7-1.5 on the MAS) was reached on Day 28. By Day 28, subjects in the 30 unit QM1114-DP treatment group had a mean score of 1.0 on the MAS and subjects in the 60 unit QM1114-DP treatment group had a mean score of between 0.7-1.0 on the MAS. By Day 28 subjects in the 90 unit QM1114-DP treatment group had mean MAS score values between 1.2-1.5.

Subject's Assessment of Satisfaction

At each post-treatment visit, the subject assessed his/her degree of satisfaction with treatment using a four point rating scale. The scale used the following grades for satisfaction: 0 (very satisfied), 1 (satisfied), 2 (dissatisfied) and 3 (very dissatisfied).

The Subject's Assessment of Satisfaction Showed that, with the Exception of One Subject (subject 208 on Day 2) in the 30 unit QM1114-DP treatment group who was dissatisfied and one subject (subject 246 on Day 7 and 14) in the 90 unit treatment group who was very dissatisfied with treatment, all subjects in the 30, 60 and 90 unit QM1114-DP treatment groups were either very satisfied or satisfied with treatment from Day 2 to Day 28. In the placebo treatment group, 2 to 3 subjects were either very dissatisfied or dissatisfied with treatment on each study visit from Day 2 to Day 28. The highest proportion of subjects (50%) that were either very dissatisfied or dissatisfied with placebo treatment were observed on Day 2, Day 3 and Day 21.

Mixed Model Analysis

Change from baseline in Investigator and subject's assessments of severity of rhytids scales, at rest and at maximum smile, separately, were evaluated using the repeated measures model (mixed model). The Investigator's evaluation of the severity of rhytids (difference between different doses at different days) are presented in Tables 17-18 (at rest and at maximum smile). The subject's evaluation of the severity of rhytids (difference between different doses at different days) are presented in Tables 19-20 (at rest and at maximum smile). The variable analysed and presented in this section is change from baseline in Investigator and subject's assessments of severity of rhytids scales, at rest and at maximum smile, separately.

The Investigator's evaluation of rhytids of the left and right lateral canthal regions at maximum smile showed that from Day 3 to Day 28 the change from baseline in mean MAS scores in the 30, 60 and 90 unit QM1114-DP treatment groups showed a statistically significant difference (P≤0.05) when compared to scores in the placebo treatment group (Table 17). For the subject's evaluation of rhytids of the left and right side of the face at maximum smile (Table 19), statistically significant differences (P≤0.05) from placebo were reported from Day 3 or week 1 to Day 28 for the 30 and 60 unit QM1114-DP treatment groups. In contrast, no statistically significant scores were reported when the 90 unit QM1114-DP treatment group was compared to scores in the placebo treatment group for left LCL. However, a statistically significant result was reported for right LCL at Day 28 (P=0.012) when the 90 unit QM1114-DP treatment group was compared to placebo.

The Investigator's evaluation of rhytids of the lateral canthal region at rest showed that LCL (left and right side) scores from week 1 to week 4 (Day 28) in the 30 unit QM1114-DP treatment group showed statistical significance (P<0.05) when compared to scores in the placebo treatment group. With the exception of Day 28 (left LCL), similar results from week 1 to week 4 were also reported for the 60 unit QM1114-DP treatment group. Scores from Day 3 (right LCL) or week 1 (left LCL) up to week 4 were also statistically different (P<0.05) in comparison to placebo scores for the maximum dose level (90 unit QM1114-DP treatment group) (Table 18).

For the subjects evaluation of rhytids at rest, scores were statistically significant (P≤0.05) from Day 3 to Day 28 in both the 30 unit and 60 unit QM1114-DP treatment groups when compared to scores in the placebo group for LCL on the right side (Table 20B). With the exception of Day 3 (60 unit QM1114-DP treatment group) and week 1 (30 unit QM1114-DP treatment group), statistically significant scores from Day 3 to Day 28 were also seen in both the 30 unit and 60 unit QM1114-DP treatment groups when compared to scores in the placebo group for LCL on the left side (Table 20A). For the 90 unit QM1114-DP treatment group the results varied. For LCL on the right side of the face, statistically significant scores in rhytid severity were observed from Day 14 to Day 28 (Table 20B). In contrast, for left LCL, statistically significant scores in comparison to placebo were only observed on Day 14 and Day 28.

TABLE 17

Severity of Rhytids: Investigator's Evaluation at Maximum Smile: Difference between QM1114-DP Doses and Placebo in Change from Baseline-Mixed Model (A, LCL indication [left]; B, LCL indication [right]

MAXIMUM SMILE

| Comparison | Visit | Difference in Means* | P-values | 95% Confidence Interval Lower Limit | Upper Limit |
|---|---|---|---|---|---|
| A: Indication: LCL (left), maximum smile, Investigator's evaluation | | | | | |
| QM11114-DP 30 units- | Day 2 | −0.18 | 0.6391 | −0.96 | 0.59 |
| Pooled Placebo | Day 3 | −1.18 | 0.0030 | −1.96 | −0.41 |
| | Day 7 | −1.52 | 0.0002 | −2.29 | −0.74 |
| | Day 14 | −1.35 | 0.0008 | −2.13 | −0.58 |
| | Day 21 | −1.52 | 0.0002 | −2.29 | −0.74 |
| | Day 28 | −1.52 | 0.0002 | −2.29 | −0.74 |
| | Overall | −1.21 | <0.0001 | −1.54 | −0.89 |
| QM11114-DP 60 units- | Day 2 | −0.44 | 0.2636 | −1.22 | 0.34 |
| Pooled Placebo | Day 3 | −1.28 | 0.0016 | −2.06 | −0.50 |
| | Day 7 | −2.28 | <.0001 | −3.03 | −1.50 |
| | Day 14 | −1.44 | 0.0004 | −2.22 | −0.66 |
| | Day 21 | −2.11 | <0.0001 | −2.89 | −1.33 |
| | Day 28 | −1.61 | <0.0001 | −2.39 | −0.83 |
| | Overall | −1.53 | <0.0001 | −1.86 | −1.19 |
| QM11114-DP 90 units- | Day 2 | −0.35 | 0.3719 | −1.13 | 0.42 |
| Pooled Placebo | Day 3 | −0.85 | 0.0317 | −1.63 | −0.08 |
| | Day 7 | −1.52 | 0.0002 | −2.29 | −0.74 |
| | Day 14 | −0.68 | 0.0830 | −1.46 | 0.09 |
| | Day 21 | −1.35 | 0.0008 | −2.13 | −0.58 |
| | Day 28 | −1.18 | 0.0030 | −1.96 | −0.41 |
| | Overall | −0.99 | <0.0001 | −1.31 | −0.66 |
| B: Indication: LCL (right), maximum smile, Investigator's evaluation | | | | | |
| QM11114-DP 30 units- | Day 2 | −0.33 | 0.3850 | −1.08 | 0.42 |
| Pooled Placebo | Day 3 | −1.16 | 0.0026 | −1.91 | −0.41 |
| | Day 7 | −1.50 | 0.0001 | −2.24 | −0.75 |
| | Day 14 | −1.33 | 0.0006 | −2.08 | −0.58 |
| | Day 21 | −1.50 | 0.0001 | −2.24 | −0.75 |
| | Day 28 | −1.33 | 0.0006 | −2.08 | −0.58 |
| | Overall | −1.19 | <0.0001 | −1.50 | −0.88 |
| QM11114-DP 60 units- | Day 2 | −0.41 | 0.2825 | −1.16 | 0.34 |
| Pooled Placebo | Day 3 | −1.41 | 0.0003 | −2.16 | −0.66 |
| | Day 7 | −2.08 | <0.0001 | −2.83 | −1.32 |
| | Day 14 | −1.58 | <0.0001 | −2.33 | −0.82 |
| | Day 21 | −1.91 | <0.0001 | −2.66 | −1.16 |
| | Day 28 | −1.58 | <0.0001 | −2.33 | −0.82 |
| | Overall | −1.49 | <0.0001 | −1.82 | −1.17 |
| QM11114-DP 90 units- | Day 2 | −0.16 | 0.6674 | −0.91 | 0.59 |
| Pooled Placebo | Day 3 | −1.00 | 0.0095 | −1.74 | −0.25 |
| | Day 7 | −1.33 | 0.0006 | −2.08 | −0.58 |
| | Day 14 | −0.83 | 0.0301 | −1.58 | −0.08 |
| | Day 21 | −1.50 | 0.0001 | −2.24 | −0.75 |
| | Day 28 | −1.16 | 0.0026 | −1.91 | −0.41 |
| | Overall | −1.00 | <0.0001 | −1.31 | −0.68 |

TABLE 18

Severity of Rhytids: Investigator's Evaluation at Rest: Difference between QM1114-DP Doses and Placebo in Change from Baseline—Mixed Model (A, LCL indication [left]; B, LCL indication [right])
REST

| Comparison | Visit | Difference in Means* | P-values | 95% Confidence Interval Lower Limit | 95% Confidence Interval Upper Limit |
|---|---|---|---|---|---|
| A: Indication: LCL (left), rest, Investigators evaluation | | | | | |
| QM1114-DP 30 units—Pooled Placebo | Day 2 | 0.14 | 0.6705 | -0.51 | 0.80 |
| | Day 3 | -0.53 | 0.1148 | -1.18 | 0.13 |
| | Day 7 | -0.66 | 0.0106 | -1.51 | -0.20 |
| | Day 14 | -0.69 | 0.0385 | -1.35 | -0.04 |
| | Day 21 | -1.03 | 0.0024 | -1.68 | -0.37 |
| | Day 28 | -0.69 | 0.0385 | -1.35 | -0.04 |
| | Overall | -0.61 | <.0001 | -0.89 | -0.33 |
| OM1114-DP 60 units—Pooled Placebo | Day 2 | -0.14 | 0.6623 | -0.80 | 0.51 |
| | Day 3 | -0.14 | 0.6623 | -0.80 | 0.51 |
| | Day 7 | -1.14 | 0.0007 | -1.80 | -0.49 |
| | Day 14 | -0.98 | 0.0036 | -1.63 | -0.33 |
| | Day 21 | -1.48 | <.0001 | -2.13 | -0.83 |
| | Day 28 | -0.64 | 0.0528 | -1.30 | 0.01 |
| | Overall | -0.76 | <.0001 | -1.03 | -0.48 |
| QM1114-DP 90 units—Pooled Placebo | Day 2 | 0.17 | 0.6116 | -0.81 | 0.48 |
| | Day 3 | 0.00 | 1.0000 | -0.65 | 0.65 |
| | Day 7 | -0.67 | 0.0439 | -1.31 | -0.02 |
| | Day 14 | -0.83 | 0.0122 | -1.48 | -0.19 |
| | Day 21 | -1.00 | 0.0028 | -1.65 | -0.35 |
| | Day 28 | -1.00 | 0.0028 | -1.65 | -0.35 |
| | Overall | -0.61 | <.0001 | -0.88 | -0.35 |
| B: Indication: LCL (right), rest, Investigator's evaluation | | | | | |
| QM1114-DP 30 units—Pooled Placebo | Day 2 | 0.14 | 0.6786 | -0.52 | 0.80 |
| | Day 3 | -0.36 | 0.2844 | -1.02 | 0.30 |
| | Day 7 | -1.03 | 0.0027 | -1.69 | -0.36 |
| | Day 14 | -0.86 | 0.0115 | -1.52 | -0.20 |
| | Day 21 | -1.19 | 0.0005 | -1.86 | -0.53 |
| | Day 28 | -0.69 | 0.0407 | -1.36 | -0.03 |
| | Overall | -0.67 | <.0001 | -0.95 | -0.38 |
| QM1114-DP 60 units—Pooled Placebo | Day 2 | -0.15 | 0.6638 | -0.81 | 0.52 |
| | Day 3 | -0.15 | 0.6638 | -0.81 | 0.52 |
| | Day 7 | -1.15 | 0.0008 | -1.81 | -0.48 |
| | Day 14 | -1.15 | 0.0008 | -1.81 | -0.48 |
| | Day 21 | -1.31 | 0.0001 | -1.97 | -0.65 |
| | Day 28 | -0.81 | 0.0165 | -1.47 | -0.15 |
| | Overall | -0.78 | <.0001 | -1.06 | -0.51 |
| QM1114-DP 90 units—Pooled Placebo | Day 2 | -0.00 | 1.0000 | -0.66 | 0.66 |
| | Day 3 | -0.67 | 0.0469 | -1.32 | -0.01 |
| | Day 7 | -0.83 | 0.0134 | -1.49 | -0.18 |
| | Day 14 | -1.00 | 0.0032 | -1.66 | -0.34 |
| | Day 21 | -0.83 | 0.0134 | -1.49 | -0.18 |
| | Day 28 | -1.00 | 0.0032 | -1.66 | -0.34 |
| | Overall | -0.72 | <.0001 | -0.99 | -0.45 |

TABLE 19

Severity of Rhytids: Subject's Evaluation at Maximum Smile: Difference between QM1114-DP Doses and Placebo in Change from Baseline—Mixed Model (A, LCL indication [left]; B, LCL indication [right])
MAXIMUM SMILE

| Comparison | Visit | Difference in Means* | P-values | 95% Confidence Interval Lower Limit | 95% Confidence Interval Upper Limit |
|---|---|---|---|---|---|
| A: Indication: LCL (left), maximum smile, Subject's evaluation | | | | | |
| QM1114-DP 30 units—Pooled | Day 2 | -0.28 | 0.5422 | -1.20 | 0.63 |
| | Day 3 | -0.95 | 0.0424 | -1.87 | -0.03 |

TABLE 19-continued

Severity of Rhytids: Subject's Evaluation at Maximum Smile: Difference between QM1114-DP Doses and Placebo in Change from Baseline—Mixed Model (A, LCL indication [left]; B, LCL indication [right])
MAXIMUM SMILE

| Comparison | Visit | Difference in Means* | P-values | 95% Confidence Interval Lower Limit | 95% Confidence Interval Upper Limit |
|---|---|---|---|---|---|
| Placebo | Day 7 | -1.12 | 0.0174 | -2.03 | -0.20 |
| | Day 14 | -1.45 | 0.0022 | -2.37 | -0.53 |
| | Day 21 | -1.12 | 0.0174 | -2.03 | -0.20 |
| | Day 28 | -1.12 | 0.0174 | -2.03 | -0.20 |
| | Overall | -1.01 | <.0001 | -1.38 | -0.63 |
| QM1114-DP 60 units—Pooled Placebo | Day 2 | -0.33 | 0.4845 | -1.25 | 0.59 |
| | Day 3 | -0.33 | 0.4845 | -1.25 | 0.59 |
| | Day 7 | -0.99 | 0.0347 | -1.91 | -0.07 |
| | Day 14 | -1.33 | 0.0051 | -2.25 | -0.41 |
| | Day 21 | -0.83 | 0.0780 | -1.75 | 0.09 |
| | Day 28 | -1.16 | 0.0140 | -2.08 | -0.24 |
| | Overall | -0.83 | <.0001 | -1.21 | -0.44 |
| QM1114-DP 90 units—Pooled Placebo | Day 2 | -0.12 | 0.8022 | -1.03 | 0.80 |
| | Day 3 | 0.22 | 0.6397 | -0.70 | 1.13 |
| | Day 7 | -0.12 | 0.8022 | -1.03 | 0.80 |
| | Day 14 | -0.45 | 0.3333 | -1.37 | 0.47 |
| | Day 21 | -0.28 | 0.5422 | -1.20 | 0.63 |
| | Day 28 | -0.62 | 0.1856 | -1.53 | 0.30 |
| | Overall | -0.23 | 0.2383 | -0.61 | 0.15 |
| B: Indication: LCL (right), maximum smile, Subject's evaluation | | | | | |
| QM1114-DP 30 units—Pooled Placebo | Day 2 | -0.11 | 0.7955 | -0.98 | 0.75 |
| | Day 3 | -1.11 | 0.0119 | -1.98 | -0.25 |
| | Day 7 | -1.28 | 0.0040 | -2.14 | -0.42 |
| | Day 14 | -1.45 | 0.0012 | -2.31 | -0.58 |
| | Day 21 | -1.45 | 0.0012 | -2.31 | -0.58 |
| | Day 28 | -1.45 | 0.0012 | -2.31 | -0.58 |
| | Overall | -1.14 | <.0001 | -1.50 | -0.78 |
| QM1114-DP 60 units—Pooled Placebo | Day 2 | -0.33 | 0.4515 | -1.20 | 0.54 |
| | Day 3 | -1.00 | 0.0244 | -1.86 | -0.13 |
| | Day 7 | -1.16 | 0.0089 | -2.03 | -0.30 |
| | Day 14 | -1.00 | 0.0244 | -1.86 | -0.13 |
| | Day 21 | -1.00 | 0.0244 | -1.86 | -0.13 |
| | Day 28 | -1.50 | 0.0008 | -2.36 | -0.63 |
| | Overall | -1.00 | <.0001 | -1.36 | -0.63 |
| QM1114-DP 90 units—Pooled Placebo | Day 2 | 0.05 | 0.9024 | -0.81 | 0.92 |
| | Day 3 | -0.45 | 0.3075 | -1.31 | 0.42 |
| | Day 7 | -0.45 | 0.3075 | -1.31 | 0.42 |
| | Day 14 | -0.45 | 0.3075 | -1.31 | 0.42 |
| | Day 21 | -0.78 | 0.0760 | -1.64 | 0.08 |
| | Day 28 | -1.11 | 0.0119 | -1.98 | -0.25 |
| | Overall | -0.53 | 0.0040 | -0.89 | -0.17 |

TABLE 20

Severity of Rhytids: Subject's Evaluation at Rest: Difference between QM1114-DP Doses and Placebo in Change from Baseline—Mixed Model (A, LCL indication [left]; B, LCL indication [right])
REST

| Comparison | Visit | Difference in Means* | P-values | 95% Confidence Interval Lower Limit | 95% Confidence Interval Upper Limit |
|---|---|---|---|---|---|
| A: Indication: LCL (left rest, Subjects evaluation | | | | | |
| QM114-DP 30 units—Pooled Placebo | Day 2 | -0.58 | 0.1189 | -1.32 | 0.15 |
| | Day 3 | -0.92 | 0.0149 | -1.65 | -0.18 |
| | Day 7 | -0.58 | 0.1189 | -1.32 | 0.15 |
| | Day 14 | -1.08 | 0.0042 | -1.82 | -0.35 |
| | Day 21 | -0.92 | 0.0149 | -1.65 | -0.18 |

TABLE 20-continued

Severity of Rhytids: Subject's Evaluation at Rest: Difference between QM1114-DP Doses and Placebo in Change from Baseline—Mixed Model (A, LCL indication [left]; B, LCL indication [right])

REST

| Comparison | Visit | Difference in Means* | P-values | 95% Confidence Interval Lower Limit | Upper Limit |
|---|---|---|---|---|---|
| | Day 28 | −1.08 | 0.0042 | −1.82 | −0.35 |
| | Overall | −0.86 | <.0001 | −1.16 | −0.55 |
| QM1114-DP 60 | Day 2 | −0.34 | 0.3679 | −1.07 | 0.40 |
| units—Pooled | Day 3 | −0.67 | 0.0741 | −1.40 | 0.07 |
| Placebo | Day 7 | −0.84 | 0.0263 | −1.57 | −0.10 |
| | Day 14 | −0.84 | 0.0263 | −1.57 | −0.10 |
| | Day 21 | −0.84 | 0.0263 | −1.57 | −0.10 |
| | Day 28 | −1.00 | 0.0080 | −1.74 | −0.27 |
| | Overall | −0.75 | <.0001 | −1.06 | −0.45 |
| QM114-DP 90 | Day 2 | −0.42 | 0.2645 | −1.15 | 0.32 |
| units—Pooled | Day 3 | −0.25 | 0.5033 | −0.98 | 0.49 |
| Placebo | Day 7 | 0.08 | 0.8202 | −0.65 | 0.82 |
| | Day 14 | −0.75 | 0.0456 | −1.48 | −0.01 |
| | Day 21 | −0.25 | 0.5033 | −0.98 | 0.49 |
| | Day 28 | −0.75 | 0.0456 | −1.48 | −0.01 |
| | Overall | −0.39 | 0.0119 | −0.69 | −0.09 |

B: Indication: LCL (right), rest, Subjects evaluation

| Comparison | Visit | Difference in Means* | P-values | Lower Limit | Upper Limit |
|---|---|---|---|---|---|
| QM1114-DP 30 | Day 2 | −0.42 | 0.2317 | −1.10 | 0.27 |
| units—Pooled | Day 3 | −0.92 | 0.0093 | −1.60 | −0.23 |
| Placebo | Day 7 | −1.08 | 0.0022 | −1.77 | −0.40 |
| | Day 14 | −1.08 | 0.0022 | −1.77 | −0.40 |
| | Day 21 | −1.58 | <.0001 | −2.27 | −0.90 |
| | Day 28 | −1.25 | 0.0005 | −1.94 | −0.56 |
| | Overall | −1.06 | <.0001 | −1.34 | −0.77 |
| QM1114-DP 60 | Day 2 | −0.67 | 0.0572 | −1.35 | 0.02 |
| units—Pooled | Day 3 | −1.00 | 0.0047 | −1.69 | −0.31 |
| Placebo | Day 7 | −1.00 | 0.0047 | −1.69 | −0.31 |
| | Day 14 | −1.00 | 0.0047 | −1.69 | −0.31 |
| | Day 21 | −1.17 | 0.0010 | −1.85 | −0.48 |
| | Day 26 | −1.50 | <.0001 | −2.19 | −0.81 |
| | Overall | −1.06 | <.0001 | −1.34 | −0.77 |
| QM1114-DP 90 | Day 2 | 0.08 | 0.8104 | −0.60 | 0.77 |
| units—Pooled | Day 3 | −0.25 | 0.4721 | −0.94 | 0.44 |
| Placebo | Day 7 | −0.42 | 0.2317 | −1.10 | 0.27 |
| | Day 14 | −0.92 | 0.0093 | −1.60 | −0.23 |
| | Day 21 | −0.92 | 0.0093 | −1.60 | −0.23 |
| | Day 28 | −0.92 | 0.0093 | −1.60 | −0.23 |
| | Overall | −0.56 | 0.0007 | −0.84 | −0.27 |

Efficacy Conclusions

With the exception of the subject assessment of LCL (90 unit QM1114-DP treatment group), the efficacy results as measured by the Investigator's and subject's assessment of LCL at maximum smile clearly demonstrated that QM1114-DP is efficacious in reducing LCL severity at maximum smile in comparison to those subjects evaluated in the placebo treatment group. The reduction in rhytid severity was maintained up to follow-up (Day 28). Similarly, at rest the reduction of LCL severity was greater in the active treatment groups, as assessed by the Investigator and subject, than in the placebo treatment group with some exceptions. The subject's assessment of LCL satisfaction showed that, with the exception of two subjects, all subjects in active treatment groups were either very satisfied or satisfied with treatment through to Day 28. In the placebo treatment group, at most 50% of the subjects were dissatisfied or very dissatisfied with treatment.

Safety Evaluation

The safety analysis included all 24 subjects who had received a single dose of randomized study medication.

Six subjects received 30 units of QM1114-DP, six subjects received 60 units of QM1114-DP and six subjects received the maximum dose of 90 units. Six subjects received placebo treatment.

For the purposes of AE analysis, this section primarily deals with those AEs that were treatment emergent, i.e. commencing after dosing with the IMP and ADRs i.e. where a causal relationship with the IMP was at least a reasonable possibility. There were no SAEs reported during the study, no SUSAR and no subject was withdrawn from the study due to safety reasons.

An overview of AEs by treatment group is presented in Table 21 AEs were reported for each dose level. Forty four (44) AEs were reported in 18 of 24 (75.0%) subjects of which 31 AEs in 15 of 24 (62.5%) subjects overall were judged by the Investigator to be possibly or probably treatment related. Fourteen (14) AEs were reported in 5 of 6 subjects for 30 units of QM1114-DP, nine AEs reported in 5 of 6 subjects for 60 units of QM1114-DP and 14 AEs reported for 3 of 6 (50.0%) subjects at the maximum dose level (90 units of QM1114-DP). For the placebo treatment group, seven AEs were reported in 5 of 6 subjects. An overview of AEs by SOC assignments and PT is presented in Table 22. Related AEs by SOC assignments and PT are presented in Table 23.

TABLE 21

Summary of AEs

| | QM1114-DP 30 units (N = 6) | | | QM1114-DP 60 units (N = 6) | | | QM1114-DP 90 units (N = 6) | | | Pooled Placebo N = 6 | | |
|---|---|---|---|---|---|---|---|---|---|---|---|---|
| | E | N | % | E | N | % | E | N | % | E | N | % |
| Total number of AEs | 14 | 5 | 83.3 | 9 | 5 | 83.3 | 14 | 3 | 50.0 | 7 | 5 | 83.3 |
| Total number of serious AEs | 0 | 0 | 0 | 0 | 0 | 0 | 0 | 0 | 0 | 0 | 0 | 0 |
| Total number of treatment related AEs | 10 | 4 | 83.3 | 6 | 4 | 66.7 | 9 | 3 | 50.0 | 6 | 4 | 66.7 |
| Total number of treatment related SAEs | 0 | 0 | 0 | 0 | 0 | 0 | 0 | 0 | 0 | 0 | 0 | 0 |
| Total number of subjects with AEs leading to withdrawal | — | 0 | — | — | 0 | — | — | 0 | — | — | 0 | — |
| Subjects with at least one mild AE | — | 5 | 83.3 | — | 5 | 83.3 | — | 3 | 50.0 | — | 5 | 83.3 |
| Related AE | — | 4 | 66.7 | — | 4 | 66.7 | — | 3 | 50.0 | — | 4 | 66.7 |
| Unrelated AE | — | 3 | 50.0 | — | 2 | 33.3 | — | 2 | 33.3 | — | 1 | 16.7 |
| Subjects with at least one moderate AE | — | 0 | 0.0 | — | 0 | 0.0 | — | 1 | 16.7 | — | 0 | 0.0 |
| Related AE | — | 0 | 0.0 | — | 0 | 0.0 | — | 1 | 16.7 | — | 0 | 0.0 |
| Unrelated AE | — | 0 | 0.0 | — | 0 | 0.0 | — | 0 | 0.0 | — | 0 | 0.0 |
| Subjects with at least one severe AE | — | 0 | 0.0 | — | 0 | 0.0 | — | 0 | 0.0 | — | 0 | 0.0 |
| Related AE | — | 0 | 0.0 | — | 0 | 0.0 | — | 0 | 0.0 | — | 0 | 0.0 |

TABLE 21-continued

| | | | | | | | | | | | | |
|---|---|---|---|---|---|---|---|---|---|---|---|---|
| | Summary of AEs | | | | | | | | | | | |
| | QM1114-DP | | | | | | | | | Pooled | | |
| | 30 units (N = 6) | | | 60 units (N = 6) | | | 90 units (N = 6) | | | Placebo N = 6 | | |
| | E | N | % | E | N | % | E | N | % | E | N | % |
| Unrelated AE | — | 0 | 0.0 | — | 0 | 0.0 | — | 0 | 0.0 | — | 0 | 0.0 |
| Subjects with At least one ADR | — | 4 | 66.7 | — | 4 | 66.7 | — | 3 | 50.0 | — | 4 | 66.7 |
| Subjects with at least one SUSAR | — | 0 | 0.0 | — | 0 | 0.0 | — | 0 | 0.0 | — | 0 | 0.0 |

E = Number of events; N = number of subjects.

TABLE 22

Summary of Subjects with AEs Categorised by System Organ Class, Preferred Term and Treatment

| SYSTEM ORGAN CLASS*/PREFERRED TERM** | QM1114-DP | | | |
|---|---|---|---|---|
| | 30 units N = 6 | 60 units N = 6 | 90 units N = 6 | Placebo N = 6 |
| TOTAL NUMBER OF SUBJECTS WITH AEs | 5 | 5 | 3 | 5 |
| EAR AND LABYRINTH DISORDERS | 0 | 0 | 1 | 0 |
| Ear congestion | 0 | 0 | 1 | 0 |
| EYE DISORDERS | 1 | 0 | 1 | 1 |
| Asthenopia | 0 | 0 | 1 | 0 |
| Eye pruritus | 1 | 0 | 0 | 0 |
| Lacrimation increased | 0 | 0 | 0 | 1 |
| GENERAL DISORDERS AND ADMINISTRATION SITE CONDITIONS | 1 | 3 | 2 | 2 |
| Application site bruise | 0 | 0 | 0 | 1 |
| Influenza like illness | 1 | 0 | 0 | 0 |
| Injection site bruising | 0 | 0 | 1 | 0 |
| Injection site erythema | 0 | 2 | 0 | 1 |
| Injection site pain | 0 | 1 | 0 | 0 |
| Sensation of pressure | 0 | 0 | 2 | 1 |
| INJURY, POISONING AND PROCEDURAL COMPLICATIONS | 0 | 0 | 1 | 0 |
| Animal scratch | 0 | 0 | 1 | 0 |
| INVESTIGATIONS | 0 | 1 | 0 | 0 |
| Body temperature increased | 0 | 1 | 0 | 0 |
| MUSCULOSKELETAL AND CONNECTIVE TISSUE DISORDERS | 1 | 2 | 0 | 0 |
| Back pain | 0 | 2 | 0 | 0 |
| Sensation of heaviness | 1 | 0 | 0 | 0 |
| NERVOUS SYSTEM DISORDERS | 3 | 0 | 3 | 2 |
| Dizziness | 1 | 0 | 0 | 0 |
| Headache | 3 | 0 | 2 | 2 |
| Paraesthesia | 0 | 0 | 1 | 0 |
| RESPIRATORY, THORACIC AND MEDIASTINAL DISORDERS | 3 | 0 | 2 | 0 |
| Cough | 1 | 0 | 0 | 0 |
| Nasal congestion | 0 | 0 | 1 | 0 |
| Nasopharyngitis | 1 | 0 | 0 | 0 |
| Oropharyngeal pain | 1 | 0 | 0 | 0 |
| Respiratory tract infection | 0 | 0 | 1 | 0 |
| Rhinorrhoea | 1 | 0 | 0 | 0 |
| Upper respiratory tract irritation | 0 | 0 | 1 | 0 |
| SKIN AND SUBCUTANEOUS TISSUE DISORDERS | 1 | 1 | 0 | 0 |
| Skin reaction | 0 | 1 | 0 | 0 |
| Skin swelling | 1 | 0 | 0 | 0 |
| Skin warm | 1 | 0 | 0 | 0 |

Only treatment emergent AEs are summarised
*Multiple occurrences within a SOC by a subject were counted once per SOC.
**Multiple occurrences of a PT by a subject were counted once per PT.

TABLE 23

Summary of Subjects with Related AEs categorized by System Organ Class, Preferred Term and Treatment

| SYSTEM ORGAN CLASS*/PREFERRED TERM** | QM1114-DP | | | Pooled |
|---|---|---|---|---|
| | 30 units N = 6 | 60 units N = 6 | 90 units N = 6 | Placebo N = 6 |
| EYE DISORDERS | 1 | 0 | 1 | 1 |
| Asthenopia | 0 | 0 | 1 | 0 |
| Eye pruritus | 1 | 0 | 0 | 0 |
| Lacrimation increassd | 0 | 0 | 0 | 1 |
| GENERAL DISORDERS AND ADMINISTRATION SITE CONDITIONS | 1 | 3 | 2 | 2 |
| Application site bruises | 0 | 0 | 0 | 1 |
| Influenza like illness | 1 | 0 | 0 | 0 |
| Injection site bruising | 0 | 0 | 1 | 0 |
| Injection site erythema | 0 | 2 | 0 | 0 |
| Injection site pain | 0 | 1 | 0 | 0 |
| Sensation of pressure | 0 | 0 | 2 | 1 |
| INVESTIGATIONS | 0 | 1 | 1 | 0 |
| Body temperature increased | 0 | 1 | 0 | 0 |
| MUSCULOSKELETAL AND CONNECTIVE TISSUE DISORDERS | 1 | 0 | 0 | 0 |
| Sensation of heaviness | 1 | 0 | 0 | 0 |
| NERVOUS SYSTEM DISORDERS | 3 | 0 | 3 | 1 |
| Dizziness | 1 | 0 | 0 | 0 |
| Headache | 3 | 0 | 2 | 1 |
| Paraesthesia | 0 | 0 | 1 | 0 |
| RESPIRATORY, THORACIC AND MEDIASTINAL DISORDERS | 0 | 0 | 1 | 0 |
| Upper respiratory tract irritation | 0 | 0 | 1 | 0 |
| SKIN AND SUBCUTANEOUS TISSUE DISORDERS | 1 | 0 | 0 | 0 |
| Skin swelling | 1 | 0 | 0 | 0 |
| Skin warm | 1 | 0 | 0 | 0 |

Only treatment emergent AEs are summarized
*Multiple occurrences within a SOC by a subject were counted once per SOC
**Multiple occurrences of a PT by a subject were counted once per PT Safety Conclusions Overall, the most commonly reported AEs amongst the treatment groups were nervous system disorders and general disorders and administrative site conditions. The same holds true for treatment related AEs. The most frequent nervous system disorder was a headache reported in five subjects and the most frequent general disorders and administrative site conditions amongst subjects were injection site erythema and sensation of pressure.

The primary objective of this Phase I study was to determine the safety and tolerability of QM1114-DP at each dose level in healthy male and female subjects for the treatment of rhytids of the glabellar and lateral canthal regions. In this part of the study involving LCL, there were no SAEs and no withdrawals due to AEs or any other reasons. Forty four (44) AEs were reported in 18 of 24 (75.0%) subjects of which 31 AEs in 15 (62.5%) subjects overall were judged by the Investigator to be possibly or probably treatment related. All other AEs were judged by the Investigator to be unrelated to treatment. With the exception of one AE of moderate intensity (headache, 90 unit QM1114-DP treatment group), all other AEs were of mild intensity. AEs were reported at each dose level with the highest number reported at the maximum (90 units) and lowest (30 units) dose level. The fewest number of AEs (7 AEs) were reported in the placebo treatment group.

The most commonly reported SOC of AEs amongst the treatment groups were nervous system disorders and general disorders and administrative site conditions. This was also applicable for treatment related AEs. The most frequent nervous system disorder was headache reported in seven subjects and the most frequent general disorders and administrative site conditions amongst subjects were injection site erythema and sensation of pressure. No nervous system disorders were reported for the 60 unit QM1114-DP treatment group.

There were no clinically significant changes in haematology, biochemistry and urinalysis parameters during the study and no clinically significant physical examination findings. The isolated departures from the normal ranges in vital signs and ECG recordings were considered by the Investigator as not clinically significant and not related to the study drug.

Discussion and Overall Conclusions

The primary objective of this Phase I study was to evaluate the safety and tolerability of QM1114-DP at each dose level and the secondary objective was to assess the efficacy of QM1114-DP at each dose level for the temporary improvement of facial lines of the glabellar and lateral canthal regions in healthy male and female subjects.

Amongst individual subjects, the most commonly reported AEs were nervous system disorders. This was also relevant for treatment related AEs. The individually most common occurring AE that was considered by the Investigator to be treatment related was headache (eight treatment related AEs) reported in seven subjects overall. This was comparable to those observed in Part 1 (GL alone) where six treatment related headaches were reported in six subjects overall. With the exception of one AE of moderate intensity (headache), all AEs were of mild intensity and there were no SAEs or any withdrawals due to AEs. There were no clinically significant changes in haematology, biochemistry and urinalysis parameters during the study. Furthermore, there were no clinically significant physical findings. Subjects had vital signs within the reference ranges and there were no clinically significant findings observed in the ECG recordings made during the study.

In summary, the majority of the treatment related AEs were associated with nervous system disorders and general disorders and administrative site conditions. These treatment related AEs were within expectations according to the reference safety information and consistent with AEs observed from previous clinical studies using other BoNT-A products.

The efficacy data in the present study revealed that QM1114-DP is efficacious in reducing LCL severity at maximum smile at all dose levels in comparison to those subjects evaluated in the placebo treatment group. The mixed model analysis for the Investigator's evaluation of rhytids of the left and right lateral canthal regions at maximum smile showed that from Day 3 to Day 28 the change from baseline in mean MAS scores in the 30, 60, and 90 unit QM1114-DP treatment groups showed a statistically significant difference (P<0.05) when compared to scores in the placebo treatment group. For the subject's evaluation of rhytids of the left and right side of the face at maximum smile, statistically significant differences (P<0.05) from placebo were reported from Day 3 or week 1 to Day 28 for the 30 and 60 unit QM1114-DP treatment groups. In contrast, no statistically significant scores were reported when the 90 unit QM1114-DP treatment group was compared to scores in the placebo treatment group for left LCL. The subject's assessment of LCL satisfaction showed that, with the exception of two subjects, all subjects in active treatment groups were either very satisfied or satisfied with treatment through to Day 28.

In the placebo treatment group, at most 50% of subjects were dissatisfied or very dissatisfied with treatment.

In conclusion, the data indicated that QM1114-DP is efficacious in reducing LCL severity at maximum smile in comparison to those subjects in the placebo treatment group.

Overall conclusions:

All doses were safe and well tolerated.

There were no SAEs in this study.

There were no subject withdrawals due to AEs or any other reason.

With the exception of one AE of moderate intensity all AEs were of mild intensity.

There were no clinically significant changes in clinical laboratory tests, physical examinations, vital signs and 12-lead ECG parameters.

At rest the LCL severity decreased from Day 7 in the active treatment groups as assessed by the Investigator and subject in comparison to the placebo treatment group. This effect was maintained up to 28 days.

With the exception of the subject's assessment of LCL (90 unit QM1114-DP treatment group) at maximum smile the LCL severity was decreased in the active treatment groups as assessed by the Investigator and subject in comparison to the placebo treatment group. This effect was maintained up to 28 days.

The subject's assessment of LCL satisfaction showed that the majority of subjects in active treatment groups were either very satisfied or satisfied with treatment through to Day 28.

Example 3—A Randomized, Double-Blind, Placebo-Controlled, Single Treatment, Dose-Escalation Study to Evaluate the Safety and Efficacy of QM1114-DP in Healthy Male and Female Subjects with Moderate to Severe Upper Facial Wrinkles Pre-Clinical Studies In addition to the pre-clinical studies discussed in Example 2 above, general toxicology studies were conducted for QM1114-DP, including pilot single IM dose administration toxicity studies in Wistar rats and Beagle dogs. These were non-GLP (Good Laboratory Practice) studies performed for the purpose of determining the maximum tolerated dose for QM1114-DP to allow for setting the appropriate dose levels for the pivotal GLP toxicology study. Results of these pilot toxicology studies have clearly demonstrated that the Wistar rat was more sensitive to the toxic effects of QM1114-DP than the dog, and therefore the pivotal GLP toxicology study was conducted only in Wistar rats.

No separate local tolerance studies were performed with QM1114-DP. Instead, local tolerance was carefully evaluated through clinical observation and histopathology evaluation of the local injection sites as part of the pivotal GLP toxicology study in Wistar rats. No unexpected data were determined from these additional observations which indicated tolerance issues with the product.

Clinical Studies

In Examples 1 and 2, subjects received QM1114-DP for the treatment of moderate to severe lines of the glabellar or lateral canthal area.

Example 1—Glabellar Lines

Example 1 (GL only) was undertaken to evaluate the safety and tolerability of 10, 25, 50 and 75 units of QM1114-DP administered to healthy male and female subjects aged 18 to 65 years with moderate to severe GL. Four subjects received 10 units, six subjects received 25 units, six subjects received 50 units and six subjects received the maximum dose of 75 units QM1114-DP. Eight (8) subjects received placebo treatment. A total of 48 adverse events (AE) were reported in 23 subjects.

Thirty eight (38) AEs were reported in 17 subjects receiving QM1114-DP and 10 AEs were reported in six subjects receiving placebo treatment, none of which were serious and the majority were of mild intensity. One AE was rated as severe in intensity (vomiting [subject 144, 50 unit QM1114-DP treatment group]) and two were rated as moderate in intensity (vasovagal reaction [pre-syncope] occurring immediately after injection for subject 126 [25 unit QM1114-DP treatment group] and subject 146 [50 unit QM1114-DP treatment group]).

Of the 32 treatment related AEs the majority (17) were reported in the 75 unit QM1114-DP dose level of which injection-site reactions, i.e., erythema, oedema, irritation, rash, pruritus, pain, discomfort, stinging and bruising were the most common. The individually most common occurring AE that was considered by the Investigator to be treatment related was headache (six treatment related AEs), one of which occurred at the maximum dose.

There were no also clinically significant changes in clinical laboratory safety tests, physical examinations, vital signs and 12-lead electrocardiogram (ECG) parameters during the study.

Example 2—Lateral Canthal Lines

In the second part of study 43QM1302 (LCL only), 30, 60 or 90 units of QM1114-DP was administered to healthy male and female subjects aged 18 to 65 years with moderate to severe LCL. Six subjects received 30 units, six subjects received 60 units and 6 subjects received the maximum dose of 90 units QM1114-DP. Six (6) subjects received placebo treatment. In this study, a total of 44 AEs were reported in 18 subjects.

Thirty seven (37) AEs were reported for 13 subjects receiving QM1114-DP and seven AEs reported in five subjects receiving placebo treatment, none of which were serious and with the exception of one AE of moderate intensity (headache for subject 246, 90 unit QM1114-DP treatment group); all AEs were of mild intensity.

Of the 31 treatment related AEs the most commonly reported AEs amongst the treatment groups were nervous system disorders and general disorders and administrative site conditions. The most frequent nervous system disorder was a headache reported in seven subjects and the most frequent general disorders and administrative site conditions amongst subjects were injection site erythema and sensation of pressure.

Apart from these trends, there were no clinically meaningful safety findings including clinical laboratory safety values, vital signs, physical examinations and ECG parameters for any of the treatments.

Efficacy

The efficacy of QM1114-DP for the treatment of GL (n=22) and LCL (n=18) in healthy male and female subjects was assessed in study 43QM1302 (Examples 1 and 2). Efficacy was evaluated using validated Merz 5-point photo scales (Merz Aesthetic Scale: MAS) for Investigator and subject assessments of severity of rhytids, at rest and at maximum frown/smile. These results indicated that intramuscular administration of QM1114-DP up to 75 units (GL indication) or up to 90 units (LCL indication) was efficacious in reducing GL or LCL severity at maximum frown (GL indication) or maximum smile (LCL indication) in comparison to those subjects in the placebo treatment group. Furthermore, the subject's assessment of GL or LCL satisfaction showed that all subjects in QM1114-DP treatment groups were either very satisfied or satisfied with treatment through to Day 28.

In conclusion, the efficacy data from Examples 1 and 2 demonstrated that QM1114-DP is efficacious in reducing GL severity at maximum frown and LCL severity at maximum smile at all dose levels in comparison to those subjects evaluated in the placebo treatment group.

Study Objectives

Primary Objective: to evaluate the safety and tolerability of QM1114-DP at each dose level for the temporary improvement of the glabellar lines (GL) and lateral canthal lines (LCL), when treated in combination.

Secondary Objectives: to assess the efficacy of QM1114-DP at each dose level for the temporary improvement of the GL and LCL, and to assess the efficacy of QM1114-DP at each dose level for the temporary improvement of the GL and LCL, when treated in combination.

Study Endpoints

Safety: incidence and severity of AEs.

Efficacy:

Investigator's rating of GL severity at maximum frown and LCL severity at maximum smile through Day 28 (week 4) by live assessment using MAS GL-dynamic and LCL—dynamic;

Investigator's rating of GL and LCL severity at rest through Day 28 (week 4) by live assessment using MAS GL—at rest and LCL—at rest (static);

Subject's rating of GL severity at maximum frown and LCL severity at maximum smile through Day 28 (week 4) by live assessment using MAS GL—dynamic and LCL—dynamic; and Subject's rating of GL and LCL severity at rest through Day 28 (week 4) by live assessment using MAS GL—at rest and LCL—at rest (static)•Subject's assessment of satisfaction through Day 28 (week 4) using a 4-point rating scale.

Exploratory:

Investigator's rating of GL severity at maximum frown and LCL severity at maximum smile until the rhytid scoring returns to baseline by live assessment using MAS GL—dynamic and LCL—dynamic;

Investigator's rating of GL and LCL severity at rest until the rhytid scoring returns to baseline by live assessment using MAS GL—at rest and/or LCL—at rest Subject's rating of GL severity at maximum frown and LCL severity at maximum smile until the rhytid scoring returns to baseline by live assessment using MAS GL—dynamic and LCL—dynamic;

Subject's rating of GL and LCL severity at rest until the rhytid scoring returns to baseline by live assessment using MAS GL—at rest and LCL—at rest; and Subject's assessment of satisfaction using a 4-point rating scale.

Subjects who participated in the exploratory phase of this study visited the clinical pharmacology unit (CPU) every month. The exploratory endpoints were not included in this CSR.

Investigational Plan

This Example details the assessment of safety and efficacy of QM1114-DP for the temporary improvement of LCL and GL, when treated in combination. The study also included in separate parts cohorts 1-4 (Example 1 [GL]) and cohorts 5-7 (Example 2 [LCL]), treatment in escalating doses for GL and LCL as previously reported above.

The study was a randomized, double-blind, placebo-controlled design to evaluate the safety and efficacy of ascending botulinum toxin type A (QM1114-DP; active) doses administered to healthy male and female subjects aged 18 to 65 years with moderate to severe GL and LCL. A total of 16 subjects were enrolled in two cohorts (cohorts 8 and 9) with 8 subjects in each cohort (6 active: 2 placebo).

Each healthy subject received verbal (from a Research Physician) and written information prior to signing of the ICF. Subjects were screened for eligibility within 28 days prior to the study treatment on Day 1, and attended study visits for safety and efficacy assessments through the follow-up visit on Day 28 (week 4). All subjects were admitted to the CPU on Day −1 and stayed overnight on the day before dosing on Day 1. Sentinel groups at each dose level were used to minimize risks to subjects. Accordingly, a longer hospitalization in the CPU was required for the first 2 subjects (1 active and 1 placebo) in cohorts 8 and 9. These subjects were admitted to the CPU on Day −1, treated on Day 1, discharged from the CPU on Day 2 and then attended study visits through the follow-up visit on Day 28 (week 4). The study consisted of the following visits: Screening, Day −1, Days 1, 2, 3, 7, 14, 21 and 28.

Investigators and subjects assessed the appearance of GL and LCL at screening, pretreatment, and at all post-treatment visits using MAS GL and LCL dynamic and at rest. Subjects also assessed their satisfaction with the appearance of their GL and LCL using a 4-point rating scale at all post-treatment visits (Ascher et al., 2009).

Subjects were randomized to receive one treatment with study drug (QM1114-DP or placebo). Each treatment included 11 injections of equal volume (100 μl) administered to the GL area (five injections) and LCL area (three injections to each side of the face). For GL, the five injection sites included two injections in each corrugator supercilii muscle, and one injection in the procerus muscle. For LCL, the position of the injections were adjusted in accordance with the LCL pattern of rhytids for the individual subject. In all cases, the injection points were at the external part of the orbicularis oculi and, when applicable, at about 1-2 cm from the orbital rim.

The dose levels of QM1114-DP were:

Cohort 8, Dose 1: QM1114-DP total of 110 units per treatment (10 units per injection site [50 units in total for GL area and 60 units in total for LCL area]).

Cohort 9, Dose 2: QM1114-DP total of 140 units per treatment (10 units per injection site for GL [50 units in total for GL area] and 15 units per injection site for LCL [90 units in total for LCL area]).

The procedures and assessments that were conducted during this study are presented by study visit in Table 1. The clinical study included the screening and up to week 4 (follow-up) visit. If scoring (maximum frown [for GL] and maximum smile [for LCL]) had returned to baseline as assessed by the Investigator, subjects had their last visit to the CPU at Day 28 (week 4). At this point the study was formally completed. Subjects whose rhytid severity scores (maximum frown [GL] and maximum smile [LCL]) did not return to baseline at Day 28 (week 4) as assessed by the Investigator, participated in the exploratory phase of this study and visited the CPU every month until the rhytid scoring returned to baseline. Data from this exploratory follow-up of efficacy will be reported separately and not in this CSR.

Selection of Study Population

This study was conducted in a randomized, placebo controlled-design to assess the safety and tolerability of QM1114-DP at each dose level and to assess the efficacy of QM1114-DP at each dose level for the temporary improvement of facial lines of the left and right lateral canthal, and glabellar regions. The selection criteria were defined such that subjects selected for participation in the study were free from any significant illness.

Within 28 days before the start of the study, subjects underwent a full screening procedure as described in Table 24.

TABLE 24

| | | | | | | | | W4$^g$ |
| | | | | | | | | (D28) |
| | Screening | | | | | | | Follow- |
| | Day −28- | D | D | D | D | W 1$^f$ | W 2$^f$ | W 3$^f$ | |
| Study Period | Day −1 | −1 | 1 | 2 | 3 | (D7) | (D14) | (D21) | up |
|---|---|---|---|---|---|---|---|---|---|
| Informed Consent | X | | | | | | | | |
| Inclusion/Exclusion criteria | X | X | | | | | | | |
| Demographic data | X | | | | | | | | |
| Medical History | X | X | | | | | | | |
| Concomitant medication recording | X | X | X | X | X | X | X | X | X |
| Serotogy | X | | | | | | | | |
| Body weight/height/BMI | X | | | | | | | | X |
| Vital signs | X | X | X$^a$ | X | X | X | X | X | X |
| Full physical examination | X | X$^b$ | | | | | | | X |

TABLE 24-continued

Study Flowchart

| Study Period | Screening Day −28- Day −1 | D −1 | D 1 | D 2 | D 3 | W 1[f] (D7) | W 2[f] (D14) | W 3[f] (D21) | W4[g] (D28) Follow-up |
|---|---|---|---|---|---|---|---|---|---|
| Focused physical examination[c] | X | X | X[a] | X | X | X | X | X | X |
| 12-lead ECG | X | X | X[a] | X | X | X | X | X | X |
| Alcohol breath test | X | X | | | | | | | |
| Serum pregnancy test | X | X | | | | | | | X |
| Haematology/Biochemistry | X | X | | X | | X | X | X | X |
| Urinalysis | X | X | | X | | X | X | X | X |
| Urine Drugs of Abuse | X | X | | | | | | | |
| Clinical Immunogenicity Assay | | X | | | | | | | X |
| AES (AEs) | X | X | X | X | X | X | X | X | X |
| Efficacy assessments[f] | | | | | | | | | |
| Investigator 'live' assessments | X | X | | X | X | X | X | X | X |
| Subject 'live' assessments | X | X | | X | X | X | X | X | X |
| Subject satisfaction | | | | X | X | X | X | X | X |
| Photography | X | X | | X | X | X | X | X | X |
| Meals[d] | | X | X | X | | | | | |
| Study drug administration | | X | | | | | | | |
| Hospitalisation[e] | | → | | | | | | | |
| Outpatient visits | | | | | X | X | X | X | X |

[a]At pre-dose, 1 hour, 4 hours, 8 hours and 12 hours.
[b]An abbreviated physical examination was done Day −1 and focused on any health changes since screening.
[c]Focused examination of eyes and face.
[d]A light meal was given prior to dosing. At all other times standardised meals were consumed at standard unit times during the in-house period.
[e]All subjects were hospitalised in the morning of Day −1. Subjects in the sentinel groups for cohort 5, 6 and 7 were hospitalised until Day 2. All other subjects were discharged from the CPU on Day 1.
[f]Flexibility of ±1 day from the scheduled visit was permitted at week 1 and ±2 days from the scheduled visit was permitted from week 2 onwards.
[g]If the efficacy score (Investigator 'live' assessment, maximum frown/smile) had not returned to baseline at week 4, the subject attended monthly exploratory-follow up visits at the CPU until the score had returned to baseline (as assessed by the investigator at maximum frown-smile). For subjects whose scoring had returned to baseline, week 4 was tied last visit to the CPU.

Inclusion Criteria

To be eligible for inclusion in this study, each subject fulfilled each of the following criteria:

Healthy male or female aged between 18 and 65 years (inclusive) at screening.

Had no prior treatment with BoNT-A or B.

Had a rhytid severity score, at maximum frown, of at least moderate severity (grade 2) as assessed by the Investigator at the screening and baseline visits using a validated photo scale (MAS GL-dynamic).

Had moderate to severe (Grade 2 or 3) LCL during maximum smile on both sides of the face, as assessed by the Investigator at screening and baseline visits using a validated photo scale (MAS LCL—dynamic).

Had a rhytid severity score, at rest, of at least mild severity (grade 1) as assessed by the Investigator at the screening and baseline visits using a validated photo scale (MAS GL—at rest).

Had a mild to severe (Grade 1, 2 or 3) LCL at rest on both sides of the face as assessed by the Investigator at screening and baseline visits using a validated photo scale (MAS LCL—at rest).

Subjects agreed to use an acceptable method of contraception.

Were able to understand and comply with the requirements of the protocol and had signed the ICF prior to undergoing any study-related procedures.

Had no clinically significant disease or abnormal laboratory, ECG or vital signs values as determined by medical history, physical examination or other evaluations, conducted at the screening visit or on admission to the CPU.

Exclusion Criteria

A subject was not eligible for inclusion in Part 3 of this study if any of the following criteria applied:

Had received prior BoNT-A or B treatment.

Had rhytids of the GL and/or LCL area that could not be substantially smoothed-out manually by spreading the skin apart.

Had previous insertion of any permanent or semi-permanent material or had dermal filler treatment to the GL and/or LCL lines area.

Had an infection in the GL and/or LCL area within 14 days prior to the baseline visit.

Currently had a history of eyelid or eye brow ptosis.

Had dry eyes, prominent eye bags or morning eyelid oedema.

Had cancerous or pre-cancerous lesions, active or chronic skin disease, inflammation or related conditions including scar near or on the glabellar area.

Had prior facial cosmetic surgery (e.g., blepharoplasty, periorbital surgery, facial lift, brow lift, eyelid lift or eyebrow surgery).

Had facial laser or light treatment, microdermabrasion, or superficial peels within 6 months prior to screening for this study.

Had a history of facial nerve paralysis.

Used topical preparations that claim to have anti-wrinkle activity within 7 days prior to study drug administration or planned to use such preparations while on study.

Subject had facial cosmetic surgery or procedures planned during the study period.

Had flu-like syndrome within 14 days prior to day of injection.

Currently received or had received aminoglycoside antibiotic therapy, curare-like drugs, quinidine, succinylcholine, polymyxins, anticholinesterases, magnesium sulfate, or lincosamides. Any other prescription or non-prescription medications were allowed at the discretion of the Investigator as long as it did not negatively impact on the safety of the subject or integrity of the study data.

Was pregnant or lactating (female subjects of childbearing potential must have had a negative pregnancy test [serum] prior to randomization).

Had a confirmed positive urine drug screen indicating drug abuse including: opiates, barbiturates, cocaine metabolite, methadone, benzodiazepine, cannabinoid, or amphetamine.

Had a history or clinical evidence of alcoholism or drug abuse.

Had a positive screen for hepatitis B consisting of HBsAG (Hepatitis B surface antigen), anti-HCV (hepatitis C virus antibody) and human immunodeficiency virus (HIV).

Had a history of dysphagia, aspiration or inhalation pneumopathy.

Had a history of a bleeding disorder.

Had a history of autoimmune disease that may have potentially interfered with study outcomes.

Had an active multisystem disease that may have potentially influenced safety or assessment of study outcomes; including, but not limited to, clinically significant cardiovascular, respiratory, hepatic/biliary, renal, gastrointestinal, endocrine, psychiatric or neurologic disorder.

Had a history of myasthenia gravis or another neurotransmission disease.

Had a neuromuscular disorder that may have potentially interfered with subject outcomes.

Had received any investigational product during the 90 days prior to screening for this study.

Smoked more than 10 cigarettes or equivalent amount of tobacco per day and could not stop smoking while in the CPU.

Had any condition(s) that in the opinion of the Principal Investigator (PI) would compromise the safety of the subject or prevent the subject from completing the study.

Could not communicate reliably with the Investigator.

Subjects who were vegetarians, vegans or had medical dietary restrictions conflicting with the study standardized menus.

Removal of Subjects from Therapy or Assessment

Standard toxicity grading according to the National Cancer Institute Common Terminology Criteria (NCI CTC, version 4.0) was used to grade the AEs. This is owing to the fact that these are the only standardised set of comprehensive criteria available and have proven useful in healthy volunteer Phase I studies. Local laboratory normal values were applied. Abnormal laboratory and other tests were always repeated prior to grading in order to ensure consistency and to exclude technical errors. Diurnal variations in laboratory parameters and other measurements as well as baseline status and conditions (e.g. Gilbert's syndrome) were always taken into account when assessing whether abnormalities constitute a drug related toxicity and when grading, if applicable.

The CTC for AE (CTCAE) displays Grades I through V with detailed clinical descriptions of severity for each AE based on this general guideline. The grade definitions are described as follows:

Grade I: Mild; asymptomatic or mild symptoms; clinical or diagnostic observations only; intervention not indicated.

Grade II: Moderate; minimal, local or non-invasive intervention indicated; limiting age-appropriate instrumental ADL*.

*Instrumental Activities of Daily Living (ADL) refer to preparing meals, shopping for groceries or clothes, using the telephone, managing money, etc.

Grade III: Severe or medically significant but not immediately life-threatening; hospitalization or prolongation of hospitalization indicated; disabling; limiting self care ADL**.

**Self care ADL refer to bathing, dressing and undressing, feeding self, using the toilet, taking medications and not bedridden.

Grade IV: Life-threatening consequences; urgent intervention indicated.

Grade V: Death related to AE.

The CTCAE criteria and their interpretation are consistent with the standard intensity grading for AEs during clinical trials: Grade I: mild, Grade II: moderate, Grade III: severe or medically significant but not immediately life-threatening, may constitute serious adverse event (SAE)/suspected unexpected serious adverse reaction (SUSAR). Grades IV and V constitute SAE/SUSAR.

The study was to be stopped if certain adverse events occurred with a reasonable possibility of a causal relationship with the IMP.

Withdrawal of Subjects

In accordance with the Declaration of Helsinki, subjects could have withdrawn at any time, but once treatment or dosing occurred every attempt was made to continue assessments to ensure the safety of the subject. Specific reasons for withdrawing a subject were:

Voluntary discontinuation by the subject, who was at any time free to discontinue his or her participation in the study.

Severe non-compliance or major deviation from the protocol as judged by the Investigator and/or Sponsor.

Incorrect inclusion, i.e. the subject, with the benefit of hindsight, did not meet the required eligibility criteria for the study at the time of inclusion.

Other reasons as judged by the PI.

Subjects were at any time free to withdraw from the study, without prejudice (withdrawal of consent). Such subjects were always asked about the reason(s) and the presence of any AEs. If possible, subjects who were withdrawn from the study after dosing and before completion of the week 4 visit were to have been seen by the PI or delegate and undergo the assessments and procedures scheduled for the follow-up visit. AEs were to be followed until resolution, return to baseline or stabilization if a non-study related cause had been established, whenever possible.

Replacement of Subjects

The planned number of subjects must have completed each cohort in order to assess the safety and tolerability of a given dose of QM1114-DP or placebo (7 days post treatment). If the number of completed subjects was less than the minimum requirement of a given cohort, in order to make a decision on dose escalation, the sponsor and PI may have decided that these subjects were to be replaced and those subjects were treated and assessed accordingly prior to the next dose escalation.

Treatments

Treatments Administered

Subjects were randomized to receive one treatment with study drug (QM1114-DP or placebo). Each treatment included 11 injections (one injection per injection site) of equal volume (100 μl) administered to the GL area (five injections) and LCL area (three injections to each side of the face). For GL, the five injection sites included two injections in each corrugator supercilii muscle, and one injection in the procerus muscle. For LCL, the position of the injections were adjusted in accordance with the LCL pattern of rhytids for the individual subject. Depending on the pattern of rhytids for individual subjects, if the lines in the LCL region were above and below the lateral canthus, injections were administered as described in FIG. 12A. Alternatively, if the lines in the LCL for the individual subject were primarily below the lateral canthus, injections were administered as described in FIG. 12B. In all cases, the injection points were at the external part of the orbicularis oculi and, when applicable, at about 1-2 cm from the orbital rim.

Assigning Subjects to Treatment Groups

Subjects who signed the informed consent for the study and thereafter underwent screening procedures were identified during this period by their unique RPL ID number (identification number from the RPL volunteer database) and screening number.

Subjects fulfilling the eligibility criteria were assigned subject numbers before dosing in the morning of Day 1. Subject numbers were assigned from 301 to 308 (Cohort 8) and 321 to 328 (Cohort 9). Subject numbers were allocated in consecutive order and corresponded to a number on the computer generated randomization list, which determined the treatment sequence. If a subject discontinued from the study, the subject number was not re-used and the subject was not allowed to re-enter the study.

Selection of Doses in the Study

For GL, available clinical data were considered to be representative for dose selection of QM1114-DP. The choice of doses for FIH studies of QM1114-DP was based upon the clinical experience in the treatment of the same facial areas, but using the pharmacology and toxicology data generated to date as supportive of an equivalent mode of action, overall responses and reversible effect. The standard clinical dose in treatment of GL is five injections with 10 units per injection (in total 50 units also called Speywood units, sU). In Example 1 (GL only), as a safety precaution, the proposed starting dose of QM1114-DP was 2 units per injection (in total 10 units) to be followed by dose escalations (after SRC decisions) in three steps to 5 units per injection (in total 25 units), then 10 units per injection (in total 50 units) and then 15 units per injection (in total 75 units).

The starting dose for the LCL (Example 2) indication was 5 units per injection (in total 30 units) to be followed by dose escalations (after SRC decisions) to 10 units per injection (in total 60 units) then 15 units per injection (in total 90 units). The maximum dose used in the study for the treatment of LCL was based upon previous studies. Earlier studies of BoNT examined 15, 30 and 45 units administered to each side for the treatment of LCL (totals of 30, 60 and 90 units administered). The incidence of treatment-emergent AEs was similar for all doses studied.

Selection and Timing of Dose

In this study, subjects received one treatment of 110 or 140 units of QM1114-DP or placebo in the morning of Study Day 1.

Study Procedures

For screening, study days and follow-up please refer to Table 24.

All study measurements obtained are described below.

Should there have been any safety concerns based on a review of the safety data for an individual subject, additional vital signs, ECG recordings and/or laboratory safety samples may have been taken. The total volume of blood to be withdrawn during the study should not have exceeded 300 ml per subject.

Vital Signs

Blood Pressure, Heart Rate, Tympanic Temperature and Respiratory Rate

Supine blood pressure (BP) and heart rate (HR) were measured using a semi-automatic BP recording device (Critikon Dinamap® monitors) with an appropriate cuff size. For respiratory rate measurements subjects were required to rest in a supine position for at least 10 minutes prior to respiratory rate measurement. For timings of individual measurements, refer to the Study Flowchart (Table 24). The timings of all measurements performed during the study might have been subject to change based on the ongoing review of safety and tolerability data. Body temperature (tympanic) was measured (a single measurement) in degrees Celsius using an automated thermometer at the times indicated in the Study Flowchart (Table 24). Additional temperature assessments may have been taken for safety at the discretion of the PI or delegate.

ECG Measurements

Triplicate 12-lead ECGs were recorded using a GE Marquette MAC1200@/MAC1200ST® recorder connected via a fixed network connection to the MUSE® Cardiology Information System (MUSE). All ECGs recorded during the study were stored electronically on the MUSE information system. Only ECGs recorded electronically were valid ECGs for any purpose other than safety assessment. ECG printouts were filed in the subject's CRF for medical safety reviews.

If at all possible, the same recorder was used for any one subject. Each ECG recorder was set up to the required technical specifications and containing the information required to identify the records. Each ECG recording was clearly identified (subject ID, scheduled time relative to dose and the actual times of ECG recordings).

12-lead ECG recordings were made at the time-points indicated in the Study Flowchart (Table 24) after the subjects had rested in a supine position for at least 10 minutes. The subjects avoided postural changes during the ECG recordings and clinical staff ensured that subjects were awake during the ECG recording.

All recorded ECG were reviewed by a Research Physician on an ongoing basis and the review was documented in the CRF. If a subject showed an abnormal ECG at any stage, additional safety recordings (including the use of 5 or 12-lead Holter equipment) were to be made and the abnormality followed to resolution if required.

The timings of all measurements performed during the study could have been subject to change based on the ongoing review of safety and tolerability data.

Clinical Laboratory Safety Measurements

Clinical laboratory safety parameters are listed in Table 25, below.

TABLE 25

| Clinical Laboratory Safety Parameters | | | | |
|---|---|---|---|---|
| Biochemistry | Haematology | Urinalysis* | Serology | Urine Screen for Drugs of Abuse |
| Aspartate aminotransterase (AST) | Red blood cells | Leukocytes | HBsAG | Benzodiazepines |
| Alanine aminotransferase (ALT) | Haemoglobin | Nitrite | Hepatitis C antibodies | Opiates |
| Alkaline phosphatase (ALP) | Haematocrit | Urobilinogen | HIV 1 and 2 antibodies | Amphetamines |
| Lactate dehydrogenase (LDH) | Mean corpuscular volume | Protein | | Methadone |
| Creatine kinase (CK) | Mean corpuscular haemoglobin concentration | pH | | Cocaine |
| Gamma glutamyltransferase (Gamina GT) | White blood cells | Blood | | Cannabinoids |
| Total bilirubin | Neutrophils | Specific gravity | | Barbiturates |
| Creatnine | Lymphocytes | Ketones | | |
| Urea | Monacytes | Bilirubin | | |
| Total Protein | Eosinophils | Glucose | | |
| Albumin | Basophils | | | |
| Glucose—fasting | Platelet count | | | |
| Sodium | | | | |
| Potassium | | | | |
| Calcium | | | | |
| Phosphate | | | | |
| Cholesterol—fasting | | | | |
| Triglycerides—fasting | | | | |
| β-HCG$^a$ | | | | |

*If deemed necessary, based on a clinically significant positive uralysis test, microscopic examination of sediment and/or culture was performed by The Doctors Laboratory (TDL).
$^a$Serum β-HCG (beta-human chorionic gonadotrophin) was done at screening and admission).

Haematology and Biochemistry

Blood samples for determination of haematology and biochemistry parameters were taken at the times given in the Study Flowchart (Table 24). The date and time of collection was recorded on the appropriate CRF. The analyses were done at TDL, using routine methods. Blood samples for determination of standard haematology parameters were collected in 4 ml K3EDTA tubes and blood samples for determination of standard biochemistry parameters were collected in 5 ml Serum Separator Tubes (SST).

Laboratory values outside the reference limits, which were suspected to be of any clinical significance, were to be repeated. Subjects in whom the suspected clinical significance was confirmed on repeated sampling were either not to be included or, if already included, may have been withdrawn from further participation in the study and/or followed until normalization or for as long as the Investigator or delegate considered it necessary.

Serology

Serology was performed as detailed in the Study Flowchart (Table 24). At the screening visit, all subjects were tested for the parameters listed in Table 25. This was done for the safety of the study personnel and the results from the tests were not entered into the study database. If the subject (s) was (were) found to be positive to any of these tests, he or she would have been referred for further examination and treatment and was not included in the study. The serology tests were analyzed in the same blood sample used for clinical chemistry (collected in a 5 ml SST tube). The samples were analyzed by TDL.

β-HCG

To exclude pregnancy, a serum β-HCG blood sample was performed as described in Table 24 and whenever pregnancy was suspected. Any subject with a positive pregnancy test was to be excluded or withdrawn from the study.

Urinalysis

Urine samples for determination of urinalysis parameters were taken at the times given in the Study Flowchart (Table 24). Urinalysis was performed on the parameters described in Table 25 by RPL using a dipstick method. If deemed necessary, based on a clinically significant positive test, microscopic examination of sediment and/or culture was performed by TDL.

Drugs of Abuse

Urine was tested for the drugs of abuse at RPL at the times described in Table 24. If a subject failed the drug abuse screen, he/she was excluded from the study. A repeat drug screen was only done where methodological reasons were believed to have led to a false positive. Borderline positive results, unless covered by the preceding condition, were to be considered as positive and the subject excluded from the study. If the subject was found to be positive due to medication e.g. flu/cold remedies, a repeat drug screen was performed if the subject was still within the screening window. The results from the tests were not entered into the database.

Alcohol Breath Test

An alcohol breath test was performed using an alcometer (for time-points see Study Flowchart Table 24). The results from this test were not entered into the clinical study database. If a subject had a positive alcohol breath test they would have been excluded from the study.

Physical Examination, Height and Weight

The timing of individual examinations is indicated in the Study Flowchart (Table 24). The physical examination performed at screening and at follow-up (day 28) included a full physical examination of the following: general appearance, skin, head, neck, lymph nodes, thyroid, abdomen, musculoskeletal, cardiovascular, respiratory and neurological systems.

The physical examination performed on Day −1 was a brief examination that focused on any changes since screening.

Height was measured in centimeters and weight in kilograms. Measurements were taken with subjects wearing light clothing and without shoes using calibrated scales for all measurements. Body mass index (BMI) was calculated from the height and weight.

Focused Physical Examination

A focused physical examination of the eyes and face (see Table 24 for time-points) was performed using a standardized scoring system to monitor local warmth, itching, pain, oedema/induration, erythema and bruising. The scoring system was as follows:

Minor change; or

Moderate change.

Efficacy Assessment

Efficacy assessment was performed at the time-points specified in the Study Flowchart (Table 24).

Investigator and Subject Assessment of Severity of Rhytids

At each visit the investigator and the subject independently rated the severity of the subject's rhytids "at rest", "at maximum frown" (for GL indication) and "at maximum smile" (for LCL indication). The investigator assessed the rhytids using the MAS GL dynamic and at rest and/or MAS LCL dynamic and at rest according to the following grades (using high resolution photographs as a guide to the scale grading):

TABLE 26

| Grade | Severity of GL |
| --- | --- |
| 0 | None |
| 1 | Mild |
| 2 | Moderate |
| 3 | Severe |
| 4 | Very severe |

TABLE 27

| Grade | Severity of LCL |
| --- | --- |
| 0 | None |
| 1 | Mild |
| 2 | Moderate |
| 3 | Severe |
| 4 | Very severe |

Subject's Assessment of Satisfaction

At each post-treatment visit the subject assessed his/her degree of satisfaction with treatment using a 4-point rating scale as follows:

TABLE 28

| Grade | Subject satisfaction |
| --- | --- |
| 0 | Very satisfied |
| 1 | Satisfied |

TABLE 28-continued

| Grade | Subject satisfaction |
| --- | --- |
| 2 | Dissatisfied |
| 3 | Very dissatisfied |

Photography

Standardized digital photographs were taken at the time-points specified in the study Flowchart (Table 24). The photographs were used only to illustrate the effect of the IMP and were not used to assess efficacy. Subjects were instructed to remove any make-up prior to arrival at the clinic or at the clinic prior to any photography.

The following photographs were taken:

The full face at rest (no smile); and

Photographs of the GL area and/or LCL area (one at maximum frown [for GL indication] or maximum smile [for LCL indication] and one at rest).

Sample Collection

Clinical Immunogenicity Assay: An assay to measure neutralizing antibodies to QM1114-DP will be developed later. Blood samples were collected at the time-points specified in the Study Flowchart (Table 24) for measurement of antibodies when the assay becomes available.

Adverse Events

The definitions of AEs, adverse drug reactions (ADRs), SAEs and suspected unexpected serious adverse reactions (SUSARs) are given below. It was of the utmost importance that all staff involved in the conduct of the clinical research was familiar with the content of this section.

Definitions

Adverse Event (AE)—An AE is the development of an undesirable medical condition or the deterioration of a preexisting medical condition following or during exposure to a pharmaceutical product, whether or not considered causally related to the product. An undesirable medical condition can be symptoms (e.g. nausea, chest pain), signs (e.g. tachycardia, enlarged liver), or the abnormal results of an investigation (e.g. laboratory findings, ECG). In clinical studies, an AE can include an undesirable medical condition occurring at any time, from the date informed consent was signed until the end of their participation in a study, i.e. the subject has discontinued or alternatively completed the study (Day 28).

The causality of AEs (i.e. their relationship to study treatment) was assessed by the Investigator(s) who, in completing the relevant case report form, must answer "yes" or "no" to the question "Do you consider that there is a reasonable possibility that the event may have been caused by any of the following—study medication—other medication?".

Note that SAEs which could be associated with any study procedure were also to be reported.

Adverse Drug Reaction (ADR)—An ADR is any AE where a causal relationship with the IMP is at least a reasonable possibility.

Serious Adverse Event (SAE)—An SAE is an AE occurring during any study phase (i.e., run-in, treatment, washout and/or follow-up) and at any dose of the IMP or placebo, that fulfils one or more of the following criteria:

Results in death.

Is life-threatening.

Requires in-patient hospitalization or prolongation of existing hospitalization.

Results in persistent or significant disability or incapacity.

Is a congenital abnormality or birth defect.

Is an important medical event that may jeopardize the subject or may require medical intervention to prevent one of the outcomes listed above.

The causality of SAEs (i.e. their relationship to study treatment) was assessed in the same way as for non-serious AEs. Note that SAEs which could be associated with any study procedure were also to be reported.

Suspected Unexpected Serious Adverse Reaction (SUSAR)—A SUSAR is any SAE where a causal relationship with the IMP is at least a reasonable possibility, but is not listed in the Investigator's Brochure and/or Summary of Product Characteristics.

Appropriateness of Measurements

All efficacy and safety measures used in this study were standard, widely used and recognized as reliable and accurate.

Study Subjects

For this study, 16 healthy subjects, 6 males and 10 females were randomized and dosed according to the clinical study protocol (CSP). All have completed the study and were analyzed for safety and efficacy.

Descriptive statistics for demography parameters summarized in Table 29 below. Fourteen (14) subjects were Caucasian, one was Asian and one was deemed to be of other mixed race. The subjects were aged between 35 and 57 years (inclusive). The weight ranged between 55.1-103.7 kg and BMI was between 20.5-32.7 kg/m2 for all subjects. At the entry to the study, there were no existing clinically significant findings in the subjects' medical or surgical history. There were also no remarkable findings in the physical examination for individual subjects during the study.

Table 30, Table 31 (Investigator's evaluation), Table 32 and Table 33 (Subject's evaluation). Efficacy was evaluated using the validated MAS rating scales for Investigator's and subject's assessments of severity of rhytids. The scales used the following grades for the severity: 0 (none), 1 (mild), 2 (moderate), 3 (severe) and 4 (very severe).

Severity of Rhytids at Rest

Glabellar Lines (GL):

The efficacy data showed that following administration of QM1114-DP, the severity of rhytids at rest in the glabellar region decreased in the active treatment groups as assessed by the Investigator and subject in comparison to the placebo treatment group (FIG. 15 and FIG. 16). Investigator's assessment of rhytid severity indicated that the maximum effect at rest was reached at Day 28 for the 50/60 unit QM1114-DP treatment group (mean score of 0.5 on the MAS) whilst for the 50/90 unit QM1114-DP treatment group the maximum effect was reached sooner (between Day 3 and Day 14) with a mean score of between 0.5-0.7 on the MAS. On Day 28, the mean MAS score was 0.7 for the 50/90 unit QM1114-DP treatment group. For subject's assessment of rhytid severity at rest, the maximum effect was reached on Day 21 (mean score of 0.2 on the MAS) and was maintained up to Day 28 for the 50/60 unit QM1114-DP treatment group. For the 50/90 unit QM1114-DP treatment group, the maximum effect was reached at Day 28 (mean score of 0.3 on the MAS).

Lateral Canthal Lines (LCL):

Following administration of QM1114-DP at rest, the LCL severity decreased in the active treatment groups as assessed by the Investigator and subject in comparison to the placebo treatment group (FIG. 15 and FIG. 16). Investigator's assessment of rhytid severity indicated that the maximum

TABLE 29

| | | Summary of Demographic Data | | |
| | | Q4M1114-DP | | |
| | | Cohort 8 50/60 units | Cohort 9 50/90 units | Placebo |
| | Summary | | n | |
| Variable | Statistics | 6 | 5 | 4 |
| Age | Mean ± SD | 44.7 ± 55 | 43.7 ± 8.75 | 39.8 ± 4.85 |
| (years) | Median (min; max) | 44.0(41; 51) | 42.5(35; 57) | 39.0(36; 46) |
| Height | Mean ± SD | 165.0 ± 7.61 | 173.8 ± 7.95 | 169.0 ± 9.55 |
| (cm) | Median (min; max) | 170.0(155; 177) | 175.0(159; 183) | 165.5(162; 183) |
| Weight | Mean ± SD | 67.82 ± 10.68 | 87.47 ± 9.71 | 78.83 ± 10.85 |
| (kg) | Median (min; max) | 67.4(55.1; 81.4) | 88.1(74.9; 98.9) | 72.5(66.6; 103.7) |
| BMI | Mean ± SD | 23.97 ± 2.55 | 29.02 ± 3.30 | 27.33 ± 2.49 |
| (kg/m$^2$) | Median (min; max) | 23.6(20.5; 26.2) | 29.5(23.9; 32.7) | 20.4(25.4; 31.0) |

Efficacy Evaluation

The efficacy analysis set consisted of all subjects (16 subjects) who received a single dose of QM1114-DP or Placebo and for whom post-dose efficacy data existed.

One of the objectives of this study was to assess the efficacy of QM1114-DP at each dose level for the temporary improvement of facial lines of the glabellar and lateral canthal region, when treated in combination. FIG. 15 and FIG. 16 show the mean rhytid scores of the glabellar and lateral canthal region (left and right side) by treatment group over time by Investigator and subject at rest, at maximum frown (for GL) and at maximum smile (for LCL). The Mixed Model analyses of Investigator's and subject's evaluation of the severity of rhytids at rest, at maximum frown (for GL) and at maximum smile (for LCL) are presented in effect was reached between Day 14 and Day 28 for the treatment groups with mean scores ranging between 0.7 to 0.8 (left LCL) and 0.8 (right LCL) on the MAS. For subject's assessment of rhytid severity similar trends of decrease were noted. The maximum effect was reached between Day 14 and Day 21 for the treatment groups with mean scores ranging from 0.5 to 0.8 (left LCL) and 0.7 to 0.8 (right LCL) on the MAS.

Severity of Rhytids at Maximum Frown (GL Indication)

At maximum frown, the severity of the rhytids in the glabellar region as assessed by the Investigator and subject in the active treatment groups decreased from Day 2 (FIG. 15 and FIG. 16). The maximum effect (mean score of 0.7 on the MAS) for the 50/60 unit QM1114-DP treatment group was reached on Day 14 for Investigator assessed, and there was still an effect up to Day 28 (mean score of 0.7 on the MAS). For the 50/90 unit QM1114-DP treatment group, the maximum effect was reached on Day 7 with a mean score of 0.5 on the MAS GL-dynamic and was maintained up to Day 28. For subject assessment of rhytid severity, the maximum effect (mean score of 0.5 on the MAS) for the 50/60 unit QM1114-DP treatment group was reached on Day 14, and was maintained up to Day 28 (mean score of 0.5 on the MAS). For the 50/90 unit QM1114-DP treatment group, the time to reach the maximum effect was longer (Day 28, mean score of 0.3 on the MAS).

Severity of Rhytids at Maximum Smile (LCL Indication)

As with GL, similar trends of decrease were also observed for Investigator and subject assessment of LCL severity at maximum smile FIG. 15 and FIG. 16). For subjects in the 50/60 unit QM1114-DP treatment group, the maximum effect as assessed by the Investigator was reached on Day 14 for the left LCL (mean score of 0.8 on the MAS) and Day 21 for the right LCL (mean score of 1.0 on the MAS), and there was still some effect up to Day 28 (mean score of 0.8 [left LCL] and 1.0 [right LCL] on the MAS). In comparison, the maximum effect for the 50/90 unit QM1114-DP dose level was reached at Day 7 (mean score of 1.0 [left LCL] and 1.0 [right LCL] on the MAS and this was maintained up to Day 28 (mean score of 1.0 [left LCL] and 1.0 [right LCL] on the MAS). Similar patterns of decrease were also observed for subject's assessment of rhytid severity (FIG. 16). The maximum effect in rhytid severity for subjects in the 50/60 unit QM1114-DP treatment group was observed on Day 14 for the left LCL (mean score of 0.8 on the MAS) and there was still some effect up to Day 28 (mean score of 1.2 on the MAS). For rhytids in the right LCL, the maximum effect was reached at Day 14 (mean score of 1.0 on the MAS) and there was still some effect at Day 28 (mean score of 1.3 on the MAS). For subjects in the 50/90 unit QM1114-DP treatment group, the maximum effect was reached at Day 21 for LCL on the left side (mean score of 1.0 on the MAS) and Day 28 for LCL on the right side (mean score of 0.8 on the MAS).

Subject's Assessment of Satisfaction

At each post-treatment visit, the subject assessed his/her degree of satisfaction with treatment using a four point rating scale. The scale used the following grades for satisfaction: 0 (very satisfied), 1 (satisfied), 2 (dissatisfied) and 3 (very dissatisfied).

The subject's assessment of satisfaction showed that the majority of subjects in the 50/60 and 50/90 unit QM1114-DP treatment groups were either very satisfied (0) or satisfied (1) with treatment from Day 2 to Day 28. Some subjects, such as subject 301 (on Day 7 to 28) and subject 305 (on Day 28) in the 50/60 treatment group were either very dissatisfied (3) or dissatisfied (2) with treatment. Moreover, one subject (subject 324) in the 50/90 treatment group was found to be very dissatisfied (on Day 21) or dissatisfied (on Day 28) with treatment. A possible factor that might have contributed to the dissatisfaction could be due to the fact that subjects 301, 305 and 324 experienced AEs. In the placebo treatment group, three subjects were dissatisfied with treatment from Day 14 to Day 28.

Mixed Model Analysis

Change from baseline in Investigator and subject's assessments of severity of rhytids scales, at rest and at maximum frown/smile, separately, was evaluated using the repeated measures model (mixed model). The Investigator's evaluation of the severity of rhytids (difference between different doses at different days) is presented in Tables 30-31 (at rest and at maximum frown/smile) and the subject's evaluation of the severity of rhytids (difference between different doses at different days) is presented in Tables 32-33 (at rest and at maximum frown/smile). The variable analyzed and presented in this section is change from baseline in Investigator and subject's assessments of severity of rhytids scales, at rest and at maximum smile, separately.

Glabellar Lines (GL):

The Investigator's evaluation of rhytids at maximum frown indicated that from Day 2 to Day 28 the change from baseline in mean MAS scores in the 50/60 unit QM1114-DP treatment group showed a statistically significant difference when compared to scores in the placebo treatment group. A significant result (P<0.05) was also reported from Day 3 to Day 28 when the change from baseline in mean MAS scores in the 50/90 unit QM1114-DP treatment group were compared to scores in the placebo treatment group (Table 30A). Similar patterns were also reported for the subject's evaluation of rhytids at maximum frown (Table 32A), with statistically significant differences from placebo from Day 2 or Day 3 to Day 28 at both QM1114-DP dose levels. For the Investigator evaluation of rhytids at rest, change from baseline in mean MAS scores over time in the 50/60 unit QM1114-DP treatment group were not significantly different when compared to scores in the placebo treatment group (Table 31A). However, on Day 3, Day 21 and Day 28 the change from baseline in mean MAS scores in the 50/90 unit QM1114-DP treatment group showed a statistically significance difference (P<0.05) when compared to scores in the placebo treatment group (Table 31A). For the subjects evaluation of rhytids at rest, change from baseline in mean MAS scores were statistically significant (P<0.05) from Day 7 to Day 28 in both the 50/60 unit and 50/90 QM1114-DP treatment groups when compared to scores in the placebo group (Table 33A).

Lateral Canthal Lines (LCL):

The Investigator's evaluation of rhytids of the left lateral canthal region at maximum smile indicated that from Day 2 to Day 28 the change from baseline in mean MAS scores in the 50/60 unit QM1114-DP treatment group showed a statistically significant difference when compared to scores in the placebo treatment group. Moreover, with the exception of Day 2 and Day 14, this pattern was also seen in the 50/90 unit QM1114-DP treatment group (Table 30B). In contrast, this trend was not so obvious for the Investigator's evaluation of rhytids of the right lateral canthal region at maximum smile. For Investigator's evaluation of rhytids of the right LCL, statistically significant differences from placebo were reported on Day 7 and Day 28 for the 50/60 unit QM1114-DP treatment group. For the 50/90 unit QM1114-DP treatment group, statistically significant differences from placebo were noted from Day 3 to Day 7 and on Day 28 (Table 30C). For the subject's evaluation of rhytids of the left LCL at maximum smile, statistically significant differences (P<0.05) from placebo were noted from Day 14 to Day 28 for the 50/60 unit QM1114-DP treatment group and from Day 7 to Day 28 for the 50/90 unit QM1114-DP treatment group (Table 32B). Similar differences were also noted in treatment groups for right LCL at maximum smile. For right LCL, the change from baseline in mean MAS scores in the 50/60 unit QM1114-DP treatment group showed a statistically significant difference from placebo from Day 14 to Day 28 and from Day 3 to Day 28 in the 50/90 unit QM1114-DP treatment group (Table 32C).

The Investigator's evaluation of rhytids of the lateral canthal region of the left side of the face at rest showed that change from baseline in mean MAS scores from week 3 (Day 21) to week 4 (Day 28) in both the 50/60 and 50/90 unit QM1114-DP treatment groups showed a statistically significant difference (P<0.05) when compared to scores in the placebo treatment group (Table 31B). However, Investigator's evaluation of rhytids of the lateral canthal region of the right side of the face at rest indicated that the change from baseline in the mean MAS score was significantly different to the placebo score at week 4 (Day 28) only for both the 50/60 and 50/90 unit QM1114-DP treatment groups (Table 31C).

For subject's evaluation of rhytids at rest, with the exception of Day 7, statistically significant results (P<0.05) were reported for left LCL from Day 2 to Day 28 when the 50/90 unit QM1114-DP treatment group was compared to placebo (Table 33B). However, no statistically significant change from baseline in mean MAS scores were reported when the 50/60 unit QM1114-DP treatment group was compared to scores in the placebo treatment group for left LCL (Table 33B). For the subject's evaluation of rhytids at rest of the right LCL no statistically significant change from baseline in mean MAS scores were seen between the 50/60 unit QM1114-DP and placebo treatment group (Table 7C). In contrast, statistically significant MAS scores in comparison to placebo were reported on Day 21 and Day 28 for the 50/90 unit QM1114-DP treatment group (Table 33C).

TABLE 30

Severity of Rhytids: Investigator's Evaluation at Maximum Frown/Smile: Difference between QM1114-DP Doses and Placebo in Change from Baseline—Mixed Model (A, GL indication; B, LCL indication [left]; C, LCL indication [right])
MAXIMUM FROWN

| Comparison | Visit | Difference in Means* | P-values | 98% Confidence Interval Lower Limit | 98% Confidence Interval Upper Limit |
|---|---|---|---|---|---|
| A: Indication: GL, maximum frown, Investigator's evaluation | | | | | |
| QM1114-DP 50/60 units—Pooled Placebo | Day 2 | −1.50 | <.0001 | −2.14 | −0.86 |
| | Day 3 | −1.08 | 0.0012 | −1.72 | −0.44 |
| | Day 7 | −1.50 | <.0001 | −2.14 | −0.86 |
| | Day 14 | −1.17 | 0.0005 | −1.81 | −0.53 |
| | Day 21 | −1.50 | <.0001 | −2.14 | −0.86 |
| | Day 28 | −1.67 | <.0001 | −2.31 | −1.03 |
| | Overall | −1.40 | <.0001 | −1.67 | −1.14 |
| QM1114-DP 50/90 units—Pooled Placebo | Day 2 | −0.50 | 0.1248 | −1.14 | 0.14 |
| | Day 3 | −0.75 | 0.0225 | −1.39 | −0.11 |
| | Day 7 | −1.67 | <.0001 | −2.31 | −1.03 |
| | Day 14 | −1.17 | 0.0005 | −1.81 | −0.53 |
| | Day 21 | −1.67 | <.0001 | −2.31 | −1.03 |
| | Day 28 | −1.67 | <.0001 | −2.31 | −1.03 |
| | Overall | −1.23 | <.0001 | −1.50 | −0.97 |
| QM1114-DP 50/90 units—QM1114-DP 50/60 units | Day 2 | 1.00 | 0.0008 | 0.43 | 1.58 |
| | Day 3 | 0.34 | 0.2475 | −0.24 | 0.91 |
| | Day 7 | −0.16 | 0.5701 | −0.74 | 0.41 |
| | Day 14 | 0.00 | 0.9934 | −0.57 | 0.58 |
| | Day 21 | −0.16 | 0.5701 | −0.74 | 0.41 |
| | Day 28 | 0.00 | 0.9934 | −0.57 | 0.58 |
| | Overall | 0.17 | 0.1595 | −0.07 | 0.41 |
| B: Indication: LCL (L), maximum smile, Investigators evaluation | | | | | |
| QM1114-DP 50/60 units—Pooled Placebo | Day 2 | −0.75 | 0.0407 | −1.46 | −0.03 |
| | Day 3 | −0.83 | 0.0233 | −1.54 | −0.12 |
| | Day 7 | −1.32 | 0.0004 | −2.04 | −0.02 |
| | Day 14 | −1.00 | 0.0068 | −1.71 | −0.28 |
| | Day 21 | −1.08 | 0.0035 | −1.79 | −0.37 |
| | Day 28 | −1.25 | 0.0008 | −1.96 | −0.53 |
| | Overall | −1.04 | <.0001 | −1.34 | −0.73 |
| QM1114-DP 50/90 units—Pooled Placebo | Day 2 | −0.08 | 0.8200 | −0.79 | 0.63 |
| | Day 3 | −0.83 | 0.0220 | −1.54 | −0.12 |
| | Day 7 | −1.16 | 0.0016 | −1.87 | −0.46 |
| | Day 14 | −0.66 | 0.0655 | −1.37 | 0.04 |

TABLE 30-continued

Severity of Rhytids: Investigator's Evaluation at Maximum Frown/Smile: Difference between QM1114-DP Doses and Placebo in Change from Baseline—Mixed Model (A, GL indication; B, LCL indication [left]; C, LCL indication [right])
MAXIMUM FROWN

| Comparison | Visit | Difference in Means* | P-values | 98% Confidence Interval Lower Limit | 98% Confidence Interval Upper Limit |
|---|---|---|---|---|---|
| | Day 21 | −0.91 | 0.0120 | −1.62 | −0.21 |
| | Day 28 | −0.91 | 0.0120 | −1.62 | −0.21 |
| | Overall | −0.76 | <.0001 | −1.05 | −0.47 |
| QM1114-DP 50/90 units—QM1114-DP 50/60 units | Day 2 | 0.66 | 0.0401 | 0.03 | 1.30 |
| | Day 3 | −0.00 | 0.9947 | −0.64 | 0.63 |
| | Day 7 | 0.16 | 0.6067 | −0.47 | 0.80 |
| | Day 14 | 0.33 | 0.3013 | −0.30 | 0.96 |
| | Day 21 | 0.16 | 0.6067 | −0.47 | 0.80 |
| | Day 28 | 0.33 | 0.3013 | −0.30 | 0.96 |
| | Overall | 0.28 | 0.0401 | 0.01 | 0.54 |
| C: Indication: LCL (R), maximum smile, Investigators evaluation | | | | | |
| QM1114-DP 50/60 units—Pooled Placebo | Day 2 | 0.01 | 0.9861 | −0.79 | 0.80 |
| | Day 3 | −0.74 | 0.0659 | −1.54 | 0.05 |
| | Day 7 | −0.91 | 0.0251 | −1.70 | −0.12 |
| | Day 14 | −0.58 | 0.1519 | −1.37 | 0.22 |
| | Day 21 | −0.74 | 0.0659 | −1.54 | 0.05 |
| | Day 28 | −0.99 | 0.0148 | −1.79 | −0.20 |
| | Overall | −0.66 | 0.0002 | −1.00 | −0.32 |
| QM1114-DP 50/90 units—Pooled Placebo | Day 2 | −0.16 | 0.6895 | −0.95 | 0.63 |
| | Day 3 | −0.91 | 0.0251 | −1.70 | −0.12 |
| | Day 7 | −1.24 | 0.0025 | −2.04 | −0.45 |
| | Day 14 | −0.74 | 0.0659 | −1.54 | 0.05 |
| | Day 21 | −0.74 | 0.0659 | −1.54 | 0.05 |
| | Day 28 | −0.99 | 0.0148 | −1.79 | −0.20 |
| | Overall | −0.80 | <.0001 | −1.14 | −0.46 |
| QM1114-DP 50/90 units—QM1114-DP 50/60 units | Day 2 | −0.17 | 0.6384 | −0.87 | 0.54 |
| | Day 3 | −0.17 | 0.6384 | −0.87 | 0.54 |
| | Day 7 | −0.33 | 0.3483 | −1.04 | 0.37 |
| | Day 14 | −0.17 | 0.6384 | −0.87 | 0.54 |
| | Day 21 | 0.00 | 1.0000 | −0.70 | 0.70 |
| | Day 28 | −0.00 | 1.0000 | −0.70 | 0.70 |
| | Overall | −0.14 | 0.3380 | −0.43 | 0.15 |

*A negative difference in means indicates a greater improvement of severity of rhytids of the first of the compared groups and vice versa.

Table 31

Severity of Rhytids: Investigator's Evaluation at Rest: Difference between QM1114-DP Doses and Placebo in Change from Baseline—Mixed Model (A, GL indication; B, LCL indication [left]; C, LCL indication [right])
REST

| Comparison | Visit | Difference in Means* | P-values | 95% Confidence Interval Lower Limit | 95% Confidence Interval Upper Limit |
|---|---|---|---|---|---|
| A: Indication: GL, rest, Investigator's evaluation | | | | | |
| QM1114-DP 50/60 units—Pooled Placebo | Day 2 | −0.21 | 0.4642 | −0.79 | 0.36 |
| | Day 3 | −0.38 | 0.1933 | −0.95 | 0.20 |
| | Day 7 | −0.13 | 0.6560 | −0.70 | 0.45 |
| | Day 14 | −0.13 | 0.6560 | −0.70 | 0.45 |
| | Day 21 | −0.38 | 0.1933 | −0.95 | 0.20 |
| | Day 28 | −0.55 | 0.0627 | −1.12 | 0.03 |
| | Overall | −0.30 | 0.0157 | −0.53 | −0.06 |
| QM1114-DP 50/90 units—Pooled Placebo | Day 2 | −0.32 | 0.2733 | −0.89 | 0.26 |
| | Day 3 | −0.82 | 0.0058 | −1.39 | −0.24 |
| | Day 7 | −0.40 | 0.1678 | −0.98 | 0.17 |
| | Day 14 | −0.57 | 0.0523 | −1.14 | 0.01 |
| | Day 21 | −0 67 | 0.0266 | −1.23 | −0.08 |

Table 31-continued

Severity of Rhytids: Investigator's Evaluation at Rest: Difference between QM1114-DP Doses and Placebo in Change from Baseline—Mixed Model (A, GL indication; B, LCL indication [left]; C, LCL indication [right])
REST

| Comparison | Visit | Difference in Means* | P-values | 95% Confidence Interval Lower Limit | Upper Limit |
|---|---|---|---|---|---|
| | Day 28 | -0.65 | 0.0266 | -0.23 | -0.08 |
| | Overall | -0.57 | <.0001 | -0.80 | -0.33 |
| QM1114-DP 50/90 units—QM1114-DP 50/60 units | Day 2 | -0.11 | 0.6856 | -0.62 | 0.41 |
| | Day 3 | -0.44 | 0.0948 | -0.96 | 0.08 |
| | Day 7 | -0.27 | 0.2975 | -0.79 | 0.24 |
| | Day 14 | -0.44 | 0.0948 | -0.96 | 0.08 |
| | Day 21 | -0.27 | 0.2975 | -0.79 | 0.24 |
| | Day 28 | -0.11 | 0.6856 | -0.62 | 0.41 |
| | Overall | -0.27 | 0.0150 | -0.49 | -0.05 |
| B: Indication: LCL (L), rest, Investigator's evaluation | | | | | |
| QM1114-DP 50/60 units—Pooled Placebo | Day 2 | -0.69 | 0.0363 | -1.34 | -0.05 |
| | Day 3 | -0.19 | 0.5534 | -0.84 | 0.45 |
| | Day 7 | -0.44 | 0.1768 | -1.09 | 0.20 |
| | Day 14 | -0.36 | 0.2717 | -1.01 | 0.29 |
| | Day 21 | -0.86 | 0.0100 | -1.51 | -0.21 |
| | Day 28 | -0.86 | 0.0100 | -1.51 | -0.21 |
| | Overall | -0.57 | <.0001 | -0.84 | -0.30 |
| QM1114-DP 50/90 units—Pooled Placebo | Day 2 | -0.53 | 0.1095 | -1.18 | 0.12 |
| | Day 3 | 0.14 | 0.6696 | -0.51 | 0.79 |
| | Day 7 | -0.28 | 0.3973 | -0.93 | 0.37 |
| | Day 14 | -0.03 | 0.9337 | -0.68 | 0.62 |
| | Day 21 | -0.86 | 0.0100 | -1.51 | -0.21 |
| | Day 28 | -1.03 | 0.0023 | -1.68 | -0.38 |
| | Overall | -0.43 | 0.0020 | -0.70 | -0.16 |
| QM1114-DP 50/90 units—QM1114-DP 50/60 units | Day 2 | 0.17 | 0.5680 | -0.41 | 0.75 |
| | Day 3 | 0.33 | 0.2549 | -0.25 | 0.91 |
| | Day 7 | 0.17 | 0.5680 | -0.41 | 0.75 |
| | Day 14 | 0.33 | 0.2549 | -0.25 | 0.91 |
| | Day 21 | -0.00 | 1.0000 | -0.58 | 0.58 |
| | Day 28 | -0.17 | 0.5680 | -0.75 | 0.41 |
| | Overall | 0.14 | 0.2453 | -0.10 | 0.38 |
| C: Indication: LCL (R), rest, Investigator's evaluation | | | | | |
| QM1114-DP 50/60 units—Pooled Placebo | Day 2 | -0.44 | 0.2009 | -1.11 | 0.24 |
| | Day 3 | -0.44 | 0.2009 | -1 11 | 0.24 |
| | Day 7 | -0.02 | 0.9528 | -0.69 | 0.65 |
| | Day 14 | -0.52 | 0.1286 | -1.19 | 0.15 |
| | Day 21 | -0.52 | 0.1286 | -1.19 | 0.15 |
| | Day 28 | -0.77 | 0.0257 | -1.44 | -0.10 |
| | Overall | -0.45 | 0.0027 | -0.74 | -0.16 |
| QM1114-DP 50/90 units—Pooled Placebo | Day 2 | -0.55 | 0.1082 | -1.23 | 0.12 |
| | Day 3 | -0.39 | 0.2592 | -1.07 | 0.29 |
| | Day 7 | -0.30 | 0.3749 | -0.98 | 0.37 |
| | Day 14 | -0.30 | 0.3749 | -0.98 | 0.37 |
| | Day 21 | -0.64 | 0.0654 | -1.32 | 0.04 |
| | Day 28 | -0.89 | 0.0111 | -1.57 | -0.21 |
| | Overall | -0.51 | 0.0011 | -0.81 | -0.21 |
| QM1114-DP 50/90 units—QM1114-DP 50/60 units | Day 2 | -0.12 | 0.6958 | -0.72 | 0.48 |
| | Day 3 | 0.05 | 0.8712 | -0.55 | 0.65 |
| | Day 7 | -0.28 | 0.3463 | -0.88 | 0.31 |
| | Day 14 | 0.22 | 0.4750 | -0.38 | 0.81 |
| | Day 21 | -0.12 | 0.6958 | -0.72 | 0.48 |
| | Day 28 | -0.12 | 0.6958 | -0.72 | 0.48 |
| | Overall | -0.06 | 0.6154 | -0.31 | 0.18 |

*A negative difference in means indicates a greater improvement of severity of rhytids of the first of the compared groups and vice versa.

TABLE 32

Severity of Rhytids: Subject's Evaluation at Maximum Frown/Smile: Difference between QM1114-DP Doses and Placebo in Change from Baseline—Mixed Model (A, GL indication; B, LCL indication [left]; C, LCL indication [right])
MAXIMUM FROWN

| Comparison | Visit | Difference in Means* | P-values | 95% Confidence Interval Lower Limit | Upper Limit |
|---|---|---|---|---|---|
| A: Indication: GL, maximum frown, Subject's evaluation | | | | | |
| QM1114-DP 50/60 units—Pooled Placebo | Day 2 | -1.01 | 0.0130 | -1.80 | -0.22 |
| | Day 3 | -1.51 | 0.0003 | -2.30 | -0.72 |
| | Day 7 | -1.68 | <.0001 | -2.47 | -0.89 |
| | Day 14 | -1.59 | 0.0001 | -2.38 | -0.80 |
| | Day 21 | -1.84 | <.0001 | -2.63 | -1.05 |
| | Day 28 | -1.84 | <.0001 | -2.63 | -1.05 |
| | Overall | -1.58 | <.0001 | -1.90 | -1.26 |
| QM1114-DP 50/90 units—Pooled Placebo | Day 2 | -0.60 | 0.1335 | -1.40 | 0.19 |
| | Day 3 | -1.44 | 0.0005 | -2.23 | -0.64 |
| | Day 7 | -1.94 | <.0001 | -2.73 | -1.14 |
| | Day 14 | -1.48 | 0.0006 | -2.31 | -0.65 |
| | Day 21 | -1.94 | <.0001 | -2.73 | -1.14 |
| | Day 28 | -2.10 | <.0001 | -2.90 | -1.31 |
| | Overall | -1.58 | <.0001 | -1.91 | -1.25 |
| QM1114-DP 50/90 units—QM1114-DP 50/60 units | Day 2 | 0.41 | 0.2559 | -0.30 | 1.11 |
| | Day 3 | 0.07 | 0 8370 | -0.63 | 0.78 |
| | Day 7 | -0.26 | 0.4665 | -0.97 | 0.45 |
| | Day 14 | 0.11 | 0.7923 | -0.63 | 0.86 |
| | Day 21 | -0.09 | 0.7935 | -0.80 | 0.61 |
| | Day 28 | -0.26 | 0.4665 | -0.97 | 0.45 |
| | Overall | -0.00 | 0 9820 | -0.30 | 0.29 |
| B: indication: LCL (L), maximum smile, Subject's evaluation | | | | | |
| QM1114-DP 50/60 units—Pooled Placebo | Day 2 | -0.57 | 0.2748 | -1.59 | 0.46 |
| | Day 3 | -0.48 | 0.3513 | -1.51 | 0.54 |
| | Day 7 | -0.65 | 0.2108 | -1.67 | 0.37 |
| | Day 14 | -1.65 | 0.0020 | -2.67 | -0.63 |
| | Day 21 | -1.23 | 0.0190 | -2.26 | -0.21 |
| | Day 28 | -1.32 | 0.0125 | -2.34 | -0.29 |
| | Overall | -0.98 | <.0001 | -1.41 | -0.55 |
| QM1114-DP 50/90 units—Pooled Placebo | Day 2 | -0.70 | 0.2022 | -1.17 | 0.38 |
| | Day 3 | -0.61 | 0.2610 | -1.69 | 0.46 |
| | Day 7 | -1.11 | 0.0431 | -2.19 | -0.04 |
| | Day 14 | -1.48 | 0.0094 | -2.58 | -0.37 |
| | Day 21 | -1.70 | 0.0024 | -2.77 | -0.62 |
| | Day 28 | -1.78 | 0.0015 | -2.86 | -0.70 |
| | Overall | -1.23 | <.0001 | -1.77 | -0.68 |
| QM1114-DP 50/90 units—QM1114-DP 50/60 units | Day 2 | -0.13 | 0.7831 | -1.07 | 0.81 |
| | Day 3 | -0.13 | 0.7831 | -1.07 | 0.81 |
| | Day 7 | -0.46 | 0.3287 | -1.40 | 0.48 |
| | Day 14 | 0.17 | 0.7253 | -0.80 | 1.15 |
| | Day 21 | -0.46 | 0.3287 | -1.40 | 0.48 |
| | Day 28 | -0.46 | 0.3287 | -1.40 | 0.48 |
| | Overall | -0.25 | 0.2676 | -0.69 | 0.19 |
| C: Indication: LCL (R), maximum smile, Subject's evaluation | | | | | |
| QM1114-DP 50/60 units—Pooled Placebo | Day 2 | -0.23 | 0.6657 | -1.28 | 0.82 |
| | Day 3 | -0.73 | 0.1713 | -1.78 | 0.32 |
| | Day 7 | -0.73 | 0.1713 | -1.78 | 0.32 |
| | Day 14 | -1.65 | 0.0026 | -2.70 | -0.59 |
| | Day 21 | -1.23 | 0.0226 | -2.28 | -0.18 |
| | Day 26 | -1.31 | 0.0151 | -2.36 | -0.26 |
| | Overall | -0.98 | <.0001 | -1.43 | -0.53 |
| QM1114-DP 50/90 units—Pooled Placebo | Day 2 | -0.92 | 0.0997 | -2.03 | 0.18 |
| | Day 3 | -1.26 | 0.0261 | -2.36 | -0.15 |
| | Day 7 | -1.59 | 0.0053 | -2.69 | -0.49 |
| | Day 14 | -1.72 | 0.0034 | -2.86 | -0.59 |
| | Day 21 | -1.92 | 0.0009 | -3.03 | -0.82 |
| | Day 28 | -2.34 | <.0001 | -3.44 | -1.24 |
| | Overall | -1.63 | <.0001 | -2.19 | -1.06 |
| QM1114-DP 50/90 units—QM1114-DP 50/60 units | Day 2 | -0.69 | 0.1511 | -1.65 | 0.26 |
| | Day 3 | -0.53 | 0.2739 | -1.48 | 0.43 |
| | Day 7 | -0.86 | 0.0761 | -1.81 | 0.09 |
| | Day 14 | -0.07 | 0.8813 | -1.07 | 0.92 |
| | Day 21 | -0.69 | 0.1511 | -1.65 | 0.26 |

TABLE 32-continued

Severity of Rhytids: Subject's Evaluation at Maximum Frown/Smile: Difference between QM1114-DP Doses and Placebo in Change from Baseline—Mixed Model (A, GL indication; B, LCL indication [left]; C, LCL indication [right])
MAXIMUM FROWN

| Comparison | Visit | Difference in Means* | P-values | 95% Confidence Interval Lower Limit | Upper Limit |
|---|---|---|---|---|---|
| | Day 28 | −1.03 | 0.0350 | −1.98 | −0.07 |
| | Overall | −0.65 | 0.0041 | −1.08 | −0.21 |

*A negative difference in means indicates a greater improvement of severity of rhytids of the first of the compared groups and vice versa.

TABLE 33

Severity of Rhytids: Subject's Evaluation at Rest: Difference between QM1114-DP Doses and Placebo in Change from Baseline—Mixed Model (A, GL indication; B, LCL indication [left]; C, LCL indication [right])
REST

| Comparison | Visit | Difference in Means | P-values | 95% Confidence Interval Lower Limit | Upper Limit |
|---|---|---|---|---|---|
| A: Indication: GL, rest, Subject's evaluation | | | | | |
| QM1114-DP 50/60 units—Pooled Placebo | Day 2 | −0.45 | 0.1128 | −1.02 | 0.11 |
| | Day 3 | −0.45 | 0.1128 | −1.02 | 0.11 |
| | Day 7 | −0.70 | 0.0150 | −1.27 | −0.14 |
| | Day 14 | −0.70 | 0.0150 | −1.27 | −0.14 |
| | Day 21 | −0.87 | 0.0029 | −1.43 | −0.31 |
| | Day 28 | −0.95 | 0.0012 | −1.52 | −0.39 |
| | Overall | −0.69 | <.0001 | −0.92 | −0.46 |
| QM1114-DP 50/90 units—Pooled Placebo | Day 2 | −0.75 | 0.0102 | −1.32 | −0.18 |
| | Day 3 | −0.42 | 0.1456 | −0.99 | −0.15 |
| | Day 7 | −0.67 | 0.0217 | −1.24 | −0.10 |
| | Day 14 | −1.03 | 0.0010 | −1.62 | −0.43 |
| | Day 21 | −0.67 | 0.0217 | −1.24 | −0.10 |
| | Day 28 | −1.25 | <.0001 | −1.82 | −0.68 |
| | Overall | −0.80 | <.0001 | −1.05 | −0.55 |
| QM1114-DP 50/90 units—QM1114-DP 50/60 units | Day 2 | −0.30 | 0.2449 | −0.81 | 0.21 |
| | Day 3 | 0.03 | 0.8967 | −0.48 | 0.54 |
| | Day 7 | 0.03 | 0.8967 | −0.48 | 0.54 |
| | Day 14 | −0.32 | 0.2349 | −0.86 | 0.21 |
| | Day 21 | 0.20 | 0.4370 | −0.31 | 0.71 |
| | Day 28 | −0.30 | 0.2449 | −0.81 | 0.21 |
| | Overall | −0.11 | 0.3298 | −0.33 | 0.11 |
| B: Indication: LCL (L), rest, Subject's evaluation | | | | | |
| QM1114-DP 50/60 units—Pooled Placebo | Day 2 | −0.35 | 0.3866 | −1.14 | 0.45 |
| | Day 3 | −0.01 | 0.9736 | −0.81 | 0.78 |
| | Day 7 | 0.32 | 0.4237 | −0.47 | 1.11 |
| | Day 14 | −0.26 | 0.5104 | −1.06 | 0.53 |
| | Day 21 | −0.51 | 0.2011 | −1.31 | 0.28 |
| | Day 28 | −0.51 | 0.2011 | −1.31 | 0.28 |
| | Overall | −0.22 | 0.1799 | −0.55 | 0.10 |
| QM1114-DP 50/90 units—Pooled Placebo | Day 2 | −1.25 | 0.0036 | −2.09 | −0.42 |
| | Day 3 | −1.09 | 0.0111 | −1.92 | −0.26 |
| | Day 7 | −0.59 | 0.1639 | −1.42 | 0.24 |
| | Day 14 | −1.28 | 0.0039 | −2.13 | −0.42 |
| | Day 21 | −1.92 | <.0001 | −2.75 | −1.09 |
| | Day 28 | −1.59 | 0.0003 | −2.42 | −0.76 |
| | Overall | −1.29 | <.0001 | −1.70 | −0.87 |
| QM1114-DP 50/90 units—QM1114-DP 50/60 units | Day 2 | −0.91 | 0.0214 | −1.68 | −0.14 |
| | Day 3 | −1.07 | 0.0068 | −1.84 | −0.31 |
| | Day 7 | −0.91 | 0.0214 | −1.68 | −0.14 |
| | Day 14 | −1.02 | 0.0126 | −1.81 | −0.22 |
| | Day 21 | −1.41 | 0.0005 | −2.18 | −0.64 |
| | Day 28 | −1.07 | 0.0008 | −1.84 | −0.31 |
| | Overall | −1.06 | <.0001 | −1.48 | −0.65 |

TABLE 33-continued

Severity of Rhytids: Subject's Evaluation at Rest: Difference between QM1114-DP Doses and Placebo in Change from Baseline—Mixed Model (A, GL indication; B, LCL indication [left]; C, LCL indication [right])
REST

| Comparison | Visit | Difference in Means | P-values | 95% Confidence Interval Lower Limit | Upper Limit |
|---|---|---|---|---|---|
| C: Indication: LCL (R), rest, Subject's evaluation | | | | | |
| QM1114-DP 50/60 units—Pooled Placebo | Day 2 | −0.17 | 0.7092 | −1.06 | 0.73 |
| | Day 3 | −0.08 | 0.8510 | −0.98 | 0.81 |
| | Day 7 | 0.08 | 0.8552 | −0.81 | 0.98 |
| | Day 14 | −0.25 | 0.5771 | −1.14 | 0.64 |
| | Day 21 | −0.33 | 0.4581 | −1.23 | 0.56 |
| | Day 28 | −0.50 | 0.2673 | −1.39 | 0.39 |
| | Overall | −0.21 | 0.2583 | −0.58 | 0.16 |
| QM1114-DP 50/90 units—Pooled Placebo | Day 2 | −0.59 | 0.2063 | −1.51 | 0.33 |
| | Day 3 | −0.34 | 0.4646 | −1.26 | 0.58 |
| | Day 7 | −0.17 | 0.7085 | −1.10 | 0.75 |
| | Day 14 | −0.26 | 0.5928 | −1.21 | 0.69 |
| | Day 21 | −1.09 | 0.0212 | −2.01 | −0.17 |
| | Day 78 | −0.92 | 0.0497 | −1.85 | −0.00 |
| | Overall | −0.56 | 0.0116 | −1.00 | −0.13 |
| QM1114-DP 50/90 units—QM1114-DP 50/60 units | Day 2 | −0.42 | 0.3089 | −1.24 | 0.40 |
| | Day 3 | −0.26 | 0.5368 | −1.08 | 0.57 |
| | Day 7 | −0.20 | 0.5368 | −1.08 | 0.57 |
| | Day 14 | −0.01 | 0.9902 | −0.86 | 0.85 |
| | Day 21 | −0.76 | 0.0709 | −1.58 | 0.07 |
| | Day 28 | −0.42 | 0.3089 | −1.24 | 0.40 |
| | Overall | −0.35 | 0.0684 | −0.73 | 0.03 |

Efficacy Conclusions

The efficacy results as measured by the Investigator's and subjects assessment of change in appearance of GL at maximum frown and LCL at maximum smile indicated that QM1114-DP is efficacious in reducing GL and LCL severity (with some exceptions noted for the latter) at maximum frown/smile at both dose levels in comparison to those subjects evaluated in the placebo treatment group. However, for GL and LCL evaluations made at rest, the two QM1114-DP doses was not as efficacious as for the evaluations at maximum frown and maximum smile, and showed different patterns by the Investigator's and subjects assessment. The subject's assessment of GL and LCL satisfaction showed that the majority of subjects in the active treatment groups were either very satisfied or satisfied with treatment through to Day 28. In the placebo treatment group, three subjects were dissatisfied with treatment.

Safety Evaluation

The safety analysis included all 16 subjects who had received a single dose of randomized study medication.

Six subjects received 110 units (50 units in total for GL and 60 units in total for LCL) of QM1114-DP and six subjects received 140 units (50 units in total for GL and 90 units in total for LCL) of QM1114-DP. Four subjects received placebo treatment.

or the purposes of AE analysis, this section primarily deals with those AEs that were treatment emergent, i.e. commencing after dosing with the IMP, and ADRs i.e. where a causal relationship with the IMP was at least a reasonable possibility. There were no SAEs reported during the study, no SUSAR and no subject was withdrawn from the study due to safety reasons.

An overview of AEs by treatment group is presented in Table 34. AEs were reported for each dose level. Thirty two (32) AEs were reported in 11 of 16 (68.8%) subjects of which 24 AEs in 10 (62.5%) subjects overall were judged by the Investigator to be possibly or probably treatment related. Fourteen (14) AEs were reported in 4 of 6 subjects in the 50/60 unit QM1114-DP treatment group and nine AEs reported for 4 of 6 subjects in the 50/90 unit QM1114-DP treatment group. For the placebo treatment group, nine AEs were reported in 3 of 4 subjects. An overview of AEs by SOC assignments and PT is presented in Table 35. For eyelid ptosis, onset ranged between 3 days 22 hours (subject 301) and 14 days (subject 304). The duration of the eyelid ptosis varied from 67 to 87 days. The most frequent treatment related nervous system disorder was headache with an onset between 9 hours (subject 305) to 23 hours (subject 301). The duration of headache varied from 2 days (subject 302) to 13 days (subject 305).

TABLE 34

Summary of AEs

| | QM1114-DP | | | | | | Pooled | | |
| | 50/60 units (N = 6) | | | 50/90 units (N = 6) | | | Placebo N = 4 | | |
| | E | N | % | E | N | % | E | N | % |
|---|---|---|---|---|---|---|---|---|---|
| Total number of AEs | 14 | 4 | 66.7 | 9 | 4 | 66.7 | 9 | 3 | 75.0 |
| Total number of serious AEs | 0 | 0 | 0 | 0 | 0 | 0 | 0 | 0 | 0 |
| Total number of treatment related AEs | 13 | 4 | 66.7 | 6 | 4 | 66.7 | 5 | 2 | 50.0 |
| Total number of treatment related SAEs | 0 | 0 | 0 | 0 | 0 | 0 | 0 | 0 | 0 |
| Total number of subjects with AEs leading to withdrawal | — | 0 | — | — | 0 | — | — | 0 | — |
| Subjects with at least one mild AE | — | 4 | 66.7 | — | 4 | 66.7 | — | 3 | 75.0 |
| Related AE | — | 4 | 66.7 | — | 4 | 66.7 | — | 2 | 50.0 |
| Unrelated AE | — | 1 | 16.7 | — | 2 | 33.3 | — | 1 | 25.0 |
| Subjects with at least one moderate AE | — | 0 | 0.0 | — | 0 | 0.0 | — | 0 | 0.0 |
| Related AE | — | 0 | 0.0 | — | 0 | 0.0 | — | 0 | 0.0 |
| Unrelated AE | — | 0 | 0.0 | — | 0 | 0.0 | — | 0 | 0.0 |
| Subjects with at least one severe AE | — | 0 | 0.0 | — | 0 | 0.0 | — | 0 | 0.0 |
| Related AE | — | 0 | 0.0 | — | 0 | 0.0 | — | 0 | 0.0 |
| Unrelated AE | — | 0 | 0.0 | — | 0 | 0.0 | — | 0 | 0.0 |
| Subjects with At least one ADR | — | 4 | 66.7 | — | 4 | 66.7 | — | 2 | 50.0 |
| Subjects with at least one SUSAR | — | 0 | 0.0 | — | 0 | 0.0 | — | 0 | 0.0 |

E = number of events; N = number of subjects

TABLE 35

Summary of Subjects with AEs Categorized by System Organ Class, Preferred Term and Treatment

| SYSTEM ORGAN CLASS*/PREFERRED TERM** | QM1114-DP | | Pooled |
| | 50/60 units | 50/90 units | Placebo |
|---|---|---|---|
| TOTAL NUMBER OF SUBJECTS WITH AEs | 4 | 4 | 3 |
| EYE DISORDERS | 1 | 1 | 0 |
| Blepharospasm | 1 | 0 | 0 |
| Dry eye | 1 | 0 | 0 |
| Photophobia | 1 | 0 | 0 |
| Vision blurred | 1 | 1 | 0 |
| GASTROINTESTINAL DISORDERS | 1 | 0 | 2 |
| Gastrointestinal disorder | 0 | 0 | 1 |
| Nausea | 1 | 0 | 1 |
| GASTROINTESTINAL VASCULAR CONDITIONS | 0 | 0 | 1 |
| Haemorrhoids | 0 | 0 | 1 |
| GENERAL DISORDERS AND ADMINISTRATION SITE CONDITIONS | 2 | 1 | 1 |
| Fatigue | 1 | 0 | 0 |
| Injection site bruising | 0 | 1 | 1 |

TABLE 35-continued

Summary of Subjects with AEs Categorized by System Organ Class, Preferred Term and Treatment

| SYSTEM ORGAN CLASS*/PREFERRED TERM** | QM1114-DP | | Pooled |
| | 50/60 units | 50/90 units | Placebo |
|---|---|---|---|
| Injection site swelling | 1 | 0 | 0 |
| IMMUNE SYSTEM DISORDERS | 0 | 1 | 0 |
| Dermatitis contact | 0 | 1 | 0 |
| INJURY, POISONING AND PROCEDURAL COMPLICATIONS | 0 | 1 | 1 |

TABLE 35-continued

Summary of Subjects with AEs Categorized by System Organ Class, Preferred Term and Treatment

| SYSTEM ORGAN CLASS*/PREFERRED TERM** | QM1114-DP | | Pooled |
| | 50/60 units | 50/90 units | Placebo |
|---|---|---|---|
| Post-traumatic punctuate intrapidermal haemorrhage | 0 | 1 | 0 |
| Scratch | 0 | 0 | 1 |
| NERVOUS SYSTEM DISORDERS | 3 | 3 | 1 |
| Dysgeusia | 0 | 1 | 0 |
| Eyelid ptosis | 2 | 1 | 0 |
| Headache | 2 | 1 | 1 |
| Paraesthesia | 1 | 1 | 1 |
| RESPIRATORY, THORACIC AND MEDIASTINAL DISORDERS | 1 | 1 | 2 |
| Nasal obstruction | 1 | 1 | 0 |
| Oropharyngeal pain | 0 | 0 | 1 |
| Rhinorrhoea | 0 | 0 | 1 |

85

TABLE 35-continued

Summary of Subjects with AEs Categorized by System
Organ Class, Preferred Term and Treatment

| SYSTEM ORGAN CLASS*/PREFERRED | QM1114-DP | | Pooled |
|---|---|---|---|
| TERM** | 50/60 units | 50/90 units | Placebo |
| SKN AND SUBCUTANEOUS TISSUE DISORDERS | 2 | 0 | 0 |
| Skin tightness | 1 | 0 | 0 |

Only treatment emergent AEs are summarised
*Multiple occurrences within a SOC by a subject were counted once per SOC
**Mulfipte occurrences of a PT by a subject were counted once per PT Safety Conclusions Overall, the most commonly reported SOC of AEs amongst the treatment groups were nervous system disorders and general disorders and administrative site conditions. The same holds true for treatment related AEs. The most frequent nervous system disorder was headache reported in four subjects and the most frequent general disorders and administrative site conditions amongst subjects was injection site bruising reported in two subjects. In light of these findings, in the sections below AEs associated with nervous system disorders and general disorders and administrative site conditions will be focused upon in order to draw parallels between the treatments in terms of these AEs.

The primary objective of this Phase I study was to determine the safety and tolerability of QM1114-DP at each dose level in healthy male and female subjects for the treatment of rhytids of the glabellar and lateral canthal regions. In this part of the study involving GL and LCL when treated in combination, there were no SAEs and no withdrawals due to AEs or any other reasons. Thirty two (32) AEs were reported in 11 of 16 subjects of which 24 AEs in 10 subjects overall were judged by the Investigator to be possibly or probably treatment related. The other AEs (8 AEs) were judged by the Investigator to be unrelated to treatment. All AEs were of mild intensity. AEs were reported at each dose level with the highest number (14 AEs) reported for subjects in the 50/60 QM1114-DP treatment group.

At the highest dose level (50/90 unit QM1114-DP) the number of AEs (9 AEs) was the same as reported for the pooled placebo group of 4 subjects. The most commonly reported AEs amongst the treatment groups were nervous system disorders and general disorders and administrative site conditions. This was also applicable for treatment related AEs whereby nervous system disorders and general disorders and administrative site conditions were the most common. The most frequent nervous system disorder was headache reported in four subjects and the most frequent general disorders and administrative site conditions were injection site bruising. Three instances of eyelid ptosis of mild intensity were noted for three subjects overall in the active treatment groups (subjects 301 and 304 [50/60 unit QM1114-DP treatment group] and subject 324 [50/90 unit QM1114-DP treatment group]).

Some subjects were noted to have had elevations in their biochemistry parameters on specific days during the study. However, these were judged by the Investigator as not related to treatment. In conclusion, there were no clinically significant changes in haematology, biochemistry and urinalysis parameters during the study and no clinically significant physical examination findings. No subject had clinically significant findings in their focused physical examination of the eyes and face for local warmth, itching, pain, oedema/induration, erythema or bruising during the study. With the exception of one subject (304) that had a slightly lower tympanic temperature measurement, all subjects were found to have normal values in their vital signs. The ECG results showed that some subjects were noted to have had increases and decreases in the PR interval during the study. There were also increases in the QTcB reported for some subjects during the study. However, the isolated departures from the normal ranges in ECG recordings were considered by the Investigator as not clinically significant and not related to the study drug.

Discussion and Overall Conclusions

The primary objective of this Phase I study was to evaluate the safety and tolerability of QM1114-DP at each dose level and the secondary objective was to assess the efficacy of QM1114-DP at each dose level for the temporary improvement of facial lines of the glabellar and lateral canthal regions in healthy male and female subjects. In clinical use, approximately 50% of the people treated with BoNT-A for the correction of facial lines in the upper third of the face receive treatment of both the GL and LCL (Rzany et al., 2007).

In this study, three instances of eyelid ptosis of mild intensity were noted for three subjects overall in the active treatment groups (two subjects in the 50/60 unit QM1114-DP treatment group and one subject in the 50/90 unit QM1114-DP treatment group). This is in comparison to Example 1 (GL alone) in which the incidences of eyelid ptosis of mild intensity were only reported in subjects administered the maximum dose level (two events in two subjects in the 75 unit QM1114-DP treatment group).

Amongst individual subjects, the most commonly reported AEs were nervous system disorders. This was also relevant for treatment related AEs. Headache (reported in four subjects) was the most common nervous system disorder followed by eyelid ptosis (reported in three subjects). All AEs were of mild intensity and there were no SAEs or any withdrawals due to AEs. During the course of the study there were no clinically significant changes in haematology, biochemistry and urinalysis parameters. Moreover, there were no clinically significant physical findings. Subjects had vital signs within the normal ranges and there were no clinically significant findings observed in the ECG recordings made during the study.

In conclusion, the vast majority of the treatment related AEs were associated with nervous system disorders and general disorders and administrative site conditions. These treatment related AEs were within expectations according to the reference safety information and with the exception of eyelid ptosis, consistent with AEs observed from Part 1 (GL), Part 2 (LCL) and in general from previous clinical studies using other BoNT-A products.

In this study the efficacy data indicated that when used in combination QM1114-DP was efficacious in reducing both GL and LCL severity at maximum frown/smile at both dose levels in comparison to those subjects evaluated in the placebo treatment group. The mixed model analysis for the Investigators evaluation of GL showed that from Day 2-3 to Day 28 the change from baseline in mean MAS scores in the 50/60 and 50/90 unit QM1114-DP treatment groups showed a statistically significant difference (P<0.05) when compared to scores in the placebo treatment group. Similar patterns were also reported for the subject's evaluation of rhytids at maximum frown, with statistically significant differences from placebo from Day 2 or Day 3 to Day 28 at both QM1114-DP dose levels.

With some exceptions, the Investigator's evaluation of rhytids of the lateral canthal region at maximum smile also showed that the change from baseline in mean MAS scores (left side) in the 50/60 and 50/90 unit QM1114-DP treatment groups showed a statistically significant difference when compared to scores in the placebo treatment group. For the right side, the difference between the QM1114-DP treatment groups and the placebo treatment group was less evident. The subject's assessment of GL and LCL satisfaction showed that the majority of subjects in the active treatment groups were either very satisfied or satisfied with treatment through to Day 28 unless they had AEs which could have contributed to the dissatisfaction of some subjects in the active treatment groups. In the placebo treatment group, three subjects were reported to have been dissatisfied with treatment.

Overall Conclusions:

Both doses were considered safe and well tolerated for the temporary improvement of the GL and LCL, when treated in combination.

There were no SAEs in this study.

There were no subject withdrawals due to AEs or any other reason.

All AEs were of mild intensity.

Investigator's and subject's evaluation of rhytid severity at maximum frown indicated that QM1114-DP was efficacious at both dose levels in reducing GL severity in comparison to placebo. The effect remained until Day 28.

Investigator's and subject's evaluation of rhytid severity at maximum smile indicated that, in main, QM1114-DP was efficacious at both dose levels in reducing LCL severity in comparison to placebo.

Subject's evaluation of rhytid severity at rest indicated that QM1114-DP was efficacious at both dose levels in reducing GL severity in comparison to placebo. The effect remained until Day 28. However, efficacy was not apparent according to the Investigator's assessment.

Investigator's evaluation of rhytid severity at rest indicated first at Day 21 and Day 28 that QM1114-DP was efficacious at both dose levels in reducing LCL severity in comparison to placebo. Subject evaluation showed only efficacy of the higher dose (QM1114-DP 50/90 units) at a few time-points.

The subject's assessment of GL and LCL satisfaction showed that the majority of subjects in the active treatment groups were either very satisfied or satisfied with treatment through to Day 28.

What is claimed is:

1. A method of treating moderate to severe lateral canthal lines (LCL) in a human subject having LCL, comprising administering to the subject 30 to 75 LD50 units of a RelabotulinumtoxinA by subdermal, transdermal, intradermal, or intramuscular injection of a liquid composition comprising 10 to 200 LD50 units per mL of the RelabotulinumtoxinA, thereby reducing the appearance of moderate to severe LCL, wherein the liquid composition has a pH between 6.0 and 7.5 and further comprises:

(a) sodium chloride (NaCl) at a concentration of 100-300 mM;

(b) potassium chloride (KCl) at a concentration of 1-25 mM;

(c) two to four sources of phosphate ions independently selected from sodium phosphate, potassium phosphate, di-sodium hydrogen phosphate dehydrate, and sodium dihydrogen phosphate dehydrate, wherein each source of phosphate ions is independently at a concentration of 1-50 mM;

(d) at least one amino acid selected from alanine, valine, leucine, isoleucine, methionine, phenylalanine, tyrosine, and tryptophan at a concentration of about 0.75 to about 2.25 mg/mL; and (e) at least one non-ionic surfactant selected from a polysorbate and a nonoxynol at a concentration of about 0.1% (v/v) to about 1.5% (v/v);

wherein the liquid composition is not reconstitution from a lyophilized or freeze-dried form by a physician prior to administration; and wherein the LD50 unit value is determined using a gelatine phosphate buffer.

2. The method of claim 1, where the liquid composition comprises two sources of phosphate ions.

3. The method of claim 1, wherein the amino acid is in the L isoform.

4. The method of claim 1, wherein the amino acid is present at a concentration of 0.75 to 2.25 mg/mL and the non-ionic surfactant is present at a concentration of 0.1% (v/v) to 1.5% (v/v).

5. The method of claim 1, wherein the pH of the liquid composition is between 6.6 and 6.9.

6. The method of claim 1, wherein the RelabotulinumtoxinA has a molecular weight of about 150 kDa.

7. The method of claim 1, wherein the osmolality of the liquid composition is between 270 mosm/kg and 310 mosm/kg.

8. The method of claim 1, wherein 30, 45, 50, 60, or 75 units of RelabotulinumtoxinA is administered to the subject.

9. The method of claim 1, wherein the injection is intramuscular.

10. The method of claim 1, wherein the human subject further has moderate to severe glabellar lines (GL).

11. The method of claim 10, wherein the subject is injected multiple times in the glabellar region.

12. The method of claim 11, wherein adjacent injections are separated by about 0.5 to about 10 cm.

13. The method of claim 11, wherein adjacent injections are separated by about 1.5 to about 3 cm.

14. The method of claim 11, wherein the injections are in the procerus muscle and the corrugator supercillii muscles on each side of the face.

15. The method of claim 14, wherein the injections are first made in the procerus muscle followed by the corrugator supercillii muscles on each side of the face, moving outwards from the median.

16. The method of claim 11, wherein all the injections are about 1 cm above the upper orbital rim and internal to the mid-pupillary lines.

17. The method of claim 11, wherein all the injections are at least 1 cm above the central eyebrow or the bony supraorbital ridge.

18. The method of claim 11, further comprising applying pressure on the upper orbital rim while injecting to minimize risks of regional effect of the botulinum neurotoxin.

19. The method of claim 1, wherein the subject is injected multiple times below the lateral canthus, in the external part of the orbicularis oculi, and/or 1-2 cm from the orbital rim.

20. The method of claim 11, wherein the subject is further injected multiple times below the lateral canthus, in the external part of the orbicularis oculi, and/or 1-2 cm from the orbital rim.

21. The method of claim 1, wherein said method is repeated at intervals from about 1 month to about 6 months.

22. The method of claim 21, wherein said method is repeated at intervals from about 3 months to about 6 months.

23. The method of claim 21, wherein said method is repeated at intervals of about 4 months.

24. A method of treating moderate to severe lateral canthal lines (LCL) in a human subject having LCL, comprising administering to the human subject 30 to 75 LD50 units of a RelabotulinumtoxinA by subdermal, transdermal, intradermal, or intramuscular injection of a liquid composition having a pH between 6.0 and 7.5 comprising the RelabotulinumtoxinA and:

(i) 100 to 300 mM of a first buffering agent selected from sodium chloride, potassium chloride, sodium phosphate, potassium phosphate, di-sodium hydrogen phosphate dehydrate, or sodium dihydrogen phosphate dehydrate;

(ii) 1 to 25 mM of a second buffering agent selected from sodium chloride, potassium chloride, sodium phosphate, potassium phosphate, di-sodium hydrogen phosphate dehydrate, or sodium dihydrogen phosphate dehydrate;

(iii) 1 to 25 mM of a third buffering agent selected from sodium chloride, potassium chloride, sodium phosphate, potassium phosphate, di-sodium hydrogen phosphate dehydrate, or sodium dihydrogen phosphate dehydrate;

(iv) 1 to 25 mM of a fourth buffering agent selected from sodium chloride, potassium chloride, sodium phosphate, potassium phosphate, di-sodium hydrogen phosphate dehydrate, or sodium dihydrogen phosphate dehydrate;

(v) 0.1 to 3.0 mg/mL of one or more stabilizers selected from alanine, valine, leucine, serine, threonine, lysine, histidine, tryptophan, aspartic acid, or glutamic acid; and (vi) 0.05% (v/v) to 2.5% (v/v) of one or more surfactants selected from polysorbates or nonoxynols;

wherein the liquid composition is not reconstitution from a lyophilized or freeze-dried form by a physician prior to administration; and wherein the LD50 unit value is determined using a gelatine phosphate buffer.

25. The method of claim 24, wherein the human subject further has moderate to severe glabellar lines (GL).

* * * * *